(12) United States Patent
Sakasegawa et al.

(10) Patent No.: US 10,900,063 B2
(45) Date of Patent: Jan. 26, 2021

(54) MEASUREMENT OF LP-PLA$_2$ ACTIVITY

(71) Applicant: ASAHI KASEI PHARMA CORPORATION, Tokyo (JP)

(72) Inventors: Shinichi Sakasegawa, Tokyo (JP); Saki Yamaura, Tokyo (JP); Daisuke Sugimori, Fukushima (JP)

(73) Assignee: ASAHI KASEI PHARMA CORPORATION, Tokyo (JP)

( * ) Notice: Subject to any disclaimer, the term of this patent is extended or adjusted under 35 U.S.C. 154(b) by 0 days.

(21) Appl. No.: 16/306,936

(22) PCT Filed: Jun. 15, 2017

(86) PCT No.: PCT/JP2017/022051
§ 371 (c)(1),
(2) Date: Dec. 4, 2018

(87) PCT Pub. No.: WO2017/221795
PCT Pub. Date: Dec. 28, 2017

(65) Prior Publication Data
US 2020/0002744 A1  Jan. 2, 2020

(30) Foreign Application Priority Data

Jun. 22, 2016  (JP) ................ 2016-123707

(51) Int. Cl.
*C12Q 1/44* (2006.01)
*C12N 9/16* (2006.01)

(52) U.S. Cl.
CPC ........... *C12Q 1/44* (2013.01); *C12N 9/16* (2013.01); *C12Y 301/01004* (2013.01); *G01N 2333/92* (2013.01); *G01N 2800/323* (2013.01)

(58) Field of Classification Search
None
See application file for complete search history.

(56) References Cited

U.S. PATENT DOCUMENTS

| | | |
|---|---|---|
| 2005/0244913 A1 | 11/2005 | Shou et al. |
| 2007/0077614 A1 | 4/2007 | Wolfert et al. |
| 2013/0236450 A1 | 9/2013 | Montaner et al. |
| 2015/0160229 A1 | 6/2015 | Schaal et al. |
| 2016/0349271 A1 | 12/2016 | Zhuo et al. |

FOREIGN PATENT DOCUMENTS

| | | |
|---|---|---|
| JP | 04-346797 A | 12/1992 |
| JP | 05-168498 A | 7/1993 |
| JP | 07-059597 A | 3/1995 |
| JP | 08-000293 A | 1/1996 |
| JP | 2002-223794 A | 8/2002 |
| JP | 2004-159531 A | 6/2004 |
| JP | 2012-210179 A | 11/2012 |
| WO | 2004/089184 A2 | 10/2004 |
| WO | 2005/001416 A2 | 1/2005 |
| WO | 2005/113797 A2 | 12/2005 |
| WO | 2011/137419 A1 | 11/2011 |
| WO | 2014/010667 A1 | 1/2014 |
| WO | 2015/085314 A2 | 6/2015 |
| WO | 2015/123598 A1 | 8/2015 |

OTHER PUBLICATIONS

"Lp-PLA2 FS*: Diagnostic Reagent for Quantitative in Vitro Determination of Lp-PLA$_2$ (Lipoprotein-associated phospholipase A$_2$) in Serum and Plasma on Photometric Systems", DiaSys Diagnostic Systems GmbH, pp. 1-2 (Jul. 2015).
"PLAC Test for Lp-PLA$_2$ Activity", diaDexus, Inc., pp. 1-12 (2015).
Karabina et al., "Plasma PAFAH/PLA2G7 Genetic Variability, Cardiovascular Disease, and Clinical Trials", *The Enzymes*, vol. 38, pp. 145-155 (2015).
Stafforini, "Diverse Functions of Plasma PAF-AH in Tumorigenesis", *The Enzymes*, vol. 38, pp. 157-179 (2015).
Matsumoto, "Screening and Characterization of a Novel Lysoplasmalogen-specific Phospholipase D for the Application to a Diagnostic Reagent for Plasmalogen Determination", Abstract of Doctoral Thesis, along with an English language translation thereof (Jun. 23, 2015).
Matsumoto, "Screening and Characterization of a Novel Lysoplasmalogen-specific Phospholipase D for the Application to a Diagnostic Reagent for Plasmalogen Determination", Doctoral Thesis (Sep. 25, 2018) [retrieved from http://hdl.handle.net/10270/4262, Nov. 16, 2018], including screenshot from website and partial translation of screenshot evidence publication date.
Sugimori, "Novel Phospholipases of Bacteria", *Oleoscience*, vol. 13, No. 10, pp. 477-484 (2013), including an English-language Abstract.
International Search Report issued in PCT/JP2017/022051, dated Sep. 12, 2017, along with an English language translation.
International Preliminary Report on Patentability issued in PCT/JP2017/022051, dated Dec. 25, 2018, along with an English language translation.

*Primary Examiner* — Suzanne M Noakes
(74) *Attorney, Agent, or Firm* — Greenblum & Bernstein, P.L.C.

(57) ABSTRACT

An object of the present invention is to provide a highly versatile, simple and safe method for measuring Lp-PLA$_2$ activity. Another object of the present invention is to provide an accurate and highly sensitive method for measuring Lp-PLA$_2$ activity. Provided is a method for measuring lipoprotein-associated phospholipase A$_2$ (Lp-PLA$_2$) activity in a sample containing Lp-PLA$_2$, the method comprising the following steps (A) to (C):
(A) converting PAFs into lyso-PAFs by reacting the PAFs with the Lp-PLA$_2$ in the sample;
(B) hydrolyzing the lyso-PAFs produced in the step (A) with an enzyme (lyso-PAF-PLD) to obtain hydrolysate; and
(C) measuring Lp-PLA$_2$ activity in the sample by utilizing a quantitative change attributable to the hydrolysate obtained in step (B) as an indicator.

13 Claims, 7 Drawing Sheets
Specification includes a Sequence Listing.

[Fig. 1]
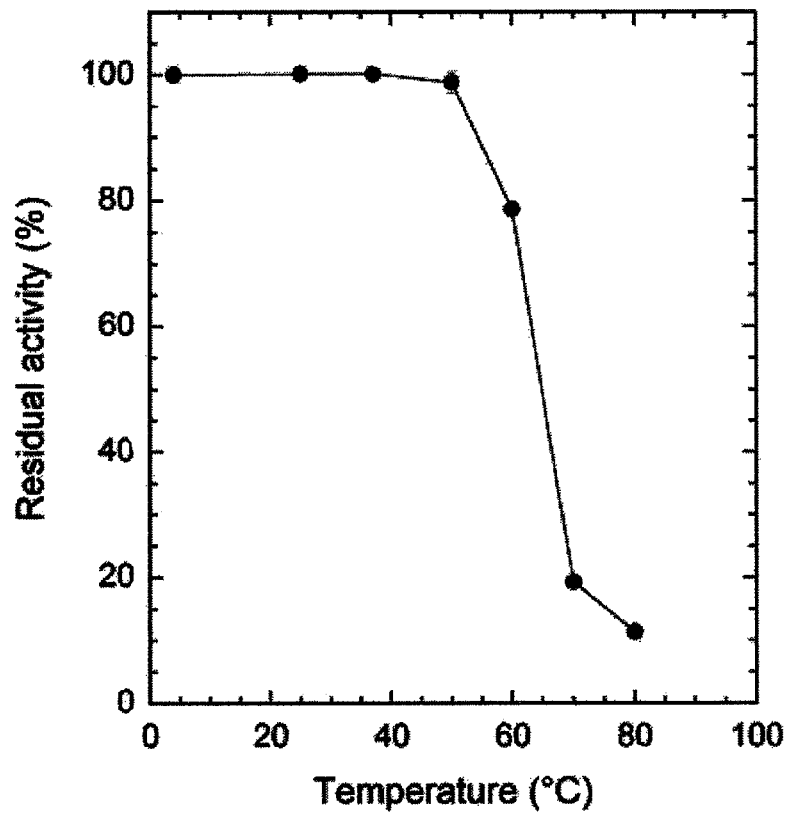
[Fig. 2]
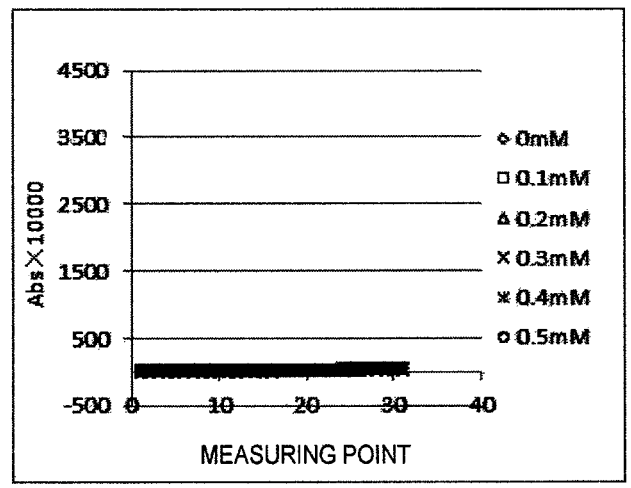

[Fig. 3]
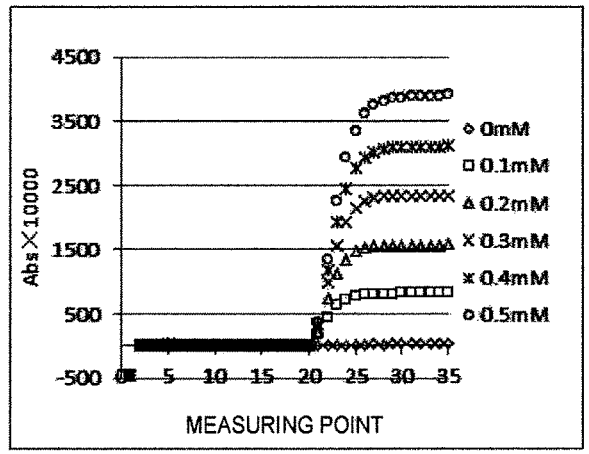
[Fig. 4]
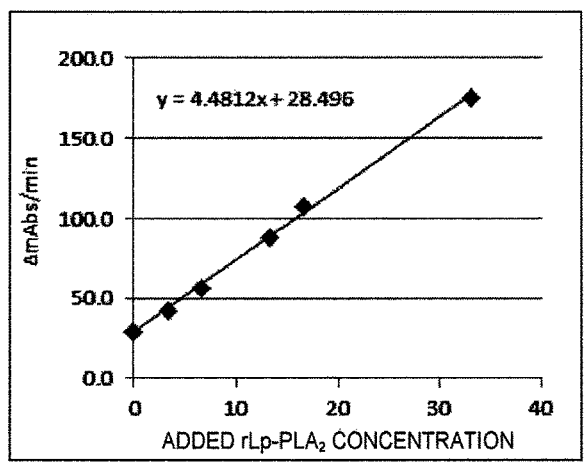
[Fig. 5]
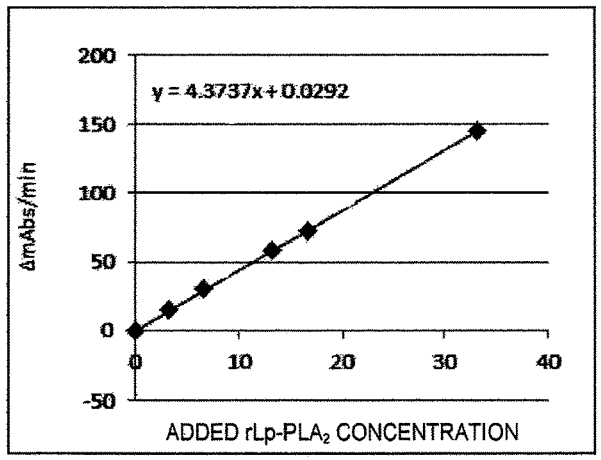

[Fig. 6]
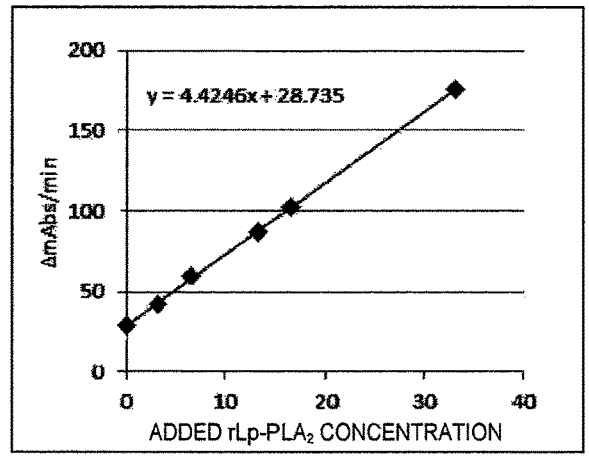
[Fig. 7]
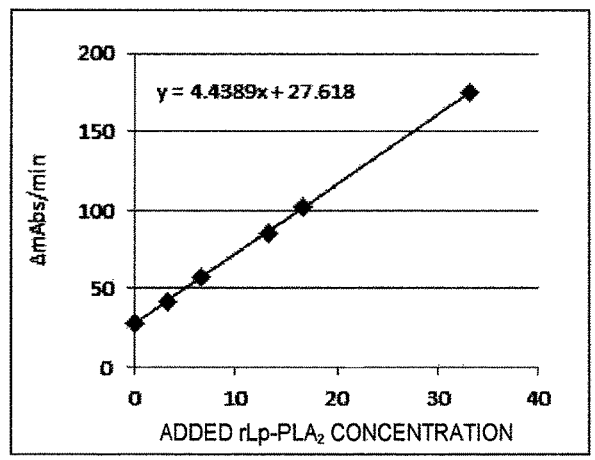
[Fig. 8]
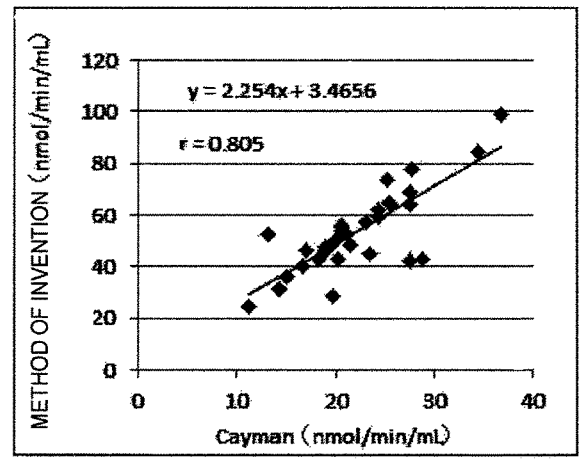

[Fig. 9]
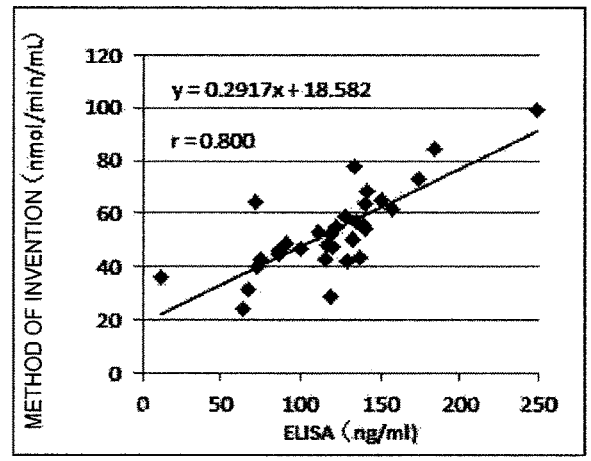
[Fig. 10]
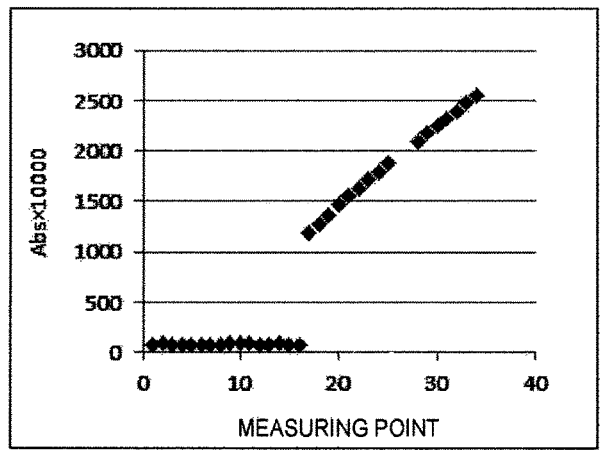
[Fig. 11]
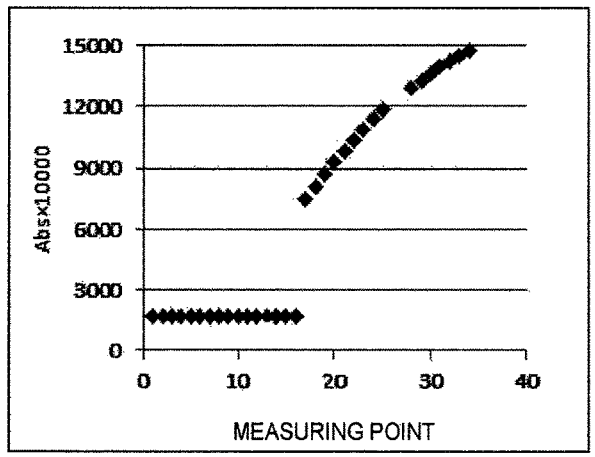

[Fig. 12]
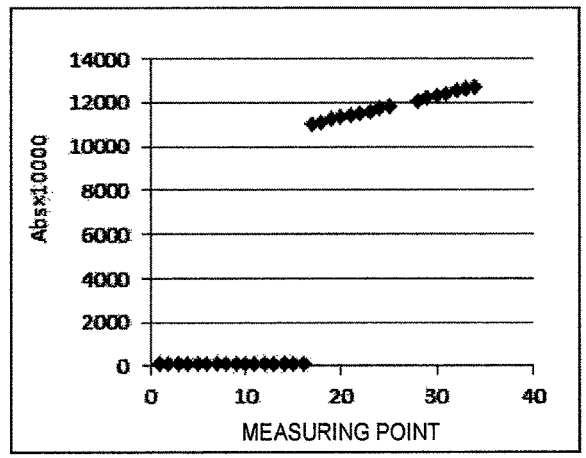
[Fig. 13]
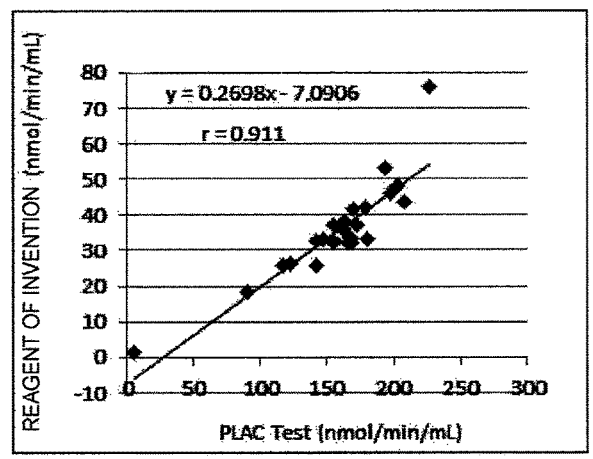
[Fig. 14]
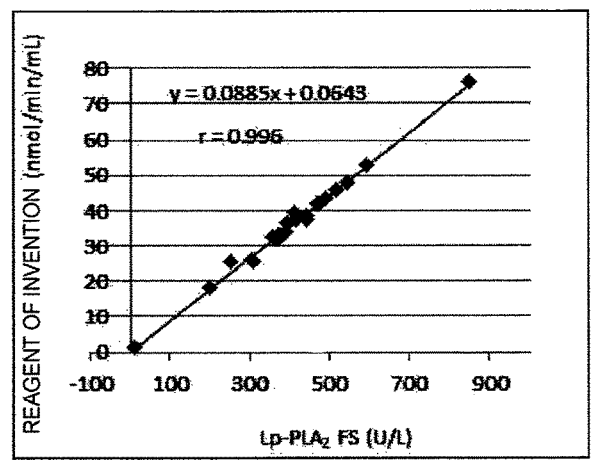

[Fig. 15]
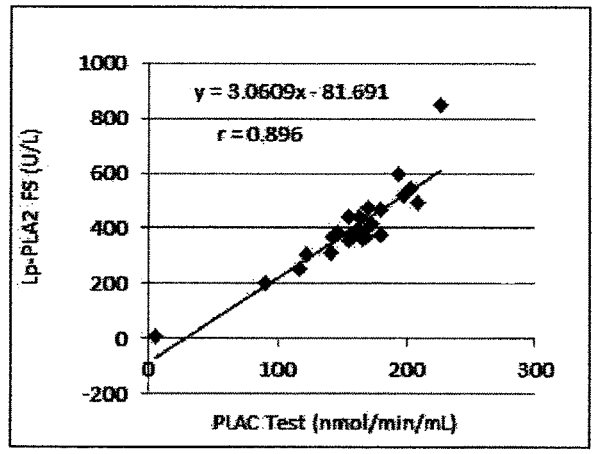
[Fig. 16]
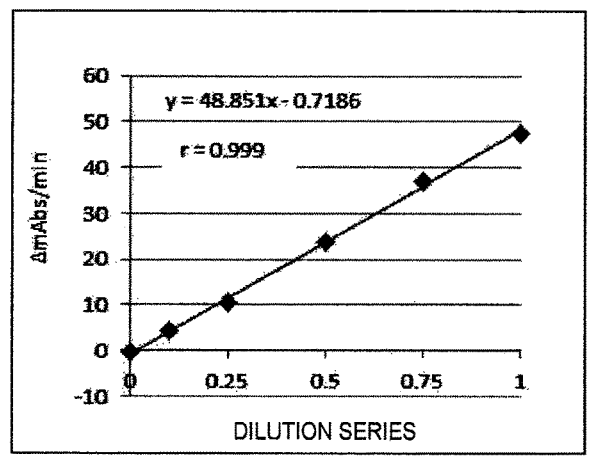
[Fig. 17]
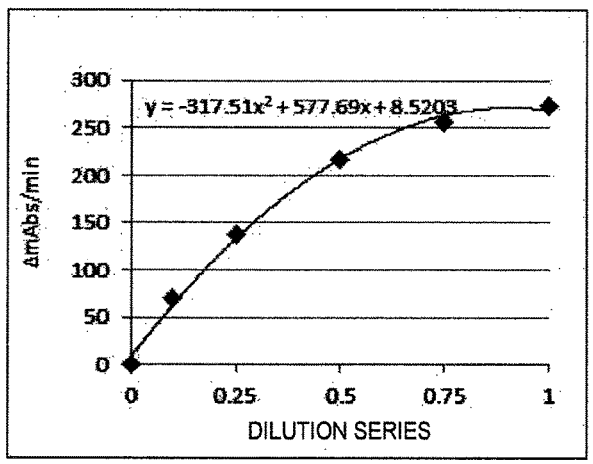

[Fig. 18]
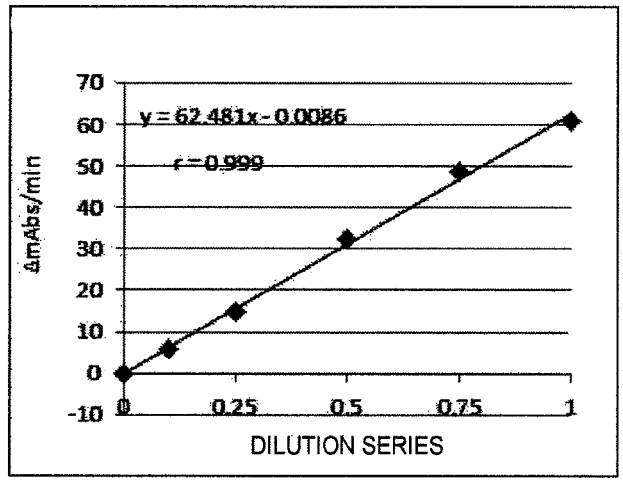
[Fig. 19]
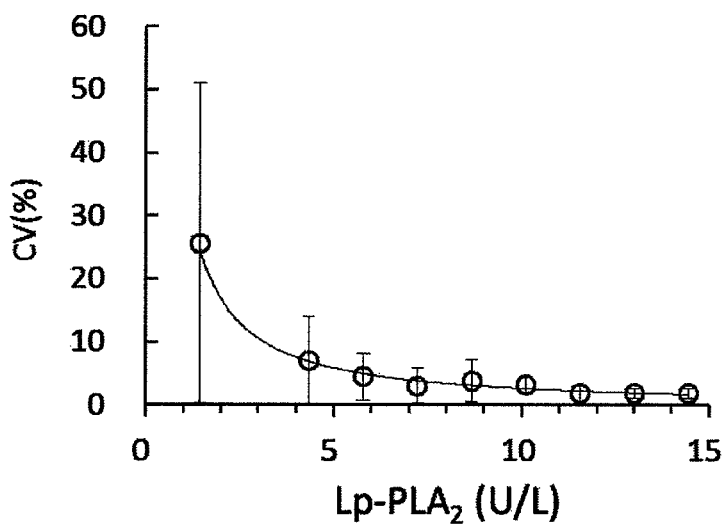

MEASUREMENT OF LP-PLA$_2$ ACTIVITY

SEQUENCE LISTING

The instant application contains a Sequence Listing which has been filed electronically in ASCII format and is hereby incorporated by reference in its entirety. Said ASCII copy, created on Feb. 27, 2019, is named P56540_SL.txt and is 12,600 bytes in size.

TECHNICAL FIELD

The present invention relates to a measurement method and kit for measuring Lp-PLA$_2$ activity as well as a use of the method and the kit.

BACKGROUND ART

Lipoprotein-associated phospholipase A2 (also known as platelet-activating factor acetylhydrolase (PAF-AH); hereunder called Lp-PLA$_2$) is an enzyme that inactivates platelet-activating factor (PAF) by hydrolyzing the acetyl group at the sn-2 position of PAF. Lp-PLA$_2$ is involved in the formation of unstable plaque in blood vessels, and Lp-PLA$_2$ activity has been used as a risk prediction marker for cardiovascular events caused by atherosclerosis (Non-Patent Document 1 and 2). In December of 2014, an Lp-PLA$_2$ activity measurement kit called the PLAC Test for Lp-PLA$_2$ Activity (Diazyme Laboratories, formerly diaDexus Inc.) was approved by the U.S. Food and Drug Administration (FDA) as one means of diagnosing the risk of coronary heart disease (CHD). Besides this kit, Diasys Lp-PLA$_2$ FS (Diasys) is also commercially available for in vitro diagnosis. In addition, there are demands for the Lp-PLA$_2$ activity measuring for research uses, and PAF Acetylhydrolase Assay Kit (Cayman Chemical Company) is commercially available as a research reagent.

Lp-PLA$_2$ is thought to be a factor in various diseases and inflammations. An association between Lp-PLA$_2$ and cancer has recently been suggested, and thus apart from its conventionally known association with cardiovascular disease, stroke and the like, Lp-PLA$_2$ activity could also be measured to predict the risk of cancer and the like (Non-Patent Document 1).

Methods using PAF labeled with a radioactive isotope are known as methods of measuring Lp-PLA$_2$ activity (Patent Document 1). Other methods of measuring Lp-PLA$_2$ activity include a method using a PAF derivative having a substituent that forms a chromogenic compound or fluorescent chromogenic compound when released (Patent Document 2), and methods of measuring the amounts of substituents released from PAF derivatives (Patent Documents 3 and 4).

CITATION LIST

Patent Document

Patent Document 1: WO 2005/001416
Patent Document 2: Patent Publication JP-A-2002-223794
Patent Document 3: Patent Publication JP-A-H07-59597
Patent Document 4: Patent Publication JP-A-H04-346797
Patent Document 5: WO 2014/010667

Non-Patent Document

Non-Patent Document 1: THE ENZYMES, Platelet-Activating Factor Acetylhydrolases (PAF-AH), (2015) Vol. 38, 145-179

Non-Patent Document 2: PLAC Test for Lp-PLA$_2$ Activity (diaDexus Co., package insert ver. 2015-01-15)

Non-Patent Document 3: Diasys Lp-PLA$_2$ FS (Diasys, package insert ver. July 2015/8)

SUMMARY

Technical Problem

However, the method of Patent Document 1 lacks versatility and is only used by a limited number of users and facilities. It is also difficult to measure multiple specimens simultaneously with this method, and there are problems of safety or disposal of radioactive reagents and the like.

Moreover, one of the PAF derivatives disclosed in Patent Document 2 is 1-myristoyl-2-(4-nitrophenylsuccinyl)phosphatidylcholine, which has poor water solubility at neutral pH values, and thus must be made into an acidic aqueous solution composition (Non-Patent Document 2 or 3) or an organic solvent composition (Non-Patent Document 3). When Lp-PLA$_2$ activity is measured using the acidic aqueous solution composition, the pH may vary due to carbon dioxide gas in the air.

The method disclosed in Patent Document 4 uses DTNB (5,5'-dithiobis(2-nitrobenzoic acid)) as an SH group detection reagent, and therefore it has a low specificity due to the interference substances having SH groups that are contained in serum. The measurement methods of Patent Documents 3 and 4 also have high S/R (sample/reagent) ratios, or use large-volume samples.

A problem to be solved by the present invention is to provide a more versatile, simple and safe method for measuring Lp-PLA$_2$ activity. Another object of the present invention is to provide an accurate method for measuring Lp-PLA$_2$ activity. Yet another object of the present invention is to provide a highly sensitive method for measuring Lp-PLA$_2$ activity.

Solution to Problem

The inventors previously discovered an enzyme that acts on ethanolamine lysoplasmalogen (a protein having the amino acid sequence represented by SEQ ID NO: 2 and a protein encoded by the nucleotide sequence of SEQ ID NO: 4 in Patent Document 5, described as lyPlsase from *Thermocrispum* sp. NITE BP-01628; also called "lyso-PAF-PLD" below). The inventors also discovered as a result of exhaustive research aimed at solving the aforementioned problems that lyso-PAF-PLD has PLD activity against lyso-PAF but no PLD activity (phospholipase D-like activity) against PAF in environments containing both PAF and lyso-PAF, and that this substrate specificity is useful for measuring Lp-PLA$_2$ activity, thereby reaching the present invention.

That is, the present invention includes the following.

[1'] Use of an enzyme in the presence of platelet-activating factors (PAFs) represented by General Formula I below:

[Chemical formula 1]

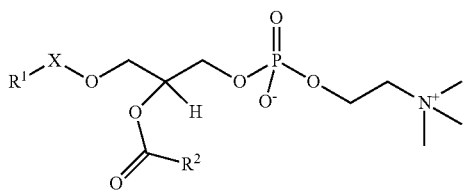
(I)

wherein:
R¹ is a linear or branched, saturated or partially unsaturated higher hydrocarbon group;
R² is a linear lower alkyl group; and
X is —C(O)—, —CH₂— or —CH=CH—,
and
lyso-PAFs represented by General Formula II below:

[Chemical formula 2]

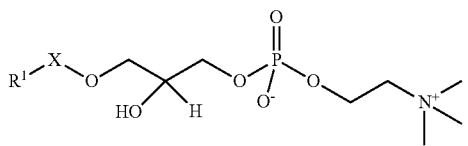
(II)

where R¹ and X are defined as in General Formula I, to thereby produce choline by hydrolysis of the lyso-PAFs without producing choline by hydrolysis of the PAFs, wherein
the enzyme is a protein according to any of (a) to (c) below:
(a) a protein having an amino acid sequence represented by SEQ ID NO: 1 or 9;
(b) a protein having an amino acid sequence represented by SEQ ID NO: 1 or 9 with one or more amino acids deleted, substituted or added therein, and having phospholipase D-like (PLD) activity against lyso-PAF but no PLD activity against PAF; or
(c) a protein having an amino acid sequence having at least 90% sequence identity with an amino acid sequence according to SEQ ID NO: 1 or 9, and having PLD activity against lyso-PAF but no PLD activity against PAF.

[1"] Use of an enzyme in the measurement of a lyso-platelet-activating factors (lyso-PAFs) in a sample that may contain PAFs represented by General Formula I below:

[Chemical formula 3]

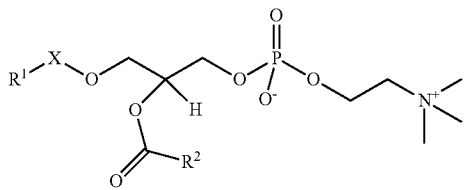
(I)

wherein:
R¹ is a linear or branched, saturated or partially unsaturated higher hydrocarbon group;
R² is a linear lower alkyl group; and
X is —C(O)—, —CH₂— or —CH=CH—,
and the lyso-PAFs are represented by General Formula II below:

[Chemical formula 4]

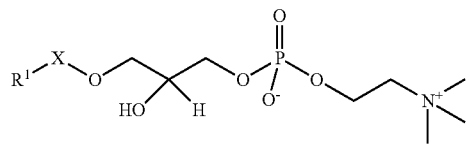
(II)

where R¹ and X are defined as in General Formula I, to thereby produce choline by hydrolysis of the lyso-PAFs without producing choline by hydrolysis of the PAFs, wherein the enzyme is a protein according to any of (a) to (c) below:
(a) a protein having an amino acid sequence represented by SEQ ID NO: 1 or 9;
(b) a protein having an amino acid sequence represented by SEQ ID NO: 1 or 9 with one or more amino acids deleted, substituted or added therein, and having phospholipase D-like (PLD) activity against lyso-PAF but no PLD activity against PAF; or
(c) a protein having an amino acid sequence having at least 90% sequence identity with an amino acid sequence represented by SEQ ID NO: 1 or 9, and having PLD activity against lyso-PAF but no PLD activity against PAF.

[1'''] Use of an enzyme to measure the activity of an enzyme that converts platelet-activating factors (PAFs) represented by General Formula I below:

[Chemical formula 5]

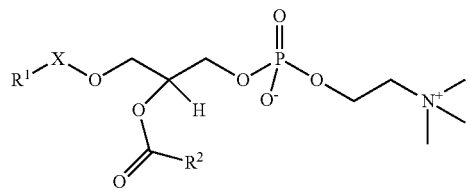
(I)

wherein:
R¹ is a linear or branched, saturated or partially unsaturated higher hydrocarbon group;
R² is a linear lower alkyl group; and
X is —C(O)—, —CH₂— or —CH=CH—,
into lyso-PAFs represented by General Formula II below:

[Chemical formula 6]

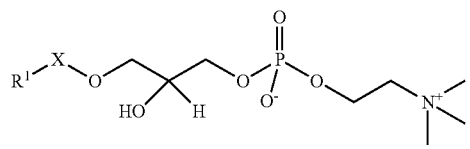
(II)

wherein $R^1$ and X are defined as in General Formula I, to thereby produce choline by hydrolysis of the lyso-PAFs without producing choline by hydrolysis of the PAFs in a sample that may contain the PAFs, wherein the enzyme used is a protein according to any of (a) to (c) below:

(a) a protein having an amino acid sequence represented by SEQ ID NO: 1 or 9;

(b) a protein having an amino acid sequence represented by SEQ ID NO: 1 or 9 with one or more amino acids deleted, substituted or added therein, and having phospholipase D-like (PLD) activity against lyso-PAF but no PLD activity against PAF; or (c) a protein having an amino acid sequence having at least 90% sequence identity with an amino acid sequence represented by SEQ ID NO: 1 or 9, and having PLD activity against lyso-PAF but no PLD activity against PAF.

The present invention also includes the following. As used below, [1] encompasses all of [1'], [1"] and [1'"] above.

[1-1] The use according to [1], wherein the enzyme is a protein according to any of (d) to (f) below:

(d) a protein having an amino acid sequence encoded by the nucleotide sequence of SEQ ID NO: 2;

(e) a protein having an amino acid sequence encoded by the nucleotide sequence of SEQ ID NO: 2 with one or more nucleotides deleted, substituted or added therein, and having PLD activity against lyso-PAF but no PLD activity against PAF; or (f) a protein having an amino acid sequence encoded by a nucleotide sequence having at least 90% sequence identity with the nucleotide sequence of SEQ ID NO: 2, and having PLD activity against lyso-PAF but no PLD activity against PAF.

[1-2] The use according to [1] or [1-1], wherein $R^2$ is a methyl group.

[1-3] The use according to any one of [1] to [1-2], wherein $R^1$ is independently selected from $C_{15}$ and $C_{17}$ linear alkyl groups.

[1-4] The use according to any one of [1] to [1-3], wherein X is —$CH_2$—.

[1-5] The use according to any one of [1] to [1-3], wherein X is —C(O)—.

[1-6] The use according to any one of [1] to [1-5], wherein the use of [1] is a use of an enzyme that is a protein according to any of (a) to (c) to measure the lyso-PAFs represented by the General Formula II when contamination by the PAFs represented by the General Formula I is possible.

[2] A method for measuring lipoprotein-associated phospholipase A2 ($Lp\text{-}PLA_2$) activity in a sample containing $Lp\text{-}PLA_2$, the method including the following steps (A) to (C):

(A) converting platelet-activating factors (PAFs) represented by General Formula I below:

[Chemical formula 7]

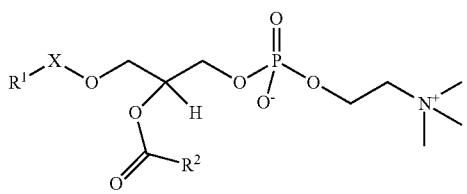

(I)

wherein:
$R^1$ is a linear or branched, saturated or partially unsaturated higher hydrocarbon group;
$R^2$ is a linear lower alkyl group; and
X is —C(O)—, —$CH_2$— or —CH=CH—, into lyso-PAFs represented by General Formula II below:

[Chemical formula 8]

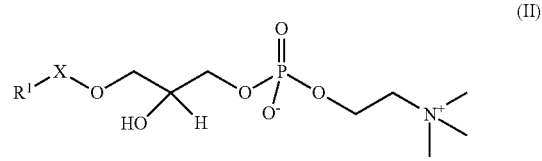

(II)

wherein $R^1$ and X are defined as in General Formula I, by reacting the PAFs with the $Lp\text{-}PLA_2$ in the sample;

(B) hydrolyzing the lyso-PAFs produced in the step (A) with an enzyme that is a protein according to any of (a) to (c) below to obtain hydrolysate:

(a) a protein having an amino acid sequence represented by SEQ ID NO: 1 or 9, (b) a protein having an amino acid sequence represented by SEQ ID NO: 1 or 9 with one or more amino acids deleted, substituted or added therein, and having phospholipase D-like (PLD) activity against lyso-PAF but no PLD activity against PAF, or (c) a protein having an amino acid sequence having at least 90% sequence identity with an amino acid sequence represented by SEQ ID NO: 1 or 9, and having PLD activity against lyso-PAF but no PLD activity against PAF; and (C) measuring $Lp\text{-}PLA_2$ activity in the sample by utilizing a quantitative change attributable to the hydrolysate obtained in step (B) as an indicator.

[3] The method according to [2], wherein the quantitative change in step (C) is a change in the amount of hydrolysate choline.

[3-1] The method according to [2], wherein in the quantitative change in step (C) is a change in the amount of lyso-PAF decholinates, which are hydrolysates.

[4] The method according to [3], wherein the step (C) also comprises a following step (C-1) as a method of measuring the change in the amount of choline:

(C-1) reacting choline with choline oxidase to produce hydrogen peroxide.

[5] The method according to [4], wherein the step (C) also comprises a following step (C-2):

(C-2) measuring the amount of hydrogen peroxide produced in the step (C-1) by a colorimetric method using a chromogenic reagent.

[6] The method according to any one of [2] to [5], further comprising a following step (D) prior to the step (A):

(D) removing the choline in the sample.

[7] The method according to [6], wherein the step (D) is removing the choline in the sample by utilizing choline oxidase.

[8] The method according to any one of [2] to [7], wherein $R^2$ is a methyl group.

[9] The method according to any one of [2] to [8], wherein $R^1$ is independently selected from $C_{15}$ and $C_{17}$ linear alkyl groups.

[10] The method according to any one of [2] to [9], wherein X is —$CH_2$—.

[11] The method according to any one of [2] to [9], wherein X is —C(O)—.

[12] A kit for measuring lipoprotein-associated phospholipase A2 (Lp-PLA$_2$) activity in a sample,
the kit comprising:
an enzyme that is a protein according to any of (a) to (c) below:
(a) a protein having an amino acid sequence represented by SEQ ID NO: 1 or 9;
(b) a protein having an amino acid sequence represented by SEQ ID NO: 1 or 9 with one or more amino acids deleted, substituted or added therein, and having phospholipase D-like (PLD) activity against lyso-platelet-activating factor (PAF) but no PLD activity against a PAF; or
(c) a protein having an amino acid sequence having at least 90% sequence identity with an amino acid sequence represented by SEQ ID NO: 1 or 9, and having PLD activity against lyso-PAF but no PLD activity against PAF; and
PAFs represented by General Formula I below:

[Chemical formula 9]

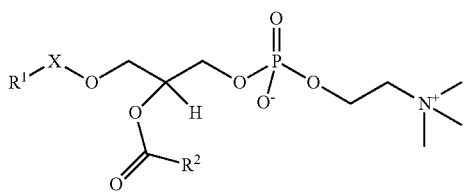

(I)

wherein:
R$^1$ is a linear or branched, saturated or partially unsaturated higher hydrocarbon group;
R$^2$ is a linear lower alkyl group; and
X is —C(O)—, —CH$_2$— or —CH═CH—.
[13] The kit according to [12], further comprising a choline oxidase. [14] The kit according to [13], further comprising a peroxidase, a Trinder reagent and a coupler.
[14-1] The kit according to [13], also comprising a peroxidase and a chromogenic reagent.
[14-2] The kit according to [14-1], wherein the chromogenic reagent is either a leuco-type reagent or a coupler and a Trinder reagent.
[14-3] The kit according to [14-1], wherein the chromogenic reagent is a coupler and a Trinder reagent.
[14-4] The kit according to [14-3], wherein the coupler is 4-aminoantipyrine.
[15] The kit according to any one of [12] to [14-4], comprising: a first reagent comprising the enzyme; and a second reagent comprising the PAFs.
[16] The kit according to [15], wherein the first reagent also comprises a choline oxidase.
[16-1] The kit according to [15] or [16], wherein the first reagent and/or the second reagent also comprises a chromogenic reagent.
[16-2] The kit according to any one of [12] to [16-1], wherein the contents are stored separately in multiple containers.
[16-3] The kit according to any one of [12] to [16-2], wherein R$^2$ is a methyl group.
[16-4] The kit according to any one of [12] to [16-3], wherein R$^1$ is independently selected from C$_{15}$ or C$_{17}$ linear alkyl groups.
[16-5] The kit according to any one of [12] to [16-4], wherein X is —CH$_2$—.
[16-6] The kit according to any one of [12] to [16-4] wherein X is —C(O)—.

[17] A method for diagnosing and/or managing a disease and/or condition associated with Lp-PLA$_2$, the method comprising measuring Lp-PLA$_2$ activity in a sample from a subject by using the kit according to any one of [12] to [16-6].
[18] The method according to [17], wherein the disease and/or condition associated with Lp-PLA$_2$ is cardiovascular disease related to atherosclerosis.
[19] The kit according to any one of [12] to [16-6], which is a kit for diagnosing a disease and/or condition associated with Lp-PLA$_2$.
[20] The kit according to [19], wherein the disease and/or condition associated with Lp-PLA$_2$ is cardiovascular disease related to atherosclerosis.

Advantageous Effects of Invention

Easier, safer and more versatile measurement of Lp-PLA$_2$ activity is possible with the present invention. Lp-PLA$_2$ activity can also be measured accurately or with a high degree of sensitivity, while minimizing the effects of interferences. The present invention is also useful for diagnosing and managing diseases or conditions associated with Lp-PLA$_2$, such as atherosclerosis.

BRIEF DESCRIPTION OF DRAWINGS

FIG. 1 shows residual lyso-PAF-PLD activity at different temperatures as measured in Reference Example 10.
FIG. 2 shows absorbance changes at each measuring point during a 10-minute reaction time using PAF as a substrate in various concentrations in Example 1.
FIG. 3 shows absorbance changes at each measuring point during a 10-minute reaction time using lyso-PAF as a substrate in various concentrations in Example 1.
FIG. 4 shows absorbance changes after addition of various concentrations of rLp-PLA$_2$ to pooled serum J042 in Example 14.
FIG. 5 shows absorbance changes after addition of various concentrations of rLp-PLA$_2$ to pooled serum A in Example 14.
FIG. 6 shows absorbance changes after addition of various concentrations of rLp-PLA$_2$ to pooled serum B in Example 14.
FIG. 7 shows absorbance changes after addition of various concentrations of rLp-PLA$_2$ to pooled serum C in Example 14.
FIG. 8 shows a correlation of Lp-PLA$_2$ activity measurements obtained with the reagents of the invention and a Cayman Chemical Company reagent in Example 15.
FIG. 9 shows a correlation of Lp-PLA$_2$ activity measurements obtained with the reagents of the invention and an R&D Systems ELISA kit in Example 16.
FIG. 10 shows a reaction time course of the pooled serum J042 with the reagents of the invention in Example 18.
FIG. 11 shows a reaction time course of the pooled serum J042 with PLAC Test in Example 18.
FIG. 12 shows a reaction time course of the pooled serum J042 with Lp-PLA$_2$ FS in Example 18.
FIG. 13 shows a correlation of Lp-PLA$_2$ activity measurements obtained with the reagents of the invention and PLAC Test in Example 20.
FIG. 14 shows a correlation of Lp-PLA$_2$ activity measurements obtained with Lp-PLA$_2$ FS and the reagents of the invention in Example 20.

FIG. 15 shows a correlation of Lp-PLA$_2$ activity measurements obtained with PLAC Test and Lp-PLA$_2$ FS in Example 20.

FIG. 16 shows a dilution linearity of Lp-PLA$_2$ activity measurements obtained with the reagents of the invention in Example 21.

FIG. 17 shows a dilution linearity of Lp-PLA$_2$ activity measurements obtained with PLAC Test in Example 21.

FIG. 18 shows a dilution linearity of Lp-PLA$_2$ activity measurements obtained with Lp-PLA$_2$ FS in Example 21.

FIG. 19 is a graph showing coefficients of variation (CV %) calculated from the Lp-PLA$_2$ concentrations measured in Example 26 as white circles, and the 2SDs (2× standard deviations) as error bars; and the Lp-PLA$_2$ concentrations and coefficients of variation are power-approximated and shown as a solid line (y=37.644x$^{-1.155}$).

DESCRIPTION OF EMBODIMENTS

The present invention is explained in detail below based on embodiments of the invention (hereunder sometimes called "the present embodiment"). The present embodiments below are intended to exemplify the invention and not to limit its scope.

As used herein, a carbon atom may be represented simply as "C", a hydrogen atom as "H", an oxygen atom as "O", a nitrogen atom as "N" and a phosphorus atom as "P". A carbonyl group may similarly be represented simply as "—C(O)—", and an ether bond as "—O—", in which "—" represents a bond. A double bond may be represented simply as "=".

A hydrocarbon group is a molecular group remaining after removal of one or two or more hydrogen atoms from a hydrocarbon, and may be either linear or branched, and may also be partially unsaturated. In the specification and the claims, the terms "higher" and "lower" refer to numbers of carbon atoms, and the ranges thereof can be easily understood by a person skilled in the art. For example, a higher hydrocarbon group may have 10 to 30, or preferably 10 to 20, or more preferably 15 to 17 carbon atoms. A lower hydrocarbon may have 1 to 9 or preferably 1 to 4 carbon atoms, or more preferably 1 carbon atom.

An "alkyl" as used herein is a linear or branched saturated hydrocarbon group.

As used herein, the number of carbon atoms in a hydrocarbon moiety is represented as "C$_p$", meaning that the number of carbon atoms is p.

One aspect of the present embodiments provides the use of a specific enzyme in the presence of platelet-activating factors (PAFs) and lyso-PAFs to produce choline by hydrolysis of the lyso-PAFs without performing a reaction to produce choline by hydrolysis of the PAFs. Moreover, one aspect of the present embodiments provides a method for measuring the concentration of lyso-PAFs using as an indicator a change in the amount of hydrolysate obtained by hydrolyzing the lyso-PAFs with a specific enzyme.

One aspect of the present embodiments also provides a method for measuring lipoprotein-associated phospholipase A2 (Lp-PLA$_2$) activity in a sample containing Lp-PLA$_2$, comprising the following steps (A) to (C):

(A) converting PAFs into lyso-PAFs by reacting the PAFs with Lp-PLA$_2$ in the sample;

(B) hydrolyzing the lyso-PAFs produced in the step (A) with a specific enzyme to obtain the hydrolysate; and (C) measuring Lp-PLA$_2$ activity in the sample by utilizing a quantitative change attributable to the hydrolysate obtained in step (B) as an indicator.

In one aspect of the present embodiments, the reaction system for Lp-PLA$_2$ activity measurement is represented by the following scheme.

[Chemical formula 10]

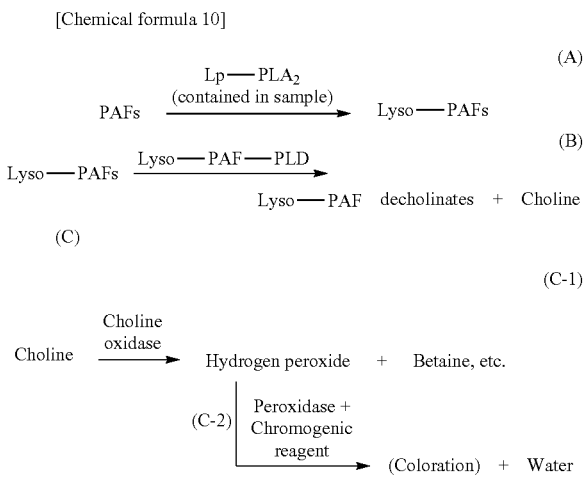

In one aspect of the present embodiments, the step (A) can be performed by, for example, mixing a sample containing Lp-PLA$_2$ with a reagent containing PAF as shown in the following examples.

In the present embodiment, a "sample" is measurement object, and a "sample" in which Lp-PLA$_2$ activity can be measured may be any which contains or may contain Lp-PLA$_2$, without any particular limitations. Examples of such samples include bodily fluids such as blood, serum, plasma, urine or amniotic fluid from humans or animals, and cells, organs, or extracts of cells and organs from humans or animals. A sample is preferably blood, serum or plasma from a human. As described in Examples 24 and 25 below, with the present embodiment it is possible to measure Lp-PLA$_2$ activity stably and with high sensitivity even after a sample has been stored at a normal specimen storage temperature range (such as room temperature (1° C. to 30° C.)) or in a deep freezer at a lower temperature (down to −80° C.).

In the present embodiment, Lp-PLA$_2$ (lipoprotein-associated phospholipase A$_2$) is an enzyme that at least hydrolyzes the acetyl group at the sn-2 position of a PAF, to thereby produce lyso-PAF and inactivate PAF. It is also called platelet-activating factor acetylhydrolase (PAF-AH).

In the present embodiment, the platelet-activating factors (PAFs) are represented by the following General Formula I.

[Chemical formula 11]

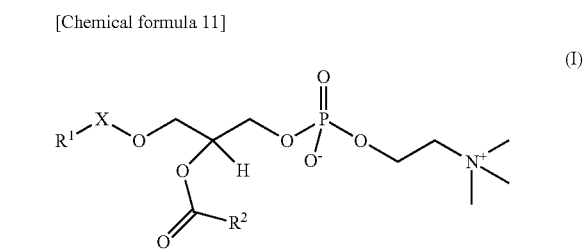

In the General Formula I, R$^1$ is a linear or branched, saturated or partially unsaturated higher hydrocarbon group, and may be a C$_{10\text{-}30}$ hydrocarbon group, or preferably a C$_{10\text{-}20}$ hydrocarbon group, or more preferably a C$_{15\text{-}17}$ hydrocarbon group. In one embodiment, it may be a C$_{10}$ or higher linear alkyl group, or preferably a $C_{15}$ linear alkyl group or $C_{17}$ linear alkyl group, or more preferably a $C_{15}$ linear alkyl group. In one embodiment, $R^1$ may be a partially unsaturated hydrocarbon group. When unsaturated bonds are present, the number thereof is preferably 1 or 2, or more preferably 1. Examples of partially unsaturated $R^1$ groups include geranyl, geranylgeranyl and oleyl groups and the like.

$R^2$ in the General Formula I is a linear lower alkyl group, such as a $C_{1-9}$ alkyl group. The smaller the molecule of $R^2$ in the General Formula I, the better it is as the substrate for Lp-$PLA_2$ (Journal of Clinical Laboratory Medicine, February 2012, Vol. 56, No. 2, p. 152), so $R^2$ in one embodiment is preferably a $C_{1-4}$ alkyl group, or more preferably a methyl group or butyl group, or still more preferably a methyl group.

In the General Formula I, X is —C(O)—, —$CH_2$— or —CH═CH—, and is preferably —$CH_2$— in one embodiment, and still more preferably —C(O)— in another embodiment. In one embodiment, when X is —C(O)—, $R^1$ is preferably a $C_{15}$ linear alkyl (such as 1-palmitoyl-2-acetyl-sn-glycero-3-PC described below), while when X is —$CH_2$—, $R_1$ is preferably a $C_{15}$ or $C_{17}$ linear alkyl. When X is —CH═CH—, it may be either cis-form or trans-form, and is preferably trans-form.

In the present embodiment, "PAFs" is a general term for the PAF and PAF analogs explained below, and may refer to naturally occurring PAFs or artificially synthesized PAFs, including PAFs of which stereochemistry is S-configuration and R-configuration and mixtures of these in any proportions. In one aspect of the present embodiment, an optically active form of PAFs may be desirable from the standpoint of Lp-$PLA_2$ activity measurement sensitivity, while in other cases racemic PAFs may be desirable for economic reasons, such as manufacturing costs.

In the present embodiment, a "PAF" is a compound of General Formula I in which X is —$CH_2$—, $R^1$ is a $C_{15}$ or $C_{17}$ linear alkyl group and $R^2$ is a methyl group (these are sometimes called "PAF (C16)" or "PAF (C18)" respectively), and may be a naturally occurring PAF or an artificially synthesized PAF, including PAF of which stereochemistry is S-configuration and R-configuration and mixtures of these in any proportions.

In the present embodiment, "PAF analogs" are PAFs as defined by the General Formula I other than the PAF described above, and may be a naturally occurring PAF analog or an artificially synthesized PAF analog, including PAF analog of which stereochemistry is S-configuration and R-configuration and mixtures of these in any proportions. An example of a "PAF analog" is a plasmalogen. A plasmalogen may be a naturally occurring plasmalogen or an artificially synthesized plasmalogen, including mixtures of the optically active forms in any proportions when such exist. An example of such a plasmalogen is the plasmalogen described in Advances in Clinical Chemistry 2016, Vol. 38, pp. 109-116 for example. In one embodiment, when the PAFs are plasmalogens, $R^2$ is preferably a methyl group or butyl group.

PAFs can be obtained for example from Avanti Polar Lipids, Inc. (Alabama, USA) and Bachem (Switzerland). Optically active forms of PAFs can be synthesized by the methods disclosed in J. Org. Chem. 1995, Vol. 60, 7706-7708. Racemic PAFs can be synthesized by the methods disclosed in J. Org. Chem. 1995, Vol. 60, 7706-7708, using 1-O-hexadecyl-rac-glycerol as a starting material.

In the step (A) of the present embodiment, the amount of the PAFs used may be any amount that allows Lp-$PLA_2$ activity to be measured quantitatively, semi-quantitatively or qualitatively, and is preferably an amount that allows quantitative measurement. The lower limit may be at least 1 mM, or preferably at least 5 mM, or more preferably at least 7 mM, and the upper limit is not particularly limited but is preferably not more than 50 mM, or more preferably not more than 20 mM, or especially not more than 15 mM.

In the present embodiment, "lyso-PAFs" are compounds produced by hydrolysis of the sn-2 position of the PAFs described above, and are compounds represented by the following General Formula II:

[Chemical formula 12]

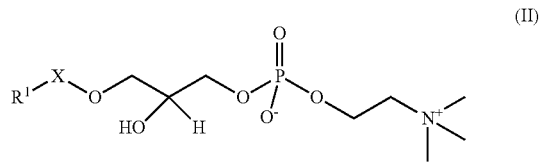

(II)

where $R^1$ and X are as defined in the General Formula I. "Lyso-PAFs" is a general term for the lyso-PAF and lyso-PAF analogs explained below.

In the present embodiment, a "lyso-PAF" is a compound of the General Formula II in which X is —$CH_2$— and $R^1$ is a $C_{15}$ or $C_{17}$ linear alkyl group, and may be either a naturally occurring lyso-PAF or an artificially synthesized lyso-PAF, including lyso-PAF of which stereochemistry is S-configuration and R-configuration and mixtures of these in any proportions. The lyso-PAF may also be produced within the reaction system.

In the present embodiment, "lyso-PAF analogs" are lyso-PAFs defined by the General Formula II other than the lyso-PAF described above, and may be a naturally occurring lyso-PAF analogs or an artificially synthesized lyso-PAF analogs, including lyso-PAF analogs of which stereochemistry is S-form and R-form and mixtures of these in any proportions. The lyso-PAF analogs may also be produced within the reaction system.

In one aspect of the present embodiment, as shown in the following examples for example, the step (B) can be performed by bringing together the lyso-PAFs produced from PAFs by Lp-$PLA_2$ in step (A) and a reagent containing an enzyme for producing choline by hydrolysis of this lyso-PAFs.

In one embodiment, the enzyme used in the step (B) is one of the following proteins:

(a) a protein having an amino acid sequence represented by SEQ ID NO: 1 or 9;

(b) a protein having an amino acid sequence represented by SEQ ID NO: 1 or 9 with one or more amino acids deleted, substituted or added therein, and having phospholipase D-like (PLD) activity against lyso-PAF but no PLD activity against PAF; or (c) a protein having an amino acid sequence having at least 90% sequence identity with the amino acid sequence of SEQ ID NO: 1 or 9, and having PLD activity against lyso-PAF but no PLD activity against PAF.

In one embodiment, the enzyme used in the step (B) may also be one of the following proteins:

(d) a protein having an amino acid sequence encoded by the nucleotide sequence of SEQ ID NO:2;

(e) a protein having an amino acid sequence encoded by the nucleotide sequence of SEQ ID NO:2 with one or more nucleotides deleted, substituted or added therein, and having PLD activity against lyso-PAF but no PLD activity against PAF; or (f) a protein having an amino acid sequence encoded by a nucleotide sequence having at least 90% sequence identity with the nucleotide sequence of SEQ ID NO: 2, and having PLD activity against lyso-PAF but no PLD activity against PAF.

In the protein of (b) above, the "amino acid sequence . . . with one or more amino acids deleted, substituted or added therein" is not particularly limited as long as the protein has the desired activity, but may for example be an amino acid sequence from which 1 or more, or more specifically 1 to 9, or preferably 1 to 5, or more preferably 1 to 3 amino acids have been deleted or the like.

Similarly, in the protein of (e) above, the "nucleotide sequence . . . with one or more nucleotides deleted, substituted or added therein" is not particularly limited as long as the encoded protein has the desired activity, but may for example be a nucleotide sequence from which 1 or more, or more specifically 1 to 9, or preferably 1 to 5, or more preferably 1 to 3 nucleotides have been deleted or the like.

In the protein of (c) above, the "amino acid sequence having at least 90% sequence identity with the amino acid sequence of SEQ ID NO: 1" is not particularly limited as long as the protein has the desired activity, but is for example an amino acid sequence having at least 92%, or preferably at least 95%, or more preferably at least 98%, or still more preferably at least 99% sequence identity.

Similarly, in the protein of (f) above, the "nucleotide sequence having at least 90% sequence identity with the nucleotide sequence of SEQ ID NO: 2" is not particularly limited, but is for example a nucleotide sequence having at least 92%, or preferably at least 95%, or more preferably at least 98%, or still more preferably at least 99% sequence identity.

A protein of (a) to (f) above may also have an N-terminally and/or C-terminally added part comprising a non-functional amino acid sequence such as a linker together with a functional peptide or tag, such as: a SEC or TAT signal peptide for transporting the enzyme of the present embodiment extracellularly or to the periplasm; a histidine tag for efficient purification; an affinity tag such as a Strep tag, TARGET tag or FLAG tag; a maltose binding protein tag, thioredoxin protein tag or glutathione-S-transferase tag for avoiding aggregation of the expressed protein; a TEE tag for increasing the expressed amount of the protein; or a GFP tag or the like as a marker. These amino acid sequences may be added serially, or added by disposing several protease-recognized amino acid sequences between each amino acid sequence or the like. These amino acid sequences (tags for example) may have all or part thereof deleted for the purpose of maximizing the function of the enzyme of the present embodiment or the like. In one embodiment, the proteins of (a) to (f) above are obtained by adding the amino acid sequences of the aforementioned signal peptides and the like to the amino acid sequence of SEQ ID NO: 9 or an amino acid sequence obtained by deleting, substituting or adding one or more amino acids in the amino acid sequence of SEQ ID NO: 9.

Examples of preferred signal peptides in the present embodiment include OmpT and PelB and the like, the *E. coli* TAT and SEC signal peptides described in J. Biol. Chem. 2007, Vol. 282, pp. 8309-8316 and Recent Patents on Biotechnology 2010, Vol 4, pp. 23-29, and the sequence of amino acids of 1st to $25^{th}$ positions in SEQ ID NO: 1.

In the present embodiment, the proteins of (a) to (f) above are sometimes called "lyso-PAF-PLDs". A "lyso-PAF-PLD" can be prepared for example according to the methods described in Patent Document 5, and specifically, as shown in Reference Examples 1 to 3 below for example, it can be prepared by a method that includes a step of culturing in medium a microorganism containing a gene encoding the amino acid sequence of SEQ ID NO: 1 or 9 or a gene having the nucleotide sequence of SEQ ID NO: 2, or a transformant transformed with a recombinant vector containing that gene, a step of producing and accumulating the lyso-PAF-PLD in the culture, and a step of collecting the lyso-PAF-PLD from the culture. The lyso-PAF-PLD may be used as is in a mixture with the raw materials and other products and the like, but for some purposes and applications it is desirable to effectively eliminate all impurities, and normally the lyso-PAF-PLD can be purified to a purity of at least 50%, or at least 70%, or at least 95%. Low-purity lyso-PAF-PLD may be used for economic reasons, while high-purity lyso-PAF-PLD may be used in order to increase specificity. The proteins of (b), (c), (e) and (f) above, which are mutant forms of lyso-PAF-PLD, can also be obtained by methods known to those skilled in the art, by for example performing Inverse PCR in accordance with the manual of a commercial KOD-Plus-Mutagenesis Kit (Code No. SMK-101) using a lyso-PAF-PLD plasmid as a template.

The amount of lyso-PAF-PLD used in the present embodiment is not particularly limited as long as $Lp$-$PLA_2$ activity can be measured, but for purposes of stable measurement it is preferably at least 0.1 mg/mL, while from the economic standpoint, a range of 0.01 mg/mL to 1.5 mg/mL is preferred, and normally a range of 0.1 mg/mL to 1.5 mg/mL is preferred from both these standpoints.

In the present embodiment, "PLD activity" means phospholipase D-like activity, such as the enzyme activity of hydrolyzing the bonds between the choline sites and phosphoric acid sites of a PAF or lyso-PAF for example. When the substrates are PAFs for example, PLD activity means the enzyme activity of catalyzing the following reaction to thereby hydrolyze the PAFs and produce PAF decholinates and choline.

[Chemical formula 13]

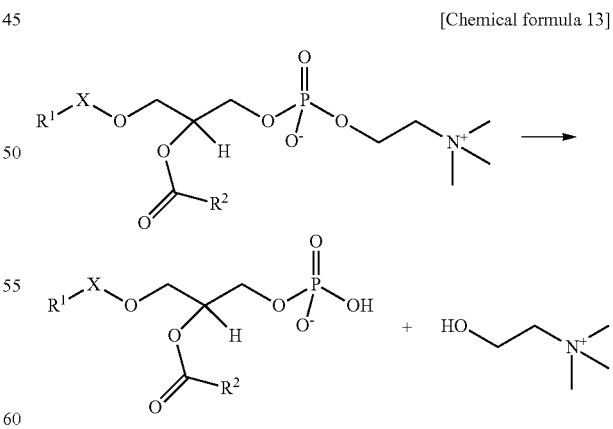

Similarly, when the substrate is lyso-PAFs, PLD activity means the enzyme activity of hydrolyzing the lyso-PAFs to thereby produce a lyso-PAF decholinates and choline.

In the present embodiment, "lyso-PAF decholinates" are phosphoric acid derivatives produced by hydrolyzing the bonds between the choline sites and phosphoric acid sites of the lyso-PAFs. An example is a compound represented by the following General Formula III:

[Chemical formula 14]

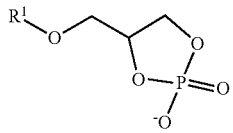

(III)

(where $R^1$ is defined as in General Formula I).

Lyso-PAF decholinates include those existing in the chain forms represented by General Formula IV below:

[Chemical formula 15]

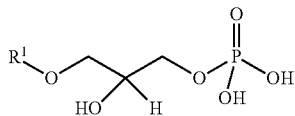

(IV)

(where $R^1$ is defined as in General Formula I).

The enzyme used in the step (B) is a protein having PLD activity against lyso-PAF but no PLD activity against PAF. This specificity means that only lyso-PAFs generated from PAFs by Lp-PLA$_2$ activity in the sample in step (A) is hydrolyzed in the step (B). To confirm whether or not the enzyme has PLD activity against PAF and whether or not it has PLD activity against lyso-PAF, the enzyme can be reacted with PAF or lyso-PAF, and the presence or absence of a reaction product (preferably choline) produced by PLD activity can be verified as described in Example 1. For example, in the present embodiment if an enzyme is said to have "no PLD activity against PAF", this means that when the PAF and the enzyme are reacted under the conditions described in Example 1 below, the enzyme activity leaves at least 95% of the PAF, or preferably at least 98% of the PAF, or more preferably at least 99% of the PAF undecomposed.

The ratio of the sample and reagents in steps (A) and (B) (S/R ratio) may be any that allows Lp-PLA$_2$ activity to be measured, but from the standpoint of avoiding the effects of coexisting substances derived from the sample the range is preferably 1:40 to 1:200, while from the standpoint of measuring with high sensitivity the range is preferably 1:5 to 1:20. From both these perspectives, the S/R ratio in one embodiment is preferably in the range of 1:30 to 1:100. This means that when using 5 μL of sample, 150 μL of the first reagent and 100 μL of the second reagent for example, the S/R ratio becomes 1:50.

In one aspect of the present embodiment, the "quantitative change attributable to hydrolysate obtained in step (B)" described in the step (C) is not particularly limited as long as it is a change that can be used as an indicator for measuring Lp-PLA$_2$ activity in a sample. Examples include a change in the amount of choline and a change in the amount of lyso-PAF decholinates, and the amount of choline is preferred for ease of measurement.

In one aspect of the present embodiment, the step (C) also includes the following step (C-1):

(C-1) reacting choline with a choline oxidase to produce hydrogen peroxide.

As shown in the following examples, the step (C-1) is performed by bringing the choline produced from a lyso-PAF by the action of lyso-PAF-PLD into contact with a reagent containing a choline oxidase.

In one aspect of the present embodiment, the step (C) also includes the following step (C-2):

(C-2) measuring the amount of hydrogen peroxide produced in the step (C-1) by a colorimetric method using a chromogenic reagent.

As shown in the following examples for example, the step (C-2) is performed by measuring the absorbance after reacting the hydrogen peroxide produced in the step (C-1) with a peroxidase and a chromogenic reagent.

The amount of hydrogen peroxide produced in the step (C-1) of the present embodiment may be measured for example by using a peroxidase or the like to produce a dye or the like, and then measuring the resulting color by colorimetric analysis, without limitation, and any known measurement method may be used. For example, the hydrogen peroxide mentioned above may be measured through luminescence, fluorescence or the like, or by electrochemical means.

When a change in the amount of choline is measured as the quantitative change attributable to the hydrolysate obtained in the step (B), the choline may be measured directly by a method using HPLC for example, or by a method using LC/MS or the like.

The choline oxidase used in the present embodiment is not particularly limited as long as it can act effectively on the choline contained in the sample and reaction system to oxidize the choline, but an enzyme classified as EC 1.1.3.17 is preferred. Examples include choline oxidase (COD) from *Arthrobacter globiformis* (Asahi Kasei Pharma Corporation, Product No. T-05) (Ikuta, S., Matsuura, K., Imamura, S., Misaki, H. and Horiuchi, Y. (1977), J. Biochem. 82, 157-163)) or recombinants thereof, and choline oxidase made by Toyobo Co., Ltd. (product name: CHO-301).

The chromogenic reagent used when measuring the amount of hydrogen peroxide may be a Trinder reagent that produces a dye through oxidative condensation between a chromogen such as phenol and a coupler such as 4-AA or 3-methyl-2-benzothiazolinone hydrazone (MBTH) in the presence of a peroxidase, or a leuco-type reagent that is oxidized and developing color directly in the presence of a peroxidase or the like. A phenol derivative, aniline derivative, toluidine derivative or the like may be used as the chromogen of the Trinder reagent, and specific examples include chromogens described in the 30th edition of the Dojindo Laboratories general catalog, such as N-ethyl-N-(2-hydroxy-3-sulfopropyl)-3-methylaniline, sodium salt, dihydrate (TOOS), N,N-bis(4-sulfopropyl)-3-methylaniline, disodium salt (TODB) and N-ethyl-N-(2-hydroxy-3-sulfopropyl)-3,5-dimethoxyaniline sodium salt (DAOS) (all manufactured by Dojindo Laboratories). Specific examples of leuco reagents include N-(carboxymethylaminocarbonyl)-4,4-bis(dimethylamino)biphenylamine (DA64) and 10-(carboxymethylaminocarbonyl)-3,7-bis(dimethylamino) phenothiazine (DA67) (both manufactured by Wako Pure Chemical Industries, Ltd.) and the like. In one embodiment, TOOS or TODB is preferably used for the Trinder reagent for reasons of measurement sensitivity.

The amount of hydrogen peroxide may be measured by known methods using a compound such as homovanillic acid or 4-hydroxyphenylacetic acid that emits fluorescence by oxidation when measurement is performed by fluorescent methods, or a catalyst such as luminol, lucigenin or isoluminol when measurement is performed by chemoluminescent methods.

When an electrode is used to measure the amount of hydrogen peroxide, the electrode is not particularly limited as long as it is made of a material capable of transferring electrons to and from hydrogen peroxide, such as platinum, gold, silver or a carbon material such as glassy carbon or the like. A known method such as amperometry, potentiometry, coulometry or the like may be used as the electrode measurement method. An electron carrier may also be interposed in the reaction between the oxidase or substrate and the electrode, and the oxidation/reduction current or the electric quantity thereof may be measured. Any substance having electron transfer ability may be used as the electron carrier, and examples include ferrocene derivatives, quinone derivatives and the like. An electron carrier may also be interposed between the electrode and the hydrogen peroxide produced by the oxidase reaction, and changes in the resulting oxidation/reduction current, electric quantity or potential may be measured.

In the present embodiment, "Lp-PLA$_2$ activity measurement" may be accomplished by measuring the amount of choline for example, without limitation, and Lp-PLA$_2$ activity may also be measured by assaying lyso-PAF decholinates. An existing assay method may be used as the method for assaying the lyso-PAF decholinates, and examples include HPLC methods, methods using chromogenic reagents, and methods using LC/MS or LC-MS/MS and the like.

In one aspect of the present embodiment, the method for measuring Lp-PLA$_2$ activity comprises the following step (D) prior to the step (A):

(D) removing the choline in the sample.

As shown in the following examples, the step (D) is performed by bringing together a sample containing choline and a reagent containing choline oxidase.

In the present embodiment, a step of "removing the choline" may be for example a step of using a choline oxidase to oxidize and remove the choline in a sample, without limitation, and the choline may be removed from the reaction system in any way that does not affect the measurement system, such as by dialysis, gel filtration, ultrafiltration or the like.

In the present embodiment, the "temperature" in each step of the method for measuring Lp-PLA$_2$ activity is given as 37° C. for example, without limitation, and measurement may be performed at any temperature range at which the enzyme functions normally, and the temperatures need not be the same in each step. For example, step (B) may be performed at any temperature at which lyso-PAF-PLD is active. As shown in the Reference Example 10 below, since lyso-PAF-PLD is not inactivated by storage at 20 to 60° C., Lp-PLA$_2$ activity is preferably measured at a temperature range of 20° C. to 60° C.

Choline oxidase is also not completely inactivated at 20° C. to 60° C. and thus, the step using choline oxidase can also be performed within this temperature range. Because choline oxidase is highly stable at 40° C. or less in particular, measurement at 40° C. or less is particularly desirable.

In the present embodiment, the "measurement time" for measuring Lp-PLA$_2$ activity is given as 10 minutes for example, without limitation. A pre-incubation period during which the PAFs and lyso-PAF-PLD are mixed and pre-incubated may also be provided prior to measurement. The pre-incubation period may be omitted, but is preferably enough time for the sample components to react sufficiently with the first reagent. Pre-incubation is a pre-heating step performed either with the reagent alone or after pre-mixing the sample with a reagent in order to improve measurement accuracy and reactivity. The time and temperature may be varied appropriately according to the purpose of pre-incubation, and for example when the purpose is to use an enzyme to eliminate unwanted substances in the sample and the reagent materials, the temperature may be one at which the enzyme functions well (such as about 37° C.).

Moreover, as shown in Example 18 below, the steps (A) to (C) may also be initiated simultaneously because the reaction begins immediately once the second reagent containing PAF is added after the sample has been mixed with the first reagent containing lyso-PAF-PLD and pre-incubated.

The sample volume may be increased or decreased appropriately in the present embodiment. The sample volume may be increased for purposes of highly sensitive measurement or decreased to reduce the effects of interferences such as hemoglobin and bilirubin, and 3 μL or more is preferably used in one embodiment.

In one aspect of the present embodiment, a "buffer (also called buffering agent)" described in the Theory and Practice on Enzymes and other Proteins [*Tanpakushitsu/Kouso no kiso fikkenhou*] (revised Second Ed., Takeichi Horio, 1994, Nankodo) and the 30th edition of the Dojindo Laboratories general catalog is preferably used in order to maintain and/or increase the reactivity and/or stability of the enzyme used. The "buffer" is not limited as long as it can maintain the target pH, but for example a Good's pH buffer (MES, Bis-Tris, ADA, PIPES, ACES, BES, MOPS, TES, HEPES, DIPSO, TAPSO, POPSO, HEPPSO, EPPS, Tricine, Bicine, TAPS, CHES, CAPS or the like), Tris buffer, diethanolamine buffer, carbonate buffer, glycine buffer, boric acid buffer, phosphate buffer, glycylglycine buffer, acetate buffer, citrate buffer, succinate buffer, maleate buffer, tris-ethanolamine buffer, imidazole buffer or the like may be used. These buffers may be adjusted with a strong acid such as hydrochloric acid or a strong alkali such as NaOH to a useful pH range for a buffer. HEPES, MOPS, TES, PIPES, Pi-K (potassium phosphate) or Tris is preferred, and Tris is more preferred.

The concentration of the "buffer" is not particularly limited as long as it can maintain the target pH, and the lower limit may be at least 3 mM, or preferably at least 5 mM, or more preferably at least 10 mM, while the upper limit may be not more than 500 mM, or preferably not more than 200 mM, or more preferably not more than 100 mM. For example, a concentration of at least 25 mM and not more than 100 mM is more preferred, and 50 mM is especially preferred.

In one aspect of the present embodiment, the "pH" in each step is not limited as long as it does not inactivate the enzyme, and the lower limit may be at least pH 5.0, or preferably at least pH 6.0, or still more preferably at least pH 7.0, while the upper limit may be not more than pH 9.0, or preferably not more than pH 8.5, or still more preferably not more than pH 8.0. In one embodiment, all steps are performed at pH 7.5. The pH may be set appropriately after consulting the optimum pH values for each enzyme used, and considering the optimum pH for Lp-PLA$_2$ activity for example, the lower limit may be at least pH 6.0 and the upper limit not more than pH 9.0 for example, or preferably the pH is at least pH 7.5 and not more than pH 8.0, or still more preferably the pH is at least pH 7.5 and not more than pH 7.75. This means that the measurements are not easily affected by carbon dioxide in the air because they can be carried out at close to neutral pH.

The Lp-PLA$_2$ activity measurement method in one aspect of the invention can be implemented using a composition (reagent) containing the enzyme, buffer and the like described above. As described below, other components commonly used to improve stability, accuracy and/or specificity in enzymatic activity measurement compositions, such as enzymes, activators, salts, surfactants, stabilizers, chelating agents, sugars or preservatives, may also be added and used in such a composition.

In the present embodiment, an ascorbate oxidase can be used to eliminate ascorbic acid contained in a sample. The ascorbate oxidase is preferably one that acts to effectively eliminate ascorbic acid, and an enzyme classified as EC 1.10.3.3 is more preferred. For example, an ascorbate oxidase from a cucurbitaceous plant may be used. Preferred examples include an ascorbate oxidase from the *Acremonium* genus (Asahi Kasei Pharma Corporation (T-53)) because it has high enzyme stability, and an ascorbate oxidase manufactured by the Amano Enzyme Inc. (trade name ASO-3) because it is not inhibited by sodium azide. Ascorbic acid may also be eliminated chemically using AAQ (ascorbic acid quencher, Dojindo Laboratories) or the like.

In the present embodiment, a catalase is used in some cases to eliminate hydrogen peroxide. The catalase is preferably one of which activity is inhibited by sodium azide, and that substantially acts to eliminate hydrogen peroxide, and an enzyme classified as EC 1.11.1.6 is more preferred, without limitation. The amount of the catalase used is not limited, but is normally in the range of 10 to 5000 U/mL. Preferred examples of catalases include *Arthrobacter* catalase (Asahi Kasei Pharma Corporation) because of its high purity, and Animal catalases (Sigma, C1345 and the like) because they are inexpensive and easy to obtain.

In the present embodiment, potassium ferrocyanide (K$_4$[Fe(CN)$_6$], any counter-ion is optional) is used in some cases to eliminate bilirubin contained in the sample. The amount of the potassium ferrocyanide used is not limited, but is normally in the range of 1 to 500 µM. In cases in which potassium ferrocyanide adversely affects the embodiment by causing non-specific coloration or the like, the concentration can be lowered or the chelating agent described below can be added. It is known that potassium ferrocyanide exists in equilibrium with potassium ferricyanide under the influence of dissolved oxygen in aqueous solution.

In the present embodiment, when glycerophosphocholine (hereunder GPC) is mixed in with the sample and/or the reagent raw materials, an enzyme having glycerophosphorylcholine phosphodiesterase (GPCP) activity can be used to eliminate the GPC. The GPCP is preferably one that acts to substantially eliminate GPC, and more preferably one classified as EC 3.1.4.2. A commercial example is GPCP from *Gliocladium roseum* (Asahi Kasei Pharma Corporation (T-33)). Glycerophosphodiester phosphodiesterase classified as EC 3.1.4.46 can also be used because it has the effect of eliminating GPC. Recombinant forms of enzymes with known sequences having GPCP activity can also be prepared based on genetic engineering techniques (Takaaki Tamura (2012), Genetic Engineering Learned from the Foundations [*Kiso kara manabu idenshi kougaku*], etc.) and used.

When eliminating substances in the sample in the present embodiment as described above, the sample can also be pre-incubated with reagents including one or more of any of the enzymes described above as necessary. When the aim is to eliminate substances contained in the reagent raw materials in advance, pre-incubation may also be performed as necessary after preparation of the reagents.

In some cases a "salt" may also be used as an enzyme activator in the present embodiment. A preferred example of a "salt" is CaCl$_2$, and other examples include salts that activate lyso-PAF-PLD and choline oxidase, such as MgCl$_2$, NaCl, KCl, ammonium sulfate and NH$_3$Cl. Multiple kinds of salts may also be mixed and used in any proportions. The negative ion constituting the salt is not limited to Cl$^-$ as long as the enzyme works.

In the present embodiment, the concentration of the "salt" used may be any amount that activates lyso-PAF-PLD and choline oxidase and the lower limit may be 0 mM or more, while the upper limit is not particularly limited but is preferably not more than 200 mM, or more preferably not more than 100 mM, or especially not more than 10 mM. A salt does not need to be added in cases in which sufficient metal ions for activating the enzyme are already contained in the sample and the reaction system.

In the present embodiment, a "surfactant" is sometimes used to the stability, accuracy and specificity of measurement. An example of a "surfactant" is Triton X-100 (hereunder called Tx-100), without limitation, and the surfactant may be any that allows Lp-PLA$_2$ to be measured. Examples include polyoxyethylene alkyl ethers, polyoxyethylene secondary alkyl ethers, polyoxyalkylene alkyl ethers, polyoxyethylene sorbitan fatty acid esters, polyoxyethylene glycerin fatty acid esters, polyoxyethylene sorbitol fatty acid esters, polyoxyethylene alkylphenyl formaldehyde condensate, polyoxyethylene castor oil, polyoxyethylene sterols, polyoxyethylene polyoxypropylene alkyl ethers, polyoxyethylene lanolins, polyoxyethylene alkylamines/fatty acid amides, polyoxyethylene alkyl ether phosphates/phosphate salts, polyoxyethylene alkyl ether sulfate salts, polyglycerin fatty acid esters, glycerin fatty acid esters, propylene glycol fatty acid esters, sorbitan fatty acid esters, N-acylamino acid salts, alkyl ether carboxylate salts, alkylphosphate salts, N-acyltaurate salts, sulfonate salts, alkyl sulfates, betaine acetate amphoteric surfactants, imidazoline amphoteric surfactants, lecithin derivatives, polyethylene glycols, polyethylene glycol lauryl ether, polyethylene glycol isooctylphenyl ether, polypropylene glycol, polyvinyl alcohol and the like, and any surfactant known to those skilled in the art may be used. Preferred examples include ether or ester forms of non-ionic surfactants, and more preferred examples include non-ionic surfactants selected from the group consisting of the polyoxyethylene derivatives, the polyoxyethylene alkyl ethers, and polyoxyethylene alkylamine with HLB values of 12 to 19. Still more preferred examples include polyoxyethylene secondary alkyl (7-21) ether, polyoxyethylene octyl phenyl ether, polyoxyethylene alkyl ether, polyoxyethylene lauryl ether, polyoxyalkylene alkyl ether and the like. Examples of commercial surfactants include NIKKOL BT-7, NIKKOL BT-9, NIKKOL BT-12, NIKKOL BT-21 (Nikko Chemicals Co., Ltd.), Tx-100, EMULGEN 709, EMULGEN 108, EMULGEN 1108, EMULGEN 1118S-70, EMULGEN 1150S-60, LS-106, LS-110 (Kao Corporation) and the like. From the standpoint of the solubility of the surfactant, a polyoxyethylene alkyl phenyl ether-type non-ionic surfactant is preferred. Trade names include Tx-100, EMULGEN 909, EMULGEN 910, EMULGEN 911 (Kao Corporation), NIKKOL OP-3, NIKKOL OP-10, NIKKOL OP-30 (Nikko Chemicals Co., Ltd.), and Nonion HS-208, HS-210, HS-208, HS-208.5, NS-210 (NOF Corporation) and the like. NPE alternatives have been widely studied since the late 1990's for reducing environmental burden and preventing health damage (Current Status and Future of Risk Management for Nonylphenols and Nonylphenol Ethoxylates, National Institute of Technology and Evaluation (http://www.nite.go.jp/data/000010070.pdf)). Surfactants described in the following catalogs (Kao Surfactants, Kao Corporation, 2012/8; General Product Catalog, Nikko Chemicals Co., Ltd., etc.) that were developed in this context can be selected, and EMULGEN 1118S-70 and EMULGEN 1150S-60 are preferred. Multiple kinds of surfactants may also be mixed and used.

In the present embodiment, the concentration of the surfactant used is not particularly limited, and may be set appropriately according to the kind of surfactant used, but may be not more than 0.2% for example, or preferably not more than 0.1%.

In the present embodiment, a "chelating agent" described in the Theory and Practice on Enzymes and other Proteins [*Tanpakushitsu/Kouso no kiso jikkenhou*] (revised Second Ed., Takeichi Horio, 1994, Nankodo) and the 30th edition of the Dojindo Laboratories general catalog is used in some cases to improve measurement stability, accuracy and specificity. Examples of such "chelating agents" include EDTA, EGTA, NAT, organic acids such as citric acid and succinic acid and the like, with no limitations as to type or concentration. For example, when EDTA is used, the concentration thereof is normally at least 0.05 mM and not more than 10 mM. When a protease that utilizes a metal for its activity expression coexists in the composition, the chelating agent can act as an enzyme-stabilizing agent in the composition by inhibiting the activity of the protease.

In the present embodiment, a "stabilizer" may be used to increase the stability of the composition when the measurement reagents are in the form of a composition. A protein such as bovine albumin, egg albumin, human albumin or crystalline that has no catalytic action may be used as such a "stabilizer", with no limitations as to type or concentration. When bovine albumin is included for example, the content thereof is normally at least 0.01% (w/v) and not more than 5% (w/v). Because these proteins are substrates for proteases, they may also serve as enzyme stabilizers. Moreover, they can also function as excipients when the composition is freeze dried.

In the present embodiment, when the measurement reagents are in the form of a composition a "sugar" may be used to increase the stability of the composition. Examples of this "sugar" include mannitol, trehalose, cyclodextrin and the like, at any concentration within the dissolvable range. When sucrose is included for example, the concentration thereof is at least 0.05% (w/v), or preferably at least 0.1% (w/v), or more preferably at least 0.3% (w/v), with an upper limit of not more than 30% (w/v), or preferably not more than 10% (w/v), or still more preferably not more than 5% (w/v). These "sugars" may also function as excipients when the composition is freeze dried.

In the present embodiment, when the measurement reagents are in the form of a composition, a "preservative" may be used to prevent deterioration or denaturation of the composition, with no limitations as to type or concentration. When using sodium azide or ProClin (product No. 48911-U, Sigma-Aldrich) for example, the concentration may be at least 0.005% (w/v), or preferably at least 0.01% (w/v), or more preferably at least 0.03% (w/v), and the upper limit may be not more than 1% (w/v), or preferably not more than 0.5% (w/v), or still more preferably not more than 0.1% (w/v). When using an antibiotic for example, the lower limit may be at least 5 µg/mL, or preferably at least 10 µg/mL, or more preferably at least 30 µg/mL, and the upper limit may be not more than 100 µg/mL, or preferably not more than 75 µg/mL, or more preferably not more than 60 µg/mL.

In one aspect of the present embodiment, the composition for measuring Lp-$PLA_2$ activity may be provided in the form of a liquid product, frozen liquid product, freeze-dried liquid product or dried liquid product (heat dried and/or air dried and/or vacuum dried, etc.). For capillary use in point-of-care equipment or for use as an enzyme sensor, the concentrations of each component are preferably higher than usual, and in this case, for example, the composition is preferably immobilized, or impregnated in a paper or film, or made into a gel-sol testing reagent kit.

In the composition in the present embodiment all the components may be made into a single composition, or they may be separated into two or more compositions. These two or more compositions together may be called a kit.

One aspect of the present embodiment provides a kit for measuring Lp-$PLA_2$ activity in a sample, containing lyso-PAF-PLD and PAFs.

The kit of the present embodiment may further be used in combination with a calibration reagent containing at least a known quantity of Lp-$PLA_2$. This calibration reagent may be a reagent containing at least a known quantity of Lp-$PLA_2$ for example, and preferably additionally contains one or more of the activators, salts, surfactants, stabilizers, chelating agents, sugars, preservatives or the like described above. An example of a commercial product is TruCal Lipid (Diasys). Conditions such as the types and concentrations of the components of this reagent can be determined appropriately by a person skilled in the art. The method of calibration using this reagent may be single-point calibration or multipoint (polygonal line or spline) calibration, or a linear regression of multipoint calibration.

The known quantity of the Lp-$PLA_2$ in the calibration reagent is not particularly limited, and may be selected appropriately so as to allow the Lp-$PLA_2$ in a sample to be measured accurately. When the sample is serum or plasma from a subject, the lower limit of the known quantity of Lp-$PLA_2$ in the calibration reagent may be at least 5 U/L, or preferably at least 10 U/L, or more preferably at least 15 U/L, and the upper limit may be not more than 600 U/L, or preferably not more than 300 U/L, or more preferably not more than 150 U/L. These values may differ depending on the reagent composition, the measurement conditions such as temperature, measurement wavelength and sub wavelength, and the definition of activity value.

In one embodiment, the known quantity (known concentration) of the Lp-$PLA_2$ in the calibration reagent is preferably set at a high value so that more sample measurement values fall within the range of the calibration curve, and from the standpoint of increasing the accuracy of the sample measurement values, the quantity is preferably set near the Lp-$PLA_2$ concentration mode of the sample (such as about 20 U/L when the sample is human serum or plasma).

One way to make the known quantity of Lp-$PLA_2$ in the calibration reagent be a high concentration is to add recombinant Lp-$PLA_2$ (WO 2015/048177). When not using recombinant Lp-$PLA_2$ (such as when using natural human Lp-$PLA_2$), a sample (such as human-derived serum or plasma) that is presumed to have a high Lp-$PLA_2$ concentration may be used as is, or pooled to prepare a calibration reagent. A sample that is presumed to have a high Lp-$PLA_2$ concentration can be selected with reference to factors such as LDL-C (LDL cholesterol) and body weight, which are reported to correlate highly with Lp-$PLA_2$ concentration (Non-Patent Document 1). Human Lp-$PLA_2$ can also be purified or concentrated by freeze drying for this use.

When preparing a calibration reagent near the Lp-PLA$_2$ concentration mode, an ordinary sample (such as human-derived serum or plasma) or a pool of such samples may be used. One example of such a calibration reagent is the pooled serum J042-II described in the following examples. A calibration reagent is sometimes also called a calibrator. Moreover, (U/L) is sometimes expressed as (nmol/min/mL).

The Lp-PLA$_2$ used in such a calibration reagent is preferably human Lp-PLA$_2$, but animal Lp-PLA$_2$ or the like may also be used as long as the reactivity matches.

The kit in the present embodiment may be a one-reagent system or a two-reagent system or more, and a two-reagent system is preferred. In the case of a two-reagent system, one aspect of the kit preferably contains lyso-PAF-PLD in a first reagent and PAFs in a second reagent for economic reasons and also to simplify the compositions of each reagent and the measurement condition settings. A kit containing a choline oxidase in the first reagent is more preferred.

In one aspect of the present embodiment, if the kit is a two-reagent system the lyso-PAF-PLD may be contained in both the first reagent and the second reagent, but is preferably contained only in the first reagent. However, the lyso-PAF-PLD may also be contained in the second reagent instead of the first reagent. In this case, GPCP and an enzyme having PLA$_1$ activity may be further added to the first reagent. The enzyme having PLA$_1$ activity may be any enzyme that decomposes lysophospholipids (lysophosphatidylcholine, etc.) in serum without acting on PAF. Examples include MGLPII and LYPL, and MGLPII is preferred.

As shown in the Examples 22 and 23 below, in one aspect of the present embodiment Lp-PLA$_2$ activity can be measured easily and with high sensitivity even after the first reagent and second reagent have been prepared and stored for a long period of time (such as for 18 months at 4° C., 2 weeks at 37° C. or the like).

The kit may also contain a choline oxidase. In one aspect of the present embodiment, the choline oxidase may be contained in both the first reagent and the second reagent, but from the standpoint of measurement sensitivity it is preferably contained only in the first reagent. By including a choline oxidase in the first reagent, it is possible to eliminate the endogenous choline in the sample. However, measurement can also be performed by putting it in the second reagent rather than the first reagent.

A peroxidase and a chromogenic reagent may also be included in the kit. In one aspect of the present embodiment, the peroxidase may be contained in either the first reagent or the second reagent. In one aspect of the present embodiment, when a leuco-type reagent is used as the chromogenic reagent, it may be contained in either the first reagent or the second reagent. When a coupler and Trinder reagent are used for the chromogenic reagent, both may be contained in either of the first reagent and the second reagent, so long as they are contained in separate reagents.

The aforementioned buffers, activators, salts, surfactants, stabilizers, chelating agents, enzymes, sugars or preservatives and other components commonly used in compositions for measuring enzyme activity may also be added to the kit.

With the measurement method, composition and kit of the present embodiments, it is possible to provide a measurement method whereby Lp-PLA$_2$ activity can be measured using a general-purpose automatic analyzer by exploiting the substrate specificity of lyso-PAF-PLD, and this measurement method is also highly versatile and simple because the activity can be measured with a two-reagent system. Moreover, a safe measurement method can be provided because Lp-PLA$_2$ activity can be measured without using any radioactive isotopes or the like. Furthermore, a measurement method capable of accurately reflecting in vivo Lp-PLA$_2$ activity can be provided because this method uses a PAF (an endogenous substrate of Lp-PLA$_2$) to measure the activity of Lp-PLA$_2$ rather than its physical quantity.

The present embodiments also relate to a diagnostic kit containing the aforementioned composition or kit, for use in diagnosing a disease and/or condition associated with Lp-PLA$_2$. The present embodiments also relate to the diagnosis and management of diseases or conditions associated with Lp-PLA$_2$ using this kit. Lp-PLA$_2$ is believed to be a factor in a variety of diseases and inflammations, as presented in various guidelines in the U.S. and Europe ((1) ACCF/AHA Guideline for Assessment of Cardiovascular Risk in Asymptomatic Adults (2010), (2) AHA/ASA Guidelines for the Primary Prevention of Stroke (2011), (3) AACE Guideline for Management of Dyslipidemia and Prevention of Atherosclerosis (2012), (4) European Guideline on cardiovascular disease prevention in clinical practice (2012)). Examples of diseases or conditions associated with Lp-PLA$_2$ that can be diagnosed and/or managed with the kit of these embodiments include cardiovascular diseases, inflammatory diseases, kidney diseases, sepsis, cancer and the like. Examples of cardiovascular diseases include atherosclerosis and stroke, and in one aspect cardiovascular disease related to atherosclerosis is preferred.

EXAMPLES

The present invention is explained in more detail below with reference to examples and reference examples (sometimes called "examples and the like" below), but the scope of the present invention is not limited to these examples and the like. For example, a "reagent of the invention" in the examples and the like represents only one specific example of the invention, and does not limit the scope of the invention.

The abbreviations in the text are defined as follows.
PLD: Phospholipase D
EDTA: Ethylenediaminetetraacetic acid
Tris: 2-Amino-2-hydroxymethyl-1,3-propanediol
Tx-100: Triton X-100
CV: Column volume
SDS: Sodium dodecyl sulfate
PAGE: Polyacrylamide gel electrophoresis
ASOM: Ascorbate oxidase
TODB: N,N-bis(4-sulfobutyl)-3-methylaniline, disodium salt
4-AA: 4-Aminoantipyrine
SR ratio: Ratio of sample volume to reagent volume
rLp-PLA$_2$: Recombinant Lp-PLA$_2$
Bis-Tris: Bis(2-hydroxyethyl)iminotris(hydroxymethyl)methane
HEPES: 2-[4-(2-Hydroxyethyl)-1-piperazinyl]ethanesulfonic acid
MOPS: 3-Morpholinopropanesulfonic acid
TES: N-tris(hydroxymethyl)methyl-2-aminoethanesulfonic acid
PIPES: Piperazine-1,4-bis(2-ethanesulfonic acid)
PC: Phosphocholine
FTU: Formazin turbidity unit The reagents used in these examples and the like were obtained as necessary from the following manufacturers.
1) Tris (Wako Pure Chemical Industries, Ltd.)
2) EDTA (Dojindo Laboratories)
3) KCl (Wako Pure Chemical Industries, Ltd.)
4) Tx-100 (Wako Pure Chemical Industries, Ltd.)

5) CaCl$_2$ (Wako Pure Chemical Industries, Ltd.)
6) ASOM (T-53, Asahi Kasei Pharma Corporation)
7) TODB (Dojindo Laboratories)
8) Peroxidase (Sigma)
9) 4-AA (Wako Pure Chemical Industries, Ltd.)
10) Choline oxidase (T-05, Asahi Kasei Pharma Corporation)
11) C16-02:0 PC (1-O-Hexadecyl-2-acetyl-sn-glycero-3-phosphocholine (Product No. 878110P, Avanti Polar Lipids, Inc.). Called PAF(C16) hereunder.
12) C16 Lyso PAF (1-O-Hexadecyl-2-hydroxy-sn-glycero-3-phosphocholine (Product No. 878119P, Avanti Polar Lipids, Inc.). Called lyso-PAF(C16) hereunder.
13) C18-02:0 PC (1-O-Octadecyl-2-acetyl-sn-glycero-3-phosphocholine) (Product No. 878114P, Avanti Polar Lipids, Inc.). Called PAF(C18) hereunder.
14) PAF (from Heart PC) (1-Alkyl-2-acetoyl-sn-glycero-3-phosphocholine) (Product No. 840009P, Avanti Polar Lipids, Inc.). Called native PAF hereunder.
15) 16:0-02:0 PC (1-Palmitoyl-2-acetyl-sn-glycero-3-phosphocholine (Product No. 880622C, Avanti Polar Lipids, Inc.).
16) ProClin™ 300 (Sigma-Aldrich)
17) Potassium ferrocyanide (Wako Pure Chemical Industries, Ltd.)
18) L(+)-Ascorbic acid (Wako Pure Chemical Industries, Ltd.)

In these examples, the recombinant lyso-PAF-PLD used in the reagents was prepared by the methods described in Reference Examples 1 to 3 below. The recombinant form of choline oxidase (T-05) from *Arthrobacter globiformis* (hereunder called recombinant choline oxidase) was prepared according to the techniques described herein and in the literature referenced (Takaaki Tamura (2012), Genetic Engineering Learned from the Basics [*Kiso kara manabu idenshi kougaku*]) and the like. The choline oxidase (hereunder called recombinant choline oxidase III) from *Thermoactinomyces monosporus* (also called *Saccharomonospora glauca*) was prepared by the methods disclosed in Patent Publication JP-A-H05-317056. The racemic PAF(C16) was synthesized by the methods disclosed in J. Org. Chem. 1995, Vol. 60, pp. 7706-7708, using 1-O-hexadecyl-rac-glycerol as a starting material.

The serum and plasma used as samples in these examples were obtained from the following manufacturers, vendors and providers. In-house volunteer serums were collected with informed consent under the cooperation of doctors and nurses.

Individual serum (Nos. 1 to 32 and 78): BizCom Japan

Pooled serums A to D, heparin pooled plasma, citrated pooled plasma (Kohjin Bio Co., Ltd.) and BJ pool (BizCom Japan)

Pooled serum J042, pooled serum J042-II: Japanese Committee for Clinical Laboratory Standards (JCCLS)

Individual serum A to E: In-house volunteer serum

The recombinant Lp-PLA$_2$ (rLp-PLA$_2$) used in these examples was prepared in accordance with Reference Examples 4 to 6 based on the information disclosed in J. Biol. Chem., Oct. 27, 1995, No. 43, Vol. 270, pp. 25481-25487.

A Hitachi 7080 automatic analyzer, Hitachi 7600-010S automatic analyzer and Hitachi 7170 automatic analyzer (Hitachi High-Technologies Corporation) were used for measuring activity in these examples. Detailed information regarding analytic methods, measuring points and other parameters can be found in the manuals for each device.

Unless otherwise specified, in these examples the Method 1 described under 1) below is used for calculating Lp-PLA$_2$ activity values. In these examples, (nmol/min/mL) is sometimes expressed as (U/L).

1) Method 1 for calculating Lp-PLA$_2$ activity value (unless otherwise specified)

This is calculated by the following formula based on the absorbance change per minute (ΔmAbs/min) as calculated from absorbance at the measuring points and the millimolar extinction coefficient ($\varepsilon=36$) of TODB at 546 nm.

$$Lp\text{-}PLA_2 \text{ activity value (nmol/min/mL)} = \{\Delta Abs/\min\}/TODB$$
$$\text{millimolar extinction coefficient}/\{(\text{sample volume})/$$
$$(\text{sample volume} + R1 \text{ reagent volume} + R2 \text{ reagent volume})\} \times$$
$$1000 = \{(\Delta mAbs/\min)/36\}/\{(\text{sample volume})/$$
$$(\text{sample volume} + R1 \text{ reagent volume} + R2 \text{ reagent volume})\}$$

2) Method 2 for calculating Lp-PLA$_2$ activity value (method using calibrator)

Single-point calibration using a calibrator of a known concentration with distilled water measured at the same time as 0 (nmol/min/mL (U/L)) (also called two-point calibration) is selected, and the Lp-PLA$_2$ activity value (nmol/min/mL) in a sample is calculated from the calibration curve.

Reference Example 1

<Preparation of Transformant Producing Lyso-PAF-PLD from *Thermocrispum* sp.>

Chromosomal DNA obtained from *Thermocrispum* sp. (internationally deposited under the Budapest treaty as NITE BP-01628; Deposition authority: National Institute of Technology and Evaluation Patent Microorganism Depository; Address: #122, 2-5-8 Kazusa-Kamatari, Kisarazu-shi, Chiba 292-0818, Japan, Deposit date: May 17, 2013) was extracted by the phenol-chloroform method. Using the nucleotide sequence of SEQ ID NO: 3 as the sense primer and the nucleotide sequence of SEQ ID NO: 4 as the antisense primer, PCR was performed with KOD FX (product No. KFX-101, Toyobo Co., Ltd.) to obtain a roughly 920 bp PCR product. The resulting PCR product was digested with NdeI (Takara Bio Inc.) and EcoRI (Takara Bio Inc.), and inserted into the NdeI-EcoRI site of a pET-21a(+) expression vector (Novagen) to obtain a lyso-PAF-PLD/pET21a(+) expression plasmid. This expression plasmid was transformed into One shot BL21 (DE3) Chemically Competent *E. coli* (Invitrogen), to obtain a transformant having a recombinant vector containing a polynucleotide consisting of a nucleotide sequence encoding lyso-PAF-PLD, called lyso-PAF-PLD/pET-21a(+)/BL21(DE3).

Reference Example 2

<Culture of Transformant for Producing Recombinant Lyso-PAF-PLD, and Solubilization of Bacterial Cells>

1 colony of the transformant described in Reference Example 1 was inoculated in 5 mL of liquid LB medium containing 50 μg/mL ampicillin, and cultured for 16 hours at 25° C. in a test tube for use as a seed. The seed was inoculated at $\frac{1}{1000}$ volume in 1.6 L of liquid medium containing 50 μg/mL ampicillin (Overnight Express™ Instant TB Medium with 1% glycerol, 0.1% Adekanol LG-109 (ADEKA CORPORATION)), and cultured for 26 hours at 34° C., pH 6.8, 650 rpm in a jar fermenter. The culture solution was centrifuged to harvest the bacterial cells, which were then dissolved in a solution A (10 mM Tris-HCl (pH 8.5), 1 mM EDTA (pH 9.0), 0.1% Tx-100, 0.1% lysozyme hydrochloride, product No. 36A55K, Eizai) and reacted for 30 minutes at 50° C. After being solubilized with the solution A, the bacterial cells were centrifuged, and the resulting supernatant was used as a crude enzyme solution.

Reference Example 3

<Purification of Recombinant Lyso-PAF-PLD>

The crude enzyme solution obtained in the Reference Example 2 was adsorbed to Q Sepharose Big Beads (GE Healthcare) packed in a column equilibrated with 10 mM Tris-HCl (pH 8.0) solution. This was then eluted with a 10 CV linear gradient using a 10 mM Tris-HCl (pH 8.0) solution and a 10 mM Tris-HCl (pH 8.0) solution containing 0.5 M KCl. After an eluted fraction containing recombinant lyso-PAF-PLD had been confirmed by SDS-PAGE, the eluted fraction was concentrated by a pencil-type module (UF) (Asahi Kasei Chemical) to 1/10 volume, and KCl was added to be 3 M. The solution containing lyso-PAF-PLD was then adsorbed to Phenyl Sepharose 6 Fast Flow (high sub) (GE Healthcare) packed in a column equilibrated with 10 mM of Tris-HCl (pH 8.5) solution containing 3 M of KCl, and then eluted with a 10 CV linear gradient using a 10 mM Tris-HCl (pH 8.5) solution and a 10 mM Tris-HCl (pH 8.5) solution containing 3 M of KCl. The eluted fraction was confirmed by SDS-PAGE and collected, concentrated with an Amicon Ultra-15 centrifugal filter unit (Millipore), and dialyzed with 10 mM Tris-HCl (pH 8.0) solution. The dialyzed solution was adsorbed to Q Sepharose High Performance (GE Healthcare) packed in a column equilibrated with 10 mM Tris-HCl (pH 8.5) solution. This was then eluted with a 12 CV linear gradient using 10 mM Tris-HCl (pH 8.5) and a 10 mM Tris-HCl (pH 8.5) solution containing 0.5 M of KCl. The eluted fraction was confirmed by SDS PAGE and collected, concentrated with an Amicon Ultra-15 centrifugal filter unit (Millipore), and desalted with a PD-10 column (GE Healthcare) to obtain an enzyme solution of the recombinant lyso-PAF-PLD of SEQ ID NO: 9.

Reference Example 4

<Preparation of Recombinant for Producing Human Lp-PLA$_2$>

A gene optimized for *E. coli* (matched to *E. coli* codon usage) was synthesized (GenScript (NJ, USA)) based on the sequence data for a human Lp-PLA$_2$ gene. Using the synthesized DNA as a template, a roughly 1200 bp PCR product was obtained by PCR using KOD FX (Toyobo Co., Ltd.) using as the sense primer the nucleotide sequence of SEQ ID NO: 5 in which the 42nd isoleucine was changed to the sequence of the initial methionine, with the nucleotide sequence of SEQ ID NO: 6 as the antisense primer. The resulting PCR product was digested with NdeI (Takara Bio Inc.) and BamHI (Takara Bio Inc.), and inserted into the NdeI-BamHI site of the expression vector pET-19b (Novagen) to obtain an Lp-PLA$_2$/pET-19b expression plasmid. This expression plasmid was transformed into One shot BL21(DE3) Chemically Competent *E. coli*, to obtain a transformant called Lp-PLA$_2$/pET-19b/BL21(DE3) comprising a recombinant vector containing a polynucleotide consisting of a nucleotide sequence encoding Lp-PLA$_2$ with a histidine tag from the vector added at the N-terminus.

Reference Example 5

<Culture of Transformant for Producing Recombinant Lp-PLA$_2$, and Solubilization of Bacterial Cells>

1 colony of the transformant described in Reference Example 4 was inoculated in 5 mL of liquid LB medium containing 50 µg/mL of ampicillin, and cultured for 16 hours at 25° C. in a test tube for use as a seed. The seed was inoculated in 0.8 L of liquid medium containing 50 µg/mL of ampicillin (Overnight Express™ Instant TB Medium with 1% glycerol) at a volume ratio of 1/1000, and cultured for 24 hours at 30° C. in a flask. The culture solution was centrifuged to harvest the bacterial cells, which were then dissolved in a 20 mM potassium phosphate solution (pH 7.0) containing 0.3 M NaCl, and sonicated. After solubilization of the bacterial cells by sonication, they were centrifuged, and the resulting supernatant was used as a crude enzyme solution.

Reference Example 6

<Purification of Recombinant Lp-PLA$_2$ (rLp-PLA$_2$)>

The crude enzyme solution obtained in the Reference Example 5 was adsorbed to Chelating Sepharose FF (GE Healthcare) packed in a column equilibrated with 20 mM potassium phosphate solution (pH 7.0) containing 0.3 M NaCl. This was then eluted with a linear gradient using a 20 mM potassium phosphate solution (pH 7.0) containing 0.3 M NaCl and a 20 mM potassium phosphate solution (pH 7.0) containing 400 mM imidazole and 0.3 M NaCl. An eluted fraction of recombinant Lp-PLA$_2$ was confirmed by SDS-PAGE, dialyzed overnight with 10 mM Tris-HCl (pH 7.5), and concentrated with an Amicon Ultra-15 (30K) centrifugal filter unit (Millipore) to 1/65 volume.

Reference Example 7

<Preparation of Transformant for Producing GPCP from *E. coli*>

Based on gene sequence data for glycerophosphoryl diester phosphodiesterase (GlpQ), which has GPCP activity in the *E. coli* K strain, a roughly 1000 bp PCR product was obtained by PCR with KOD FX (Toyobo Co., Ltd.) using the nucleotide sequence of SEQ ID NO: 7 as the sense primer and the nucleotide sequence of SEQ ID NO: 8 as the antisense primer with the *E. coli* LE 392 strain (transferred from the National Institute of Genetics) as the template. The resulting PCR product was digested with NheI (Takara Bio Inc.) and EcoRI (Takara Bio Inc.), and inserted into the NheI-EcoRI site of the expression vector pET-21a(+) (Novagen) to obtain a GPCP/pET-21a(+) expression plasmid. This expression plasmid was transformed into One shot BL21 (DE3) Chemically Competent *E. coli*, to obtain a transformant called GPCP/pET-21a(+)/BL21(DE3) comprising a recombinant vector containing a polynucleotide consisting of a nucleotide sequence encoding GPCP.

Reference Example 8

<Culture of Transformant for Producing Recombinant GPCP, and Solubilization of Bacterial Cells>

1 colony of the transformant described in Reference Example 7 was inoculated in 5 mL of liquid LB medium containing 50 µg/mL of ampicillin, and cultured for 16 hours at 30° C. in a test tube for use as a seed. The seed was inoculated in 600 mL of liquid medium containing 50 μg/mL of ampicillin (Overnight Express™ Instant TB Medium with 1% glycerol) at a volume ratio of 1/1000, and cultured for 24 hours at 34° C. in a flask. The culture solution was centrifuged to harvest the bacterial cells, which were then dissolved in 20 mM Tris-HCl (pH 7.5), and sonicated. After solubilization of the bacterial cells by sonication, they were centrifuged, and the resulting supernatant was used as a crude enzyme solution.

Reference Example 9

<Purification of Recombinant GPCP>

The crude enzyme solution obtained in Reference Example 8 was adsorbed to Q Sepharose Fast Flow (GE Healthcare) packed in a column equilibrated with 10 mM Tris-HCl (pH 8.0). This was then eluted with a 10 CV linear gradient using a 10 mM Tris-HCl (pH 8.0) solution and a 10 mM Tris-HCl (pH 8.0) solution containing 0.5 M of KCl. An eluted fraction of recombinant GPCP was confirmed by SDS-PAGE, and 18% ammonium sulfate was added. The solution containing GPCP with the added 18% ammonium sulfate was adsorbed to Phenyl Sepharose 6 Fast Flow (high sub) packed in a column equilibrated with 10 mM Tris-HCl (pH 8.0) solution containing 18% ammonium sulfate, and eluted with a 10 CV gradient using a 10 mM Tris-HCl (pH 8.0) solution and a 10 mM Tris-HCl (pH 8.0) solution containing 18% ammonium sulfate. The eluted fraction was confirmed by SDS-PAGE and collected, concentrated with an Amicon Ultra-15 centrifugal filter unit (Millipore), and desalted with a PD-10 column to obtain a recombinant GPCP enzyme solution.

Reference Example 10

<Thermal Stability Test of Lyso-PAF-PLD>

The purified lyso-PAF-PLD was incubated for 60 minutes at different temperatures in a 20 mM Tris-HCl (pH 7.5) solution, and residual activity was investigated with the following reaction solution. C18(Plasm) LPC (Product No. 852465P, Avanti Polar Lipids, Inc.) was used as the substrate.

(Reaction Solution Composition)

| 80 mM | Tris-HCl (pH 8.0) |
| 0.4 mM | Substrate |
| 2 mM | CaCl$_2$ |

(Color Developing Solution Composition)

| 0.03% | 4-AA |
| 0.02% | TODB |
| 0.75 U/mL | Choline oxidase (T-05, Asahi Kasei Pharma Corporation) |
| 5 U/mL | Peroxidase |
| 10 mM | EDTA |

50 μL of the reaction solution was pre-incubated for 5 minutes at 37° C., 5 μL of the enzyme solution was added, and an enzyme reaction was performed for 1 minute at 50° C. 200 μL of the color developing solution was then added and reacted for 10 minutes at 37° C., after which absorbance was measured at 550 nm. The activity value was calculated according to the following formula.

Lyso-PAF-PLD activity value $(U/mL) =$ $\{(\Delta Abs/min)/$millimolar extinction coefficient of $TODB$ at 550 nm$\}/$ $\{$(sample volume)$/$ (sample volume$+ R1$ reagent volume$+ R2$ reagent volume)$\} =$ $\{(\Delta Abs/min)/39\}/\{$(sample volume)$/$ (sample volume$+ R1$ reagent volume$+ R2$ reagent volume)$\}$ FIG. 1 shows residual activity at each temperature given 100% as the activity value when stored at 4° C.

Reference Example 11

<Preparation of Calibration Reagent>

In order to use the pooled serum J042-II as a calibration reagent (calibrator), the Lp-PLA$_2$ activity (nmol/min/mL (U/L)) in the pooled serum J042-II was measured for 5 days (n=5), and the average value was established as the known quantity (known concentration) of Lp-PLA$_2$. The reagent composition is as follows.

(Reagents of Invention)

<R1 Reagent>

| 50 mM | Tris-HCl (pH 7.8) |
| 0.2 mM | CaCl$_2$ |
| 4 U/mL | ASOM |
| 0.05% | ProClin 300 |
| 1.6 μM | Potassium ferrocyanide |
| 0.05% | EMULGEN 1150S-60 |
| 3.3 U/mL | Recombinant lyso-PAF-PLD |
| 0.1 mM | EDTA |
| 75 mM | NaCl |
| 3% | Trehalose |
| 10 μM | FAD (flavin adenine dinucleotide) |
| 0.02% | TODB |
| 4 U/mL | Peroxidase |
| 4 U/mL | Recombinant choline oxidase III |

<R2 Reagent>

| 50 mM | PIPES (pH 7.0) |
| 0.2 mM | CaCl$_2$ |
| 0.05% | ProClin 300 |
| 0.05% | EMULGEN 1150S-60 |
| 0.1 mM | EDTA |
| 0.25% | KCl |
| 0.13% | Sucrose |
| 0.08% | 4-AA |
| 2 mM | Racemic PAF (C16) |

(Sample)
Pooled serum J042-II
(Activity Measurement)
A Hitachi 7170 automatic analyzer was used to measure activity. The measurement parameters are shown below.
(Hitachi 7170 Automatic Analyzer Measurement Parameters)

| Analysis method | Rate A |
| Measurement wavelength (sub/dominant) | 660 nm/546 nm |
| Reaction time | 10 minutes |
| Measuring points | 30 to 33 |
| Sample volume | 4 μL |

| R1 reagent volume | 160 μL |
| R2 reagent volume | 40 μL |

4 μL of the sample was mixed with 160 μL of the R1 reagent, and incubated for 5 minutes at 37° C. (measuring points 1 to 16), after which 40 μL of the R2 reagent was added to initiate a reaction (measuring point 17). The absorbance of water (blank) at the same measuring points was subtracted from the absorbance of the sample about 3.6 to 4.5 minutes after the reaction was initiated by addition of the R2 reagent (measuring points 30 to 33) to calculate the absorbance change per minute (ΔmAbs/min), and the Lp-PLA$_2$ activity value (nmol/min/mL) was calculated according to the previous formula.

The results of measurement showed that the quantity (concentration) of Lp-PLA$_2$ in the pooled serum J042-II was assigned as 23.1 (nmol/min/mL (U/L)) (standard deviation (SD)=0.36 (nmol/min/mL (U/L)), (known quantity (concentration)). A calibration reagent (calibrator) could be prepared using the pooled serum. The feasibility of this calibration reagent has been verified in Example 24 and the like.

Example 1

<Specificity of Recombinant Lyso-PAF-PLD>

To investigate the specificity of the recombinant lyso-PAF-PLD purified in Reference Example 3, activity against PAF(C16) and lyso-PAF(C16) was studied. The reagent compositions are as follows.

(Reagents of Invention)
<R1 Reagent>

| 50 mM | Tris-HCl (pH 7.5) |
| 1 mM | CaCl$_2$ |
| 4 U/mL | ASOM |
| 0.1% | Tx-100 |
| 0.03% | TODB |
| 4 U/mL | Peroxidase |
| 5 U/mL | Recombinant choline oxidase |

<R2 Reagent>

| 50 mM | Tris-HCl (pH 7.5) |
| 1 mM | CaCl$_2$ |
| 0.04% | 4-AA |
| 0.1% | Tx-100 |
| 0.13 mg/mL | Recombinant lyso-PAF-PLD |

(Samples)
0.1% Tx-100 solutions containing 0 to 0.5 mM PAF (C16) or lyso-PAF (C16)

(Activity Measurement)
A Hitachi 7080 automatic analyzer was used to measure activity. The measurement parameters are shown below.
(Hitachi 7080 Automatic Analyzer Measurement Parameters)

| Analysis method | 2-point end |
| Measurement wavelength (sub/dominant) | 660 nm/546 nm |
| Reaction time | 10 minutes |
| Measuring points | 16 to 31 |
| Sample volume | 5 μL |
| R1 reagent volume | 150 μL |
| R2 reagent volume | 50 μL |

5 μL samples containing PAF(C16) or lyso-PAF(C16) at concentrations of 0, 0.1, 0.2, 0.3, 0.4 or 0.5 mM were each incubated for 5 minutes at 37° C. with 15 μL of the R1 reagent (measuring points 1 to 15), after which 50 μL of the R2 reagent was added and reacted for 5 minutes (measuring points 16 to 31). Absorbance at each measuring point during the 10-minute reaction time with the PAF samples was plotted as shown in FIG. 2. The results for the lyso-PAF samples were plotted in the same way as shown in FIG. 3.

As shown in FIGS. 2 and 3, the activity measurement results show changes in absorbance after R2 reagent addition only in the case of the lyso-PAF samples. This shows that the lyso-PAF-PLD in the R2 reagent hydrolyzed lyso-PAF to produce choline, and the hydrogen peroxide produced by oxidation of choline caused a redox chromogen reaction. Consequently, it is clear that although PAF and lyso-PAF are structurally similar, recombinant lyso-PAF-PLD exhibits PLD activity only against lyso-PAF and not against PAF.

The use of this specificity of recombinant lyso-PAF-PLD to measure Lp-PLA$_2$ activity in samples was investigated. More particularly, the measurement of Lp-PLA$_2$ activity in samples was investigated based on the principal of adding PAF to a sample, hydrolyzing the PAF into lyso-PAF with Lp-PLA$_2$ contained in the sample, and then further hydrolyzing lyso-PAF with recombinant lyso-PAF-PLD and measuring the resulting hydrolysis products.

In the Examples 2 to 10 below, the basic components of Lp-PLA$_2$ activity measurement reagents were investigated. In these examples, the criteria for high sensitivity are that an enzyme reaction in a sample proceeds more smoothly, the value of the absorbance change per minute (sensitivity) (ΔmAbs/min) is higher, and the calculated Lp-PLA$_2$ activity value (nmol/min/mL) is higher due to the nature of the added reagent components.

Example 2

<pH Study of Lp-PLA$_2$ Activity Measurement Reagents 1 (pH 6.0 to 9.0)>

To investigate the effect of pH in Lp-PLA$_2$ activity measurement reagents, the pH values of the reagents were adjusted in increments of 0.5 between pH 6.0 and 9.0 using Tris and Bis-Tris (Dojindo Laboratories), and Lp-PLA$_2$ activity in samples was measured. The reagent compositions are as follows.

(Reagents of Invention)
<R1 Reagent>

| 50 mM | Tris-HCl (each pH) |
| 1 mM | CaCl$_2$ |
| 4 U/mL | ASOM |
| 0.1% | Tx-100 |
| 0.13 mg/mL | Recombinant lyso-PAF-PLD |
| 0.03% | TODB |
| 4 U/mL | Peroxidase |
| 5 U/mL | Recombinant choline oxidase |

<R2 Reagent>

| | |
|---|---|
| 50 mM | Tris-HCl (each pH) |
| 1 mM | CaCl$_2$ |
| 0.04% | 4-AA |
| 0.5% | Tx-100 |
| 10 mM | PAF (C16) |

(Samples)
Individual serum No. 16, individual serum No. 78.
(Activity Measurement)
A Hitachi 7080 automatic analyzer was used to measure activity. The measurement parameters are shown below.
(Hitachi 7080 Automatic Analyzer Measurement Parameters)

| | |
|---|---|
| Analysis method | Rate A |
| Measurement wavelength (sub/dominant) | 660 nm/546 nm |
| Reaction time | 10 minutes |
| Measuring points | 23 to 26 |
| Sample volume | 3 µL |
| R1 reagent volume | 150 µL |
| R2 reagent volume | 100 µL |

34 of sample was mixed with 150 µL of the R1 reagent, and incubated for 5 minutes at 37° C. (measuring points 1 to 15), after which 100 µL of the R2 reagent was added to initiate a reaction (measuring point 16). The absorbance of water (blank) at the same measuring points was subtracted from the absorbance of the sample about 2 to 3 minutes after the reaction was initiated by addition of the R2 reagent (measuring points 23 to 26) to calculate the absorbance change per minute (ΔmAbs/min), and the Lp-PLA$_2$ activity value (nmol/min/mL) was calculated according to the previous formula. The values for absorbance change per minute (sensitivity) (ΔmAbs/min) and the Lp-PLA$_2$ activity values (nmol/min/mL) at each pH are shown in Tables 1 and 2.

TABLE 1

Individual serum 16

| pH | ΔmAbs/min | Activity value (nmol/min/mL) |
|---|---|---|
| 6.0 | 8.4 | 19.7 |
| 6.5 | 11.2 | 26.2 |
| 7.0 | 22.4 | 52.5 |
| 7.5 | 43.0 | 100.7 |
| 8.0 | 40.9 | 95.8 |
| 8.5 | 38.3 | 89.7 |
| 9.0 | 31.8 | 74.5 |

TABLE 2

Individual Serum 78

| pH | ΔmAbs/min | Activity value (nmol/min/mL) |
|---|---|---|
| 6.0 | 3.9 | 9.1 |
| 6.5 | 3.3 | 7.7 |
| 7.0 | 7.4 | 17.3 |
| 7.5 | 18.6 | 43.6 |
| 8.0 | 17.1 | 40.1 |
| 8.5 | 15.8 | 37.0 |
| 9.0 | 13.7 | 32.1 |

The measurement results in Tables 1 and 2 show that Lp-PLA$_2$ activity could be measured at all pH values within the range of pH 6.0 to 9.0. Moreover, Lp-PLA$_2$ activity could be measured with higher sensitivity at a pH range of 7.5 to around 8.0.

Example 3

<pH Study of Lp-PLA$_2$ Activity Measurement Reagents 2 (pH 7.25 to 7.75)>

Since Example 2 showed that Lp-PLA$_2$ activity could be measured with the highest sensitivity when the pH of the reagents was near 7.5, the effect of pH in the region of pH 7.5 was investigated in detail. The pH of the reagents was adjusted to 7.25, 7.5 and 7.75 with Tris-HCl buffer, and Lp-PLA$_2$ activity in the samples was measured. The reagent compositions are as follows.

(Reagents of Invention)
<R1 Reagent>

| | |
|---|---|
| 50 mM | Tris-HCl (pH 7.25, 7.5, 7.75) |
| 1 mM | CaCl$_2$ |
| 4 U/mL | ASOM |
| 0.1% | Tx-100 |
| 0.13 mg/mL | Recombinant lyso-PAF-PLD |
| 0.03% | TODB |
| 4 U/mL | Peroxidase |
| 5 U/mL | Recombinant choline oxidase |

<R2 Reagent>

| | |
|---|---|
| 50 mM | Tris-HCl (pH 7.25, 7.5, 7.75) |
| 1 mM | CaCl$_2$ |
| 0.04% | 4-AA |
| 0.5% | Tx-100 |
| 10 mM | PAF (C16) |

(Samples and Activity Measurement)
The sample types, measurement equipment, measurement parameters and calculations of activity values were the same as in Example 2. The values for absorbance change per minute (sensitivity) (ΔmAbs/min) and the Lp-PLA$_2$ activity values (nmol/min/mL) at each pH are shown in Tables 3 and 4.

TABLE 3

Individual Serum 16

| pH | ΔmAbs/min | Activity value (nmol/min/mL) |
|---|---|---|
| 7.25 | 29.8 | 69.8 |
| 7.5 | 41.2 | 96.5 |
| 7.75 | 41.6 | 97.5 |

TABLE 4

Individual Serum 78

| pH | ΔmAbs/min | Activity value (nmol/min/mL) |
|---|---|---|
| 7.25 | 12.8 | 30.0 |
| 7.5 | 18.0 | 42.2 |
| 7.75 | 17.8 | 41.7 |

The measurement results in Tables 3 and 4 show that Lp-PLA$_2$ activity could be measured with higher sensitivity when the pH of the reagents was 7.5 or 7.75.

Example 4

<Investigation of Buffer Solutions in Lp-PLA$_2$ Activity Measurement Reagents>

To investigate the effects of different buffer solutions in Lp-PLA$_2$ activity measurement reagents, the pH of the reagents was set at 7.5, the type of buffer solution was varied, and Lp-PLA$_2$ activity in samples was measured. A total of 6 buffers were used—the Good's buffers HEPES (Dojindo Laboratories), MOPS (Dojindo Laboratories), TES (Dojindo Laboratories) and PIPES (Dojindo Laboratories), potassium phosphate (Pi-K), and Tris (Wako Pure Chemical Industries, Ltd.). The pH of the potassium phosphate was adjusted with dipotassium hydrogen phosphate (Wako Pure Chemical Industries, Ltd.) and potassium dihydrogen phosphate (Wako Pure Chemical Industries, Ltd.). The reagent compositions are shown below.

(Reagents of Invention)
<R1 Reagent>

| | |
|---|---|
| 50 mM | Each buffer (pH 7.5) |
| 1 mM | CaCl$_2$ |
| 4 U/mL | ASOM |
| 0.1% | Tx-100 |
| 0.13 mg/mL | Recombinant lyso-PAF-PLD |
| 0.03% | TODB |
| 4 U/mL | Peroxidase |
| 5 U/mL | Recombinant choline oxidase |

<R2 Reagent>

| | |
|---|---|
| 50 mM | Each buffer (pH 7.5) |
| 1 mM | CaCl$_2$ |
| 0.04% | 4-AA |
| 0.5% | Tx-100 |
| 10 mM | PAF (C16) |

(Samples and Activity Measurement)

The sample types, measurement equipment, measurement parameters and calculations of activity values were as in Example 2. The values for absorbance change per minute (sensitivity) (ΔmAbs/min) and the Lp-PLA$_2$ activity values (nmol/min/mL) using each buffer solution are shown in Tables 5 and 6.

TABLE 5

Individual Serum 16

| Buffer solution | ΔmAbs/min | Activity value (nmol/min/mL) |
|---|---|---|
| HEPES | 32.6 | 76.4 |
| MOPS | 34.7 | 81.3 |
| TES | 32.3 | 75.7 |
| PIPES | 38.2 | 89.5 |
| Pi-K | 36.0 | 84.3 |
| Tris | 42.3 | 99.1 |

TABLE 6

Individual Serum 78

| Buffer solution | ΔmAbs/min | Activity value (nmol/min/mL) |
|---|---|---|
| HEPES | 15.6 | 36.5 |
| MOPS | 16.8 | 39.4 |
| TES | 16.0 | 37.5 |
| PIPES | 18.4 | 43.1 |
| Pi-K | 16.0 | 37.5 |
| Tris | 19.1 | 44.7 |

The measurement results in Tables 5 and 6 show that Lp-PLA$_2$ activity could be measured using any of the 6 kinds of buffer solutions. At the buffer concentration of 50 mM used in this example, Lp-PLA$_2$ activity could be measured with the highest sensitivity using Tris as the buffer solution in the reagents.

Example 5

<Investigating Tris HCl (pH 7.5) Concentration of Lp-PLA$_2$ Activity Measurement Regents>

To study the effect of the Tris-HCl (pH 7.5) concentration in Lp-PLA$_2$ activity measurement reagents, the Tris-HCl (pH 7.5) concentrations of the reagents were adjusted to 25 mM, 50 mM and 100 mM, and Lp-PLA$_2$ activity in samples was measured. The reagent compositions are as follows.

(Reagents of Invention)
<R1 Reagent>

| | |
|---|---|
| 25 to 100 mM | Tris-HCl (pH 7.5) |
| 1 mM | CaCl$_2$ |
| 4 U/mL | ASOM |
| 0.1% | Tx-100 |
| 0.13 mg/mL | Recombinant lyso-PAF-PLD |
| 0.03% | TODB |
| 4 U/mL | Peroxidase |
| 5 U/mL | Recombinant choline oxidase |

<R2 Reagent>

| | |
|---|---|
| 25 to 100 mM | Tris-HCl (pH 7.5) |
| 1 mM | CaCl$_2$ |
| 0.04% | 4-AA |
| 0.5% | Tx-100 |
| 10 mM | PAF (C16) |

(Samples and Activity Measurement)

The sample types, measurement equipment, measurement parameters and calculations of activity values were as in Example 2. The values for absorbance change per minute (sensitivity) (ΔmAbs/min) and the Lp-PLA$_2$ activity values (nmol/min/mL) using each buffer solution are shown in Tables 7 and 8.

TABLE 7

Individual Serum 16

| Concentration (mM) | ΔmAbs/min | Activity value (nmol/min/mL) |
|---|---|---|
| 25 | 42.8 | 100.3 |
| 50 | 43.5 | 101.9 |
| 100 | 40.3 | 94.4 |

TABLE 8

Individual serum 78

| Concentration (mM) | ΔmAbs/min | Activity value (nmol/min/mL) |
|---|---|---|
| 25 | 18.9 | 44.3 |
| 50 | 19.5 | 45.7 |
| 100 | 18.0 | 42.2 |

The measurement results in Tables 7 and 8 show that Lp-PLA$_2$ activity could be measured at all the Tris-HCl (pH 7.5) concentrations of 25, 50 and 100 mM. Lp-PLA$_2$ activity could be measured with higher sensitivity when the Tris-HCl (pH 7.5) concentration of the reagents was 50 mM.

Example 6

<The Effect of CaCl$_2$ Concentration in Lp-PLA$_2$ Activity Measurement Reagents>

To study the effects of CaCl$_2$ concentration in Lp-PLA$_2$ activity measurement reagents, the CaCl$_2$ concentrations of the reagents were adjusted to 0 (not added), 0.25, 0.5, 0.75, 1, 2.5, 5 and 10 mM, and Lp-PLA$_2$ activity in samples was measured. The reagent compositions are as follows.

(Reagents of Invention)
<R1 Reagent>

| | |
|---|---|
| 50 mM | Tris-HCl (pH 7.5) |
| 0 to 10 mM | CaCl$_2$ |
| 4 U/mL | ASOM |
| 0.1% | Tx-100 |
| 0.13 mg/mL | Recombinant lyso-PAF-PLD |
| 0.03% | TODB |
| 4 U/mL | Peroxidase |
| 5 U/mL | Recombinant choline oxidase |

<R2 Reagent>

| | |
|---|---|
| 50 mM | Tris-HCl (pH 7.5) |
| 0 to 10 mM | CaCl$_2$ |
| 0.04% | 4-AA |
| 0.5% | Tx-100 |
| 10 mM | PAF (C16) |

(Samples and Activity Measurement)

The sample types, measurement equipment, measurement parameters and calculations of activity values were as in Example 2. The values for absorbance change per minute (sensitivity) (ΔmAbs/min) and the Lp-PLA$_2$ activity values (nmol/min/mL) using each buffer solution are shown in Tables 9 and 10.

TABLE 9

Individual Serum 16

| Concentration (mM) | ΔmAbs/min | Activity value (nmol/min/mL) |
|---|---|---|
| 0 | 41.4 | 97.0 |
| 0.25 | 42.5 | 99.6 |
| 0.5 | 43.3 | 101.4 |
| 0.75 | 43.1 | 101.0 |
| 1 | 42.9 | 100.5 |
| 2.5 | 42.8 | 100.3 |
| 5 | 41.9 | 98.2 |
| 10 | 43.0 | 100.7 |

TABLE 10

Individual Serum 78

| Concentration (mM) | ΔmAbs/min | Activity value (nmol/min/mL) |
|---|---|---|
| 0 | 18.9 | 44.3 |
| 0.25 | 19.3 | 45.2 |
| 0.5 | 19.1 | 44.7 |
| 0.75 | 19.0 | 44.5 |
| 1 | 19.1 | 44.7 |
| 2.5 | 19.0 | 44.5 |
| 5 | 18.9 | 44.3 |
| 10 | 18.9 | 44.3 |

The measurement results in Table 9 and 10 show that Lp-PLA$_2$ activity could be measured regardless of the CaCl$_2$ concentration in the range of 0 to 10 mM. There were no differences in the Lp-PLA$_2$ activity values at any concentration, and it appears that the enzyme in the reagent functions adequately with only the CaCl$_2$ from the sample in this example.

Example 7

<Screening Surfactants for Lp-PLA$_2$ Activity Measurement Reagents>

To investigate the effects of surfactants in Lp-PLA$_2$ activity measurement reagents, the kind of surfactant added to the reagents was varied with the concentration set at 0.1% in the R1 reagent and 0.1% or 0.5% in the second reagent, and Lp-PLA$_2$ activity in samples was measured. The reagent compositions are shown below.

(Reagents of Invention)
<R1 Reagent>

| | |
|---|---|
| 50 mM | Tris-HCl (pH 7.5) |
| 1 mM | CaCl$_2$ |
| 4 U/mL | ASOM |
| 0.1% | Each surfactant |
| 0.13 mg/mL | Recombinant lyso-PAF-PLD |
| 0.03% | TODB |
| 4 U/mL | Peroxidase |
| 5 U/mL | Recombinant choline oxidase |

<R2 Reagent>

| | |
|---|---|
| 50 mM | Tris-HCl (pH 7.5) |
| 1 mM | CaCl$_2$ |
| 0.04% | 4-AA |
| 0.1% or 0.5% | Each surfactant |
| 10 mM | PAF |

(Surfactants Used)

The surfactants used in this study are shown in detail in Table 11.

TABLE 11

| No. | Product name | Chemical name | HLB |
|---|---|---|---|
| 1 | Tx-100 | POE octyl phenyl ether | 13.5 |
| 2 | BT-7 | POE(7) secondary alkyl ether | 12.0 |
| 3 | BT-9 | POE(9) secondary alkyl ether | 13.5 |
| 4 | BT-12 | POE(12) secondary alkyl ether | 14.5 |
| 5 | BL-21 | POE(21) lauryl ether | 19.0 |
| 6 | EMULGEN108 | POE lauryl ether | 12.1 |
| 7 | EMULGEN709 | POE alkyl ether | 13.3 |
| 8 | LS-106 | Polyoxyalkylene alkyl ether | 12.5 |

TABLE 11-continued

| No. | Product name | Chemical name | HLB |
|---|---|---|---|
| 9 | LS-110 | Polyoxyalkylene alkyl ether | 13.4 |
| 10 | EMULGEN1108 | POE alkyl ether | 13.4 |
| 11 | EMULGEN1118S-70 | POE alkyl ether | 16.4 |
| 12 | EMULGEN1150S-60 | POE alkyl ether | 18.5 |

Of these surfactants, No. 1 (Tx-100) was studied at two added concentrations of 0.1% and 0.5% in the R2 reagent. Surfactants Nos. 2 to 9 were added to the R2 reagent at a concentration of 0.5%, while Nos. 10 to 12 were added to the R2 reagent at a concentration of 0.1%.

(Samples and Activity Measurement)

The sample types, measurement equipment, measurement parameters and calculations of activity values were as in Example 2. The values for absorbance change per minute (sensitivity) (ΔmAbs/min) and the Lp-PLA$_2$ activity values (nmol/min/mL) using each buffer solution are shown in Tables 12 to 15, together with the relative activity values for each surfactant given 100 as the Lp-PLA$_2$ activity value using Tx-100.

TABLE 12

Individual serum 16
(surfactant concentration in R2 reagent: 0.5%)

| Surfactant | ΔmAbs/min | Activity value (nmol/min/mL) | Relative activity (%) |
|---|---|---|---|
| Tx-100 | 42.1 | 98.6 | 100 |
| BT-7 | 31.8 | 74.5 | 76 |
| BT-9 | 32.4 | 75.9 | 77 |
| BT-12 | 33.8 | 79.2 | 80 |
| BL-21 | 31.8 | 74.5 | 76 |
| EMULGEN108 | 20.6 | 48.3 | 49 |
| EMULGEN709 | 31.9 | 74.7 | 76 |
| LS-106 | 22.0 | 51.5 | 52 |
| LS-110 | 23.1 | 54.1 | 55 |

TABLE 13

Individual serum 78
(surfactant concentration in R2 reagent: 0.5%)

| Surfactant | ΔmAbs/min | Activity value (nmol/min/mL) | Relative activity (%) |
|---|---|---|---|
| Tx-100 | 19.2 | 45.0 | 100 |
| BT-7 | 14.1 | 33.0 | 73 |
| BT-9 | 15.0 | 35.1 | 78 |
| BT-12 | 15.2 | 35.6 | 79 |
| BL-21 | 14.4 | 33.7 | 75 |
| EMULGEN108 | 9.4 | 22.0 | 49 |
| EMULGEN709 | 14.3 | 33.5 | 74 |
| LS-106 | 10.5 | 24.6 | 55 |
| LS-110 | 10.5 | 24.6 | 55 |

TABLE 14

Individual serum 16
(surfactant concentration in R2 reagent: 0.1%)

| Surfactant | ΔmAbs/min | Activity value (nmol/min/mL) | Relative activity (%) |
|---|---|---|---|
| Tx-100 | 33.2 | 77.8 | 100 |
| EMULGEN1108 | 27.9 | 65.4 | 84 |

TABLE 14-continued

Individual serum 16
(surfactant concentration in R2 reagent: 0.1%)

| Surfactant | ΔmAbs/min | Activity value (nmol/min/mL) | Relative activity (%) |
|---|---|---|---|
| EMULGEN1118S-70 | 33.8 | 79.2 | 102 |
| EMULGEN1150S-60 | 32.4 | 75.9 | 98 |

TABLE 15

Individual serum 78
(surfactant concentration in R2 reagent: 0.1%)

| Surfactant | ΔmAbs/min | Activity value (nmol/min/mL) | Relative activity (%) |
|---|---|---|---|
| Tx-100 | 12.4 | 29.0 | 100 |
| EMULGEN1108 | 10.5 | 24.6 | 85 |
| EMULGEN1118S-70 | 13.4 | 31.4 | 108 |
| EMULGEN1150S-60 | 13.3 | 31.2 | 107 |

The measurement results in Tables 12 to 15 show that Lp-PLA$_2$ activity could be measured regardless of the surfactant used. Lp-PLA$_2$ activity could be measured with greater sensitivity using Tx-100, EMULGEN 1118S-70 and EMULGEN 1150S-60.

Example 8

<Investigating Surfactant Concentration in Lp-PLA$_2$ Measurement Reagents>

To study the effect of surfactant concentration in Lp-PLA$_2$ activity measurement reagents, EMULGEN 1118S-70 was used as the surfactant, the concentration of the EMULGEN 1118S-70 in the reagents was adjusted between 0 and 0.2%, and Lp-PLA$_2$ activity was measured in samples. The reagent compositions are as follows.

(Reagents of Invention)

<R1 Reagent>

| 50 mM | Tris-HCl (pH 7.5) |
|---|---|
| 1 mM | CaCl$_2$ |
| 4 U/mL | ASOM |
| 0% to 0.2% | EMULGEN 1118S-70 |
| 0.13 mg/mL | Recombinant lyso-PAF-PLD |
| 0.03% | TODB |
| 4 U/mL | Peroxidase |
| 5 U/mL | Recombinant choline oxidase III |

<R2 Reagent>

| 50 mM | Tris-HCl (pH 7.5) |
|---|---|
| 1 mM | CaCl$_2$ |
| 0.04% | 4-AA |
| 0% to 0.2% | EMULGEN 1118S-70 |
| 10 mM | Racemic PAF (C16) |

The sample types, measurement equipment, measurement parameters and calculations of activity values were as in Example 2. The values for absorbance change per minute (sensitivity) (ΔmAbs/min) and the Lp-PLA$_2$ activity values (nmol/min/mL) using each buffer solution are shown in Tables 16 to 18.

TABLE 16

Individual Serum 16

| Concentration (mM) | ΔmAbs/min | Activity value (nmol/min/mL) |
|---|---|---|
| 0 | 50.0 | 117.1 |
| 0.05 | 51.0 | 119.5 |
| 0.1 | 51.0 | 119.5 |
| 0.2 | 47.3 | 110.8 |

TABLE 17

Individual serum 78

| Concentration (mM) | ΔmAbs/min | Activity value (nmol/min/mL) |
|---|---|---|
| 0 | 22.1 | 51.8 |
| 0.05 | 22.4 | 52.5 |
| 0.1 | 21.8 | 51.1 |
| 0.2 | 20.3 | 47.6 |

TABLE 18

Pooled serum J042

| Concentration (mM) | ΔmAbs/min | Activity value (nmol/min/mL) |
|---|---|---|
| 0 | 23.3 | 54.6 |
| 0.05 | 24.1 | 56.5 |
| 0.1 | 24.3 | 56.9 |
| 0.2 | 21.9 | 51.3 |

The measurement results in Tables 16 to 18 show that Lp-PLA$_2$ activity could be measured at all concentrations of the surfactant. Lp-PLA$_2$ activity could be measured with higher sensitivity when the surfactant concentration was 0.1% or less.

Example 9

<Lp-PLA$_2$ Activity Measurement Using Various Substrates>

Lp-PLA$_2$ activity in samples was measured using optically active forms of the synthetic substrates PAF(C16) and PAF(C18), racemic PAF(C16), native PAF, and the PAF analog 1-palmitoyl-2-acetyl-sn-glycero-3-PC. The reagent compositions are as follows.

(Reagents of Invention)

Reagent compositions using substrates other than racemic PAF(C16)

<R1 Reagent>

| | |
|---|---|
| 50 mM | Tris-HCl (pH 7.5) |
| 1 mM | CaCl$_2$ |
| 4 U/mL | ASOM |
| 0.05% | EMULGEN 1150S-60 |
| 0.13 mg/mL | Recombinant lyso-PAF-PLD |
| 0.03% | TODB |
| 4 U/mL | Peroxidase |
| 5 U/mL | Recombinant choline oxidase III |

<R2 Reagent>

| | |
|---|---|
| 50 mM | Tris-HCl (pH 7.5) |
| 1 mM | CaCl$_2$ |
| 0.04% | 4-AA |
| 0.05% | EMULGEN 1150S-60 |
| 10 mM | Each substrate |

Reagent compositions using racemic PAF(C16) substrate

<R1 Reagent>

| | |
|---|---|
| 50 mM | Tris-HCl (pH 7.5) |
| 1 mM | CaCl$_2$ |
| 4 U/mL | ASOM |
| 0.05% | EMULGEN 1150S-60 |
| 0.13 mg/mL | Recombinant lyso-PAF-PLD |
| 0.03% | TODB |
| 4 U/mL | Peroxidase |
| 5 U/mL | Recombinant choline oxidase III |

<R2 Reagent>

| | |
|---|---|
| 50 mM | Tris-HCl (pH 7.5) |
| 1 mM | CaCl$_2$ |
| 0.04% | 4-AA |
| 0.05% | EMULGEN 1150S-60 |
| 0.13 mg/mL | Recombinant lyso-PAF-PLD |
| 4 U/mL | Peroxidase |
| 5 U/mL | Recombinant choline oxidase III |
| 10 mM | Racemic PAF(C16) |

(Samples)

Pooled serum J042, pooled serum C, individual serum 16, heparin pooled plasma, citrated pooled plasma, rLp-PLA$_2$ (0.017 mg/mL).

(Activity Measurement)

Activity was measured with a Hitachi 7080 automatic analyzer. The measurement parameters are shown below.

(Hitachi 7080 Automatic Analyzer Measurement Parameters)

| | |
|---|---|
| Analysis method | Rate A |
| Measurement wavelength (sub/dominant) | 660 nm/546 nm |
| Reaction time | 10 minutes |
| Measuring points | 27 to 30 |
| Sample volume | 5 μL |
| R1 reagent volume | 150 μL |
| R2 reagent volume | 100 μL |

5 μL of sample was mixed with 150 μL of the R1 reagent, and incubated for 5 minutes at 37° C. (measuring points 1 to 15), after which 100 μL of the R2 reagent was added to initiate a reaction (measuring point 16). The absorbance of water (blank) at the same measuring points was subtracted from the absorbance of the sample about 3.5 to 4.5 minutes after the reaction was initiated by addition of the R2 reagent (measuring points 27 to 30) to calculate the absorbance change per minute (ΔmAbs/min), and the Lp-PLA$_2$ activity value (nmol/min/mL) was calculated according to the previous formula. The values for absorbance change per minute (sensitivity) (ΔmAbs/min) and Lp-PLA$_2$ activity (nmol/min/mL) and the relative activity for each substrate given 100 as the Lp-PLA$_2$ activity value for PAF(C16) are shown in Tables 19 to 24.

TABLE 19

Pooled serum J042

| Substrate | ΔmAbs/min | Activity value (nmol/min/mL) | Relative activity (%) |
|---|---|---|---|
| PAF(C16) | 28.8 | 40.8 | 100 |
| PAF(C18) | 25.0 | 35.4 | 87 |
| Racemic PAF(C16) | 20.3 | 28.8 | 71 |
| Native PAF | 28.3 | 40.1 | 98 |
| 1-Palmitoyl-2-acetyl-sn-glycero-PC | 31.9 | 45.2 | 111 |

TABLE 20

Pooled serum C

| Substrate | ΔmAbs/min | Activity value (nmol/min/mL) | Relative activity (%) |
|---|---|---|---|
| PAF(C16) | 28.8 | 40.8 | 100 |
| PAF(C18) | 25.1 | 35.6 | 87 |
| Racemic PAF(C16) | 20.2 | 28.6 | 70 |
| Native PAF | 28.5 | 40.4 | 99 |
| 1-Palmitoyl-2-acetyl-sn-glycero-PC | 31.7 | 44.9 | 110 |

TABLE 21

Individual serum 16

| Substrate | ΔmAbs/min | Activity value (nmol/min/mL) | Relative activity (%) |
|---|---|---|---|
| PAF(C16) | 66.9 | 94.8 | 100 |
| PAF(C18) | 56.0 | 79.3 | 84 |
| Racemic PAF(C16) | 47.7 | 67.6 | 71 |
| Native PAF | 63.3 | 89.7 | 95 |
| 1-Palmitoyl-2-acetyl-sn-glycero-PC | 58.1 | 82.3 | 87 |

TABLE 22

Heparin pooled plasma

| Substrate | ΔmAbs/min | Activity value (nmol/min/mL) | Relative activity (%) |
|---|---|---|---|
| PAF(C16) | 31.3 | 44.3 | 100 |
| PAF(C18) | 27.3 | 38.7 | 87 |
| Racemic PAF(C16) | 22.2 | 31.5 | 71 |
| Native PAF | 30.8 | 43.6 | 98 |
| 1-Palmitoyl-2-acetyl-sn-glycero-PC | 31.1 | 44.1 | 99 |

TABLE 23

Citrated pooled plasma

| Substrate | ΔmAbs/min | Activity value (nmol/min/mL) | Relative activity (%) |
|---|---|---|---|
| PAF(C16) | 23.5 | 33.3 | 100 |
| PAF(C18) | 19.6 | 27.8 | 83 |
| Racemic PAF(C16) | 15.9 | 22.5 | 68 |
| Native PAF | 22.9 | 32.4 | 97 |
| 1-Palmitoyl-2-acetyl-sn-glycero-PC | 24.3 | 34.4 | 103 |

TABLE 24 rLp-PLA$_2$ (0.017 mg/mL)

| Substrate | ΔmAbs/min | Activity value (nmol/min/mL) | Relative activity (%) |
|---|---|---|---|
| PAF(C16) | 93.4 | 132.3 | 100 |
| PAF(C18) | 52.3 | 74.1 | 56 |
| Racemic PAF(C16) | 65.7 | 93.1 | 70 |
| Native PAF | 86.1 | 122.0 | 92 |
| 1-Palmitoyl-2-acetyl-sn-glycero-PC | 69.7 | 98.7 | 75 |

The measurement results in Tables 19 to 24 show that Lp-PLA$_2$ activity could be measured using any of the substrates. The main component of native PAF is C16, and Lp-PLA$_2$ activity could be measured with higher sensitivity by using the optically active form of C16 as the substrate.

Example 10

<Investigation of Trinder Reagents>

Types of Trinder reagents were studied to investigate whether Lp-PLA$_2$ activity could be measured using combinations other than TODB and 4-AA for the chromogenic reagent. Two kinds of Trinder reagents other than TODB were used: TOOS (product No. OC13, Dojindo Laboratories) and DAOS (product No. OC06, Dojindo Laboratories). Measurement was also performed with TODB for purposes of comparison.

The reagent compositions are as follows.
(Reagents of Invention)
<R1 Reagent>

| 50 mM | Tris-HCl (pH 7.5) |
|---|---|
| 1 mM | CaCl$_2$ |
| 4 U/mL | ASOM |
| 0.1% | Tx-100 |
| 0.13 mg/mL | Recombinant lyso-PAF-PLD |
| 0.03% | Trinder reagent |
| 4 U/mL | Peroxidase |
| 5 U/mL | Recombinant choline oxidase III |

<R2 Reagent>

| 50 mM | Tris-HCl (pH 7.5) |
|---|---|
| 1 mM | CaCl$_2$ |
| 0.04% | 4-AA |
| 0.1% | Tx-100 |
| 0.13 mg/mL | Recombinant lyso-PAF-PLD |
| 4 U/mL | Peroxidase |
| 5 U/mL | Recombinant choline oxidase III |
| 10 mM | Racemic PAF (C16) |

(Samples)

Individual serum No. 16, Individual serum No. 78, pooled serum J042.

(Activity Measurement)

The measurement parameters, measurement equipment and calculations of activity values were all as in Example 9, except that the sample volume was 3 μL in measurements using TOOS and TODB. In measurements using DAOS, the measurement parameters, measurement equipment and calculations of activity values were all as in Example 9 except that the sample volume was 3 μL and the measurement wavelength (sub/dominant) was 700 nm/600 nm. The values for absorbance change per minute (sensitivity) (ΔmAbs/ min) and Lp-PLA$_2$ activity (nmol/min/mL) in activity measurement using each Trinder reagent are shown in Table 25.

TABLE 25

| Sample | DAOS | | TOOS | | TODB | |
|---|---|---|---|---|---|---|
| | ΔmAbs/min | nmol/min/mL | ΔmAbs/min | nmol/min/mL | ΔmAbs/min | nmol/min/mL |
| Individual serum No16 | 14.4 | 33.7 | 29.6 | 69.3 | 30.3 | 71.0 |
| Individual serum No78 | 6.2 | 14.5 | 12.0 | 28.1 | 12.8 | 30.0 |
| Pooled serum J042 | 6.0 | 14.1 | 13.2 | 30.9 | 13.6 | 31.9 |

The measurement results show that measurement was possible with any combination. Using TOOS and TODB, the values for absorbance change (sensitivity) were about twice those obtained with DAOS, and the samples could be measured with greater sensitivity.

Example 11

<Reagent Composition Test 1 (R2 Reagent Formula with Lyso-PAF-PLD)>

To eliminate the acyl-lysophospholipids which are thought to be contained in concentrations of hundreds of μM in serum, enzymes having PLA$_1$ activity to decompose the first position acyl groups of phospholipids, and GPCP to hydrolyze the resulting GPC, were added together with choline oxidase to the R1 reagent, and the possibility of measuring Lp-PLA$_2$ activity in the presence of the R2 reagent containing lyso-PAF-PLD was investigated. MGLPII (T-117, Asahi Kasei Pharma Corporation) and LYPL (T-32, Asahi Kasei Pharma Corporation) were used as the enzymes having PLA$_1$ activity. The GPCP prepared in Reference Examples 7 to 9 was used as the *E. coli*-derived GPCP in the R1 reagent. The compositions of the reagents are as follows.

(Reagents of Invention)
<R1 Reagent>

| | |
|---|---|
| 50 mM | Tris-HCl (pH 7.5) |
| 1 mM | CaCl$_2$ |
| 4 U/mL | ASOM |
| 0.1% | Tx-100 |
| 50 U/mL | MGLPII or 10 U/mL LYPL |
| 0.19 mg/mL | *E. coli*-derived recombinant GPCP |
| 0.03% | TODB |
| 4 U/mL | Peroxidase |
| 5 U/mL | Recombinant choline oxidase III |

<R2 Reagent>

| | |
|---|---|
| 50 mM | Tris-HCl (pH 7.5) |
| 1 mM | CaCl$_2$ |
| 0.13 mg/mL | Lyso-PAF-PLD |
| 0.04% | 4-AA |
| 0.1% | Tx-100 |
| 4 U/mL | Peroxidase |
| 5 U/mL | Recombinant choline oxidase III |
| 10 mM | Racemic PAF (C16) |

(Samples and Activity Measurement)

The sample types were as in Example 10, and the measurement equipment, measurement parameters and calculations of activity values were as in Example 9. The measurement results are shown in Table 26.

TABLE 26

| Sample | MGLPII | | LYPL | |
|---|---|---|---|---|
| | ΔmAbs/min | nmol/min/mL | ΔmAbs/min | nmol/min/mL |
| Individual serum No16 | 30.7 | 71.9 | 25.3 | 59.3 |
| Individual serum No78 | 13.9 | 32.6 | 12.2 | 28.6 |
| Pooled serum J042 | 14.6 | 34.2 | 12.7 | 29.8 |

The measurement results in Table 26 and the results for TODB in Table 25 with lyso-PAF-PLD formulated in the R1 reagent show that even when lyso-PAF-PLD is only contained in the R2 reagent, Lp-PLA$_2$ activity can be measured as if lyso-PAF-PLD were contained in the R1 reagent if MGLPII and GPCP are added to the R1 reagent. Measurement was also possible when LYPL and GPCP were added to the R1 reagent.

Example 12

<Reagent Composition Test 2 (R2 Formula with Choline Oxidase)>

We investigated whether Lp-PLA$_2$ activity could be measured without a preliminary step to eliminate choline from the sample, or in other words with choline oxidase contained in the R2 reagent. The compositions of the reagents are as follows.

(Reagents of Invention)
<R1 Reagent>

| | |
|---|---|
| 50 mM | Tris-HCl (pH 7.5) |
| 1 mM | CaCl$_2$ |
| 4 U/mL | ASOM |
| 0.1% | Tx-100 |
| 0.13 mg/mL | Lyso-PAF-PLD |
| 0.03% | TODB |
| 4 U/mL | Peroxidase |

<R2 Reagent>

| | |
|---|---|
| 50 mM | Tris-HCl (pH 7.5) |
| 1 mM | CaCl$_2$ |
| 0.1% | Tx-100 |
| 0.04% | 4-AA |
| 4 U/mL | Peroxidase |
| 0.13 mg/mL | Lyso-PAF-PLD |
| 5 U/mL | Recombinant choline oxidase III |
| 10 mM | Racemic PAF (C16) |

(Samples and Activity Measurement)

The sample types were as in Example 10, and the measurement equipment, measurement parameters and calculations of activity values were as in Example 9. The measurement results are shown in Table 27.

TABLE 27

| Sample | ΔmAbs/min | nmol/min/mL |
|---|---|---|
| Individual serum No16 | 36.8 | 86.2 |
| Individual serum No78 | 13.4 | 31.4 |
| Pooled serum J042 | 16.3 | 38.2 |

The measurement results in Table 27 show that Lp-PLA$_2$ activity could be measured even when choline oxidase was contained only in the R2 reagent. However, the measurement values were higher in the TODB results from Table 25 with choline oxidase contained in the R1 reagent and R2 reagent. This may be attributable to the effect of residual choline in the sample.

Example 13

<Investigation of S/R Ratio in Lp-PLA$_2$ Measurement>

Lp-PLA$_2$ activity was measured with different sample volumes to investigate the S/R ratio in the reagents of the invention. The reagent compositions are shown below.

(Reagents of Invention)
<R1 Reagent>

| 50 mM | Tris-HCl (pH 7.8) |
|---|---|
| 1 mM | CaCl$_2$ |
| 3 U/mL | ASOM |
| 0.1% | Tx-100 |
| 0.13 mg/mL | Recombinant lyso-PAF-PLD |
| 0.0225% | TODB |
| 4 U/mL | Peroxidase |
| 5 U/mL | Recombinant choline oxidase III |

<R2 Reagent>

| 50 mM | PIPES (pH 7.0) |
|---|---|
| 1 mM | CaCl$_2$ |
| 0.08% | 4-AA |
| 0.1% | Tx-100 |
| 0.26 mg/mL | Recombinant lyso-PAF-PLD |
| 4 U/mL | Peroxidase |
| 5 U/mL | Recombinant choline oxidase III |
| 20 mM | Racemic PAF (C16) |

(Samples)
Pooled serum J042.
(Activity Measurement)
A Hitachi 7080 automatic analyzer was used to measure activity. The measurement parameters are shown below.
(Hitachi 7080 Automatic Analyzer Measurement Parameters)

| Analysis method | Rate A |
|---|---|
| Measurement wavelength (sub/dominant) | 660 nm/546 nm |
| Reaction time | 10 minutes |
| Measuring points | 27 to 30 |
| Sample volume | 2, 4, 6 μL |
| R1 reagent volume | 160 μL |
| R2 reagent volume | 40 μL |

Each sample was mixed with 160 μL of the R1 reagent, and incubated for 5 minutes at 37° C., (measuring points 1 to 15), after which 40 μL of the R2 reagent was added to initiate the reaction (measuring point 16). The absorbance of water (blank) at the same measuring points was subtracted from the absorbance of the sample about 3.5 to 4.5 minutes after the reaction was initiated by addition of the R2 reagent (measuring points 27 to 30) to calculate the absorbance change per minute (ΔmAbs/min), and the Lp-PLA$_2$ activity value (nmol/min/mL) was calculated according to the previous formula. The values for absorbance change per minute (sensitivity) (ΔmAbs/min) and Lp-PLA$_2$ activity (nmol/min/mL) are shown in Table 28.

TABLE 28

| Sample volume | ΔmAbs/min | nmol/min/mL |
|---|---|---|
| 2 μL | 10.0 | 28.1 |
| 4 μL | 21.2 | 30.0 |
| 6 μL | 34.8 | 33.2 |

Measurement was possible with a sample volume of 2 μL (S:R=1:100), a sample volume of 4 μL (S:R=1:50) or a sample volume of 6 μL (S:R=1:33).

Example 14

<Lp-PLA$_2$ Spike and Recovery Test in Serum>

Using serum samples that exhibited Lp-PLA$_2$ activity and a serum sample that exhibited no Lp-PLA$_2$ activity, 0 to 33.2 μg/mL of rLp-PLA$_2$ was added to each sample, activity was measured, and the recovery rate was determined. The reagent compositions are as in Example 13.

(Samples)

For the samples, 0, 3.3, 6.6, 13.3, 16.6 and 33.2 μg/mL each of rLp-PLA$_2$ was added to 4 kinds of pools, i.e., the pooled serum J042 and to the pooled serums A, B and C. The pooled serum A is a serum sample that exhibits no Lp-PLA$_2$ activity.

(Activity Measurement)

The sample volume was 4 μL, and the measurement equipment, the measurement parameters other than sample volume, and the calculations of activity values were as in Example 13. The recovery rate was calculated by the following formula.

Recovery rate (%) =

{(activity value of serum with added rLp-PLA$_2$) − (activity value of serum alone)}/(activity value of pooled serum A(serum exhibiting no Lp-PLA$_2$ activity)

with added rLp-PLA$_2$) × 100 =

(activity value of added rLp-PLA$_2$)/

(activity value of rLp-PLA$_2$ added to pooled serum A) × 100

The absorbance change per minute in each sample (ΔmAbs/min), the activity value when rLp-PLA$_2$ was added at each concentration (nmol/min/mL), the activity value of the added rLp-PLA$_2$ (nmol/min/mL) and the recovery rate (%) are shown in Tables 29 to 31. FIGS. 4 to 7 show the added rLp-PLA$_2$ concentration (μg/mL) plotted on the x-axis, and the absorbance change per minute on the y-axis.

TABLE 29

Pooled serum J042

| Added concentration of rLp-PLA$_2$ (μg/mL) | Absorbance change (ΔmAbs/min) | Activity value with rLp-PLA$_2$ added to serum (nmol/min/mL) | Activity value of added rLp-PLA$_2$ (nmol/min/mL) | Recovery rate (%) |
|---|---|---|---|---|
| 0 | 20.0 | 28.3 | | |
| 3.3 | 29.9 | 42.4 | 14.0 | 96.1 |
| 6.6 | 40.0 | 56.7 | 28.3 | 94.3 |
| 13.2 | 61.7 | 87.4 | 59.1 | 101.0 |
| 16.6 | 76.2 | 108.0 | 79.6 | 110.6 |
| 33.2 | 123.8 | 175.4 | 147.1 | 101.3 |

TABLE 30

Pooled serum B

| Added concentration of rLp-PLA$_2$ (μg/mL) | Absorbance change (ΔmAbs/min) | Activity value with rLp-PLA$_2$ added to serum (nmol/min/mL) | Activity value of added rLp-PLA$_2$ (nmol/min/mL) | Recovery rate (%) |
|---|---|---|---|---|
| 0 | 20.3 | 28.8 | | |
| 3.3 | 29.7 | 42.1 | 13.3 | 91.3 |
| 6.6 | 42.1 | 59.6 | 30.9 | 102.8 |
| 13.2 | 61.3 | 86.8 | 58.1 | 99.3 |
| 16.6 | 72.4 | 102.6 | 73.8 | 102.6 |
| 33.2 | 123.9 | 175.5 | 146.8 | 101.1 |

TABLE 31

• Pooled serum C

| Added concentration of rLp-PLA$_2$ (μg/mL) | Absorbance change (ΔmAbs/min) | Activity value with rLp-PLA$_2$ added to serum (nmol/min/mL) | Activity value of added rLp-PLA$_2$ (nmol/min/mL) | Recovery rate (%) |
|---|---|---|---|---|
| 0 | 19.8 | 28.1 | | |
| 3.3 | 29.6 | 41.9 | 13.9 | 95.1 |
| 6.6 | 40.0 | 56.7 | 28.6 | 95.3 |
| 13.2 | 60.5 | 85.7 | 57.7 | 98.5 |
| 16.6 | 72.4 | 102.6 | 74.5 | 103.5 |
| 33.2 | 123.4 | 174.8 | 146.8 | 101.1 |

The measurement results in FIGS. 4 to 7 show absorbance changes to be dependent on rLp-PLA$_2$ concentration, and Tables 29 to 31 show roughly 100%±10% recovery.

Example 15

<Comparison of Measurement Values with Cayman Chemical Company PAF Acetylhydrolase Assay Kit and Reagents of Invention>

Lp-PLA$_2$ activity was measured using the reagents of the invention and a Cayman Chemical Company PAF Acetylhydrolase Assay Kit. Activity measurement with the Cayman Co. reagent was performed in accordance with the package insert, and the activity values were also calculated in accordance with the package insert. The reagent compositions are as follows.

(Reagents of Invention)
<R1 Reagent>

| 50 mM | Tris-HCl (pH 7.5) |
|---|---|
| 1 mM | CaCl$_2$ |
| 4 U/mL | ASOM |
| 0.1% | Tx-100 |
| 0.26 mg/mL | Recombinant lyso-PAF-PLD |
| 0.03% | TODB |
| 4 U/mL | Peroxidase |
| 5 U/mL | Recombinant choline oxidase |

<R2 Reagent>

| 50 mM | Tris-HCl (pH 7.5) |
|---|---|
| 1 mM | CaCl$_2$ |
| 0.04% | 4-AA |
| 0.1% | Tx-100 |
| 10 mM | PAF (C16) |

(Samples)
Individual serums Nos. 1 to 32.
(Activity Measurement)
A SpectraMax M3 (Molecular Devices, LLC.) microplate reader was used for measuring activity with the Cayman Co. reagents. A Hitachi 7600-010S automatic analyzer was used to for measuring activity by the method of the invention. The measurement parameters are shown below.

| Analysis method | Rate A |
|---|---|
| Measurement wavelength (sub/dominant) | 660 nm/546 nm |
| Reaction time | 10 minutes |
| Measuring points | 25 to 28 |
| Sample volume | 3 μL |
| R1 reagent volume | 150 μL |
| R2 reagent volume | 100 μL |

3 μL of sample was mixed with 150 μL of the R1 reagent, and incubated for 5 minutes at 37° C. (measuring points 1 to 16), after which 100 μL of the R2 reagent was added to initiate a reaction (measuring point 17). The absorbance of water (blank) at the same measuring points was subtracted from the absorbance of the sample about 2 to 3 minutes after the reaction was initiated by addition of the R2 reagent (measuring points 25 to 28) to calculate the absorbance change per minute (ΔmAbs/min), and the Lp-PLA$_2$ activity value (nmol/min/mL) was calculated according to the previous formula. The Lp-PLA$_2$ activity values (nmol/min/mL) for the method of the invention and the Cayman Co. reagents are shown in Table 32 (chyle specimens are marked +, and the chyle degree was indicated by the number of +'s). The activity values obtained with the Cayman Co. reagents (x-axis (nmol/min/mL)) and the activity values obtained by the method of the invention (y-axis (nmol/min/mL)) are compared in FIG. 8.

TABLE 32

| Sample | Chyle | Cayman reagents (nmol/min/mL) | Reagents of invention (nmol/min/mL) |
|---|---|---|---|
| Individual serum No. 1 | ++ | 28.7 | 43.2 |
| Individual serum No. 2 | + | 27.6 | 42.2 |
| Individual serum No. 3 | + | 20.5 | 54.0 |
| Individual serum No. 4 | + | 24.4 | 61.7 |
| Individual serum No. 5 | + | 21.5 | 48.4 |
| Individual serum No. 6 | + | 18.2 | 42.8 |

TABLE 32-continued

| Sample | Chyle | Cayman reagents (nmol/min/mL) | Reagents of invention (nmol/min/mL) |
|---|---|---|---|
| Individual serum No. 7 | + | 11.4 | 24.3 |
| Individual serum No. 8 | + | 20.0 | 50.6 |
| Individual serum No. 9 | + | 25.3 | 65.0 |
| Individual serum No. 10 | + | 23.2 | 57.0 |
| Individual serum No. 11 | + | 20.7 | 55.9 |
| Individual serum No. 12 |  | 19.6 | 49.1 |
| Individual serum No. 13 | + | 25.2 | 73.4 |
| Individual serum No. 14 | + | 17.0 | 46.3 |
| Individual serum No. 15 | + | 18.9 | 47.8 |
| Individual serum No. 16 | ++ | 36.8 | 99.0 |
| Individual serum No. 17 | +++ | 13.2 | 52.5 |
| Individual serum No. 18 | + | 21.2 | 52.7 |
| Individual serum No. 19 | + | 19.6 | 28.6 |
| Individual serum No. 20 |  | 19.0 | 46.7 |
| Individual serum No. 21 | + | 15.0 | 36.1 |
| Individual serum No. 22 | + | 27.6 | 68.6 |
| Individual serum No. 23 | + | 27.5 | 63.9 |
| Individual serum No. 24 |  | 20.7 | 55.1 |
| Individual serum No. 25 |  | 24.3 | 59.2 |
| Individual serum No. 26 | + | 27.8 | 77.4 |
| Individual serum No. 27 | + | 25.5 | 64.3 |
| Individual serum No. 28 | + | 34.5 | 84.5 |
| Individual serum No. 29 | + | 16.6 | 40.2 |
| Individual serum No. 30 | + | 14.3 | 31.4 |
| Individual serum No. 31 |  | 20.2 | 43.0 |
| Individual serum No. 32 | + | 23.5 | 45.0 |

Based on these measurement results, the correlation between the measurement values (nmol/min/mL) measured in these samples with the Cayman Co. reagents and reagents of the invention can be represented as correlation equation y=2.254x+3.4656, correlation coefficient r=0.805 (FIG. 8).

This example shows that Lp-PLA$_2$ activity in individual serum can be measured with a correlation of r=0.805 between the reagents of the invention and the Cayman Co. reagents. Because the reagents of the invention are used with a general-purpose automatic analyzer, they would seem to be more practical as diagnostic agents than the Cayman Co. reagents, which are used with 96-well plates.

Because the activity values are defined differently, the measured activity values are different between the Cayman Co. reagents and the reagents of the invention, and the slope of the correlation equation is not 1, but it is thought that the slope of the correlation equation would approach 1 if the activity value definitions and calibrator values were identical.

Example 16

<Comparison of Measurement Values Obtained by Measuring Samples with R&D Systems Human PLA2G7/PAF-AH/Lp-PLA$_2$ Quantikine ELISA Kit and Reagents of Invention>

The substance quantity of Lp-PLA$_2$ was assayed using an R&D Systems Human PLA2G7/PAF-AH/Lp-PLA$_2$ Quantikine ELISA Kit in accordance with the package insert.

(Activity Measurement)

A SpectraMax M3 (Molecular Device Japan) microplate reader was used for the R&D Systems kit assay. The Lp-PLA$_2$ activity values (nmol/min/mL) measured in Example 15 with the reagents of the invention and the Lp-PLA$_2$ amounts (ng/mL) measured with the R&D Systems Kit are shown in Table 33. FIG. 9 shows a comparison of the assay values (x-axis (ng/mL)) obtained with the R&D Systems Kit and the activity values (y-axis (nmol/min/mL)) obtained with the reagents of the invention.

TABLE 33

| Sample | Chyle | R & D Systems Kit (ng/mL) | Reagents of invention (nmol/min/mL) |
|---|---|---|---|
| Individual serum No. 1 | ++ | 137.3 | 43.2 |
| Individual serum No. 2 | + | 129.7 | 42.2 |
| Individual serum No. 3 | + | 140.6 | 54.0 |
| Individual serum No. 4 | + | 157.0 | 61.7 |
| Individual serum No. 5 | + | 116.9 | 48.4 |
| Individual serum No. 6 | + | 115.2 | 42.8 |
| Individual serum No. 7 | + | 63.8 | 24.3 |
| Individual serum No. 8 | + | 132.2 | 50.6 |
| Individual serum No. 9 | + | 150.1 | 65.0 |
| Individual serum No. 10 | + | 134.7 | 57.0 |
| Individual serum No. 11 | + | 138.7 | 55.9 |
| Individual serum No. 12 |  | 91.0 | 49.1 |
| Individual serum No. 13 | + | 174.0 | 73.4 |
| Individual serum No. 14 | + | 86.8 | 46.3 |
| Individual serum No. 15 | + | 120.6 | 47.8 |
| Individual serum No. 16 | ++ | 249.4 | 99.0 |
| Individual serum No. 17 | +++ | 119.5 | 52.5 |
| Individual serum No. 18 | + | 111.7 | 52.7 |
| Individual serum No. 19 | + | 118.6 | 28.6 |
| Individual serum No. 20 |  | 99.8 | 46.7 |
| Individual serum No. 21 | + | 12.0 | 36.1 |
| Individual serum No. 22 | + | 141.1 | 68.6 |
| Individual serum No. 23 | + | 139.8 | 63.9 |
| Individual serum No. 24 |  | 121.9 | 55.1 |
| Individual serum No. 25 |  | 128.0 | 59.2 |
| Individual serum No. 26 | + | 133.2 | 77.4 |
| Individual serum No. 27 | + | 71.8 | 64.3 |
| Individual serum No. 28 | + | 183.6 | 84.5 |
| Individual serum No. 29 | + | 73.7 | 40.2 |
| Individual serum No. 30 | + | 67.8 | 31.4 |

TABLE 33-continued

| Sample | Chyle | R & D Systems Kit (ng/mL) | Reagents of invention (nmol/min/mL) |
|---|---|---|---|
| Individual serum No. 31 | | 75.4 | 43.0 |
| Individual serum No. 32 | + | 87.0 | 45.0 |

Based on these measurement results, the correlation between the measurement values (ng/mL) obtained with the R&D Systems Human PLA2G7/PAF-AH/Lp-PLA$_2$ Quantikine ELISA Kit and the measurement values (nmol/min/mL) obtained by the method of the invention can be represented as correlation equation y=0.2917x+18.582, correlation coefficient r=0.800 (FIG. 9).

This example shows that individual serum can be measured with the reagent of the invention with a correlation of r=0.800 with the measurement values obtained with an R&D Systems Human PLA2G7/PAF-AH/Lp-PLA$_2$ Quantikine ELISA Kit. The measurement values obtained with the R&D Systems Human PLA2G7/PAF-AH/Lp-PLA$_2$ Quantikine ELISA Kit are amounts of Lp-PLA$_2$, and thus differ from the measurement values obtained with the reagents of the invention because they are not activity values.

Example 17

<Measuring Absorbance Change Values and Lp-PLA$_2$ Activity Values of Reagents of Invention>

The absorbance change values per minute (sensitivity, ΔmAbs/min) and Lp-PLA$_2$ activity values (nmol/min/mL) of the reagents of the invention were measured.

For reference purposes, Lp-PLA$_2$ activity was also measured using diaDexus PLAC Test for Lp-PLA$_2$ Activity (PLAC Test) and Diasys Co. Diasys Lp-PLA$_2$ FS (Lp-PLA$_2$ FS). The measurement wavelengths in the PLAC Test and Lp-PLA$_2$ FS were 415 nm. The reagent compositions used in the method of the invention were as follows.

(Reagents of Invention)
<R1 Reagent>

| | |
|---|---|
| 50 mM | Tris-HCl (pH 7.5) |
| 1 mM | CaCl$_2$ |
| 4 U/mL | ASOM |
| 0.05% | EMULGEN 1150S-60 |
| 0.13 mg/mL | Recombinant lyso-PAF-PLD |
| 25 μM | Potassium ferrocyanide |
| 0.05% | ProClin 300 |
| 0.03% | TODB |
| 4 U/mL | Peroxidase |
| 5 U/mL | Recombinant choline oxidase III |

<R2 Reagent>

| | |
|---|---|
| 50 mM | Tris-HCl (pH 7.5) |
| 1 mM | CaCl$_2$ |
| 0.05% | EMULGEN 1150S-60 |
| 0.13 mg/mL | Recombinant lyso-PAF-PLD |
| 0.05% | ProClin 300 |
| 4 U/mL | Peroxidase |
| 5 U/mL | Recombinant choline oxidase III |
| 0.04% | 4-AA |
| 10 mM | Racemic PAF (C16) |

(Samples)

Water, 5 PLAC Test calibrators (0 nmol/min/mL (Calib 1), 50 nmol/min/mL (Calib 2), 100 nmol/min/mL (Calib 3), 250 nmol/min/mL (Calib 4) and 400 nmol/min/mL (Calib 5)), separately sold Lp-PLA$_2$ FS calibrator (TruCal Lipid, 447 U/L).

(Activity Measurement)

Activity was measured with a Hitachi 7600-010S automatic analyzer. The measurement parameters for each reagent were as follows.

(Hitachi 7600-010S Automatic Analyzer Measurement Parameters)

(Activity Measurement Parameters with Reagents of Invention)

| | |
|---|---|
| Analysis method | Rate A |
| Measurement wavelength (sub/dominant) | 660 nm/546 nm |
| Reaction time | 10 minutes |
| Measuring points | 29 to 32 |
| Sample volume | 5 μL |
| R1 reagent volume | 150 μL |
| R2 reagent volume | 50 μL |

To measure activity with the reagents of the invention, 5 μL of sample was mixed with 150 μL of the R1 reagent, and incubated for 5 minutes at 37° C. (measuring points 1 to 16), after which 100 μL of the R2 reagent was added to initiate a reaction (measuring point 17). The absorbance of water (blank) at the same measuring points was subtracted from the absorbance of the sample about 3.5 to 4.5 minutes after the reaction was initiated by addition of the R2 reagent (measuring points 29 to 32) to calculate the absorbance change per minute (ΔmAbs/min), and the Lp-PLA$_2$ activity value (nmol/min/mL) was calculated according to the previous formula.

(PLAC Test Measurement Parameters)

| | |
|---|---|
| Analysis method | Rate A |
| Measurement wavelength (sub/dominant) | 505 nm/415 nm |
| Reaction time | 10 minutes |
| Measuring points | 19 to 22 |
| Sample volume | 30 μL |
| R1 reagent volume | 120 μL |
| R2 reagent volume | 30 μL |

To measure activity by the PLAC Test, 30 μL of sample was mixed with 120 μL of the R1 reagent, and incubated for 5 minutes at 37° C. (measuring points 1 to 16), after which 30 pt of the R2 reagent was added to initiate a reaction (measuring point 17). The absorbance of water (blank) at the same measuring points was subtracted from the absorbance of the sample about 0.5 to 2 minutes after the reaction was initiated by addition of the R2 reagent (measuring points 19 to 22) to calculate the absorbance change per minute (ΔmAbs/min). The Lp-PLA$_2$ activity values (nmol/min/mL) were calculated according to the following formula, which was derived by plotting the absorbance change values per minute of the 5 PLAC Test calibrators on the x axis and the activity values on the y axis.

$$y=0.0013x^2+0.5292x-0.3213$$

(Lp-PLA₂ FS Measurement Parameters)

| Analysis method | Rate A |
|---|---|
| Measurement wavelength (sub/dominant) | 505 nm/415 nm |
| Reaction time | 10 minutes |
| Measuring points | 22 to 30 |
| Sample volume | 2 μL |
| R1 reagent volume | 200 μL |
| R2 reagent volume | 50 μL |

To measure activity with Lp-PLA₂ FS, 2 μL of sample was mixed with 200 μL of the R1 reagent, and incubated for 5 minutes at 37° C. (measuring points 1 to 16), after which 50 μL of the R2 reagent was added to initiate a reaction (measuring point 17). The absorbance of water (blank) at the same measuring points was subtracted from the absorbance of the sample about 2 to 4 minutes after the reaction was initiated by addition of the R2 reagent (measuring points 22 to 30) to calculate the absorbance change per minute (ΔmAbs/min). The Lp-PLA₂ activity values (U/L) were calculated according to the following formula in accordance with the Lp-PLA₂ FS package insert.

$$Lp\text{-}PLA_2 \text{ activity value } (U/L) =$$
$$\{(\Delta Abs/min.\ Sample)/(\Delta Abs/min.\ Cal.)\} \times Conc.\ Cal.(U/L) =$$
$$\{(\text{sample absorbance change per minute})/$$
$$(\text{calibrator absorbance change per minute})\} \times$$
$$\text{calibrator concentration}(447\ U/L)$$

The values for absorbance change per minute (ΔmAbs/min) and the activity values (nmol/min/mL and U/L) in each sample are shown in Tables 34 to 36.

TABLE 34

• Reagents of invention

| Sample | ΔmAbs/min | nmol/min/mL |
|---|---|---|
| PLAC Test Calib 1 | 0.7 | 1.0 |
| PLAC Test Calib 2 | 3.0 | 4.3 |
| PLAC Test Calib 3 | 6.2 | 8.8 |
| PLAC Test Calib 4 | 15.8 | 22.4 |
| PLAC Test Calib 5 | 26.3 | 37.3 |
| TruCal Lipid | 83.1 | 118 |

TABLE 35

• PLAC Test

| Sample | ΔmAbs/min | nmol/min/mL |
|---|---|---|
| PLAC Test Calib 1 | 6.3 | 0 (Specified value) |
| PLAC Test Calib 2 | 75.2 | 50 (Specified value) |
| PLAC Test Calib 3 | 136.9 | 100 (Specified value) |
| PLAC Test Calib 4 | 284.4 | 250 (Specified value) |
| PLAC Test Calib 5 | 384.6 | 400 (Specified value) |
| TruCal Lipid | 183.0 | 140 |

TABLE 36

• Lp-PLA₂ FS

| Sample | ΔmAbs/min | nmol/min/mL |
|---|---|---|
| PLAC Test Calib 1 | 0.7 | 8.5 |
| PLAC Test Calib 2 | 5.3 | 64.0 |
| PLAC Test Calib 3 | 9.8 | 118 |
| PLAC Test Calib 4 | 23.0 | 278 |
| PLAC Test Calib 5 | 36.5 | 441 |
| TruCal Lipid | 37.0 | 447 (Specified value) |

This example shows that the PLAC Test Calibrators 1 to 5 and the Lp-PLA₂ FS calibrator (TruCal Lipid) could be measured with the reagents of the invention.

Example 18

<Comparing within-Run Reproducibility of Reagents of Invention, PLAC Test and Lp-PLA₂ FS>

To compare the within-run reproducibility of the reagents of invention, PLAC Test and Lp-PLA₂ FS, Lp-PLA₂ activity was measured with n=5. The reagent compositions were the same as in Example 17.

(Samples)

PLAC Test CONTROL LOW (MEAN: 118.8 nmol/min/mL) (hereunder called PLAC CONT-L) and CONTROL HIGH (MEAN: 298.3 nmol/min/mL) (hereunder called PLAC CONT-H), pooled serum J042, Consera (Nissui Pharmaceutical Co., Ltd.).

(Activity Measurement)

The activity measurement equipment, measurement parameters and calculations of activity values were the same as in Example 17.

The values of for absorbance change per minute (sensitivity) (ΔmAbs/min), average values (AVE), standard deviations (SD), coefficients of variation (CV %) and activity values (nmol/min/mL and U/L) using the different reagents are shown in Tables 37 to 42. FIGS. 10 to 12 show reaction time courses obtained by plotting absorbance at each measuring point during the 10-minute reaction time using the pooled serum J042 as the sample.

TABLE 37

• Reagents of invention

| | ΔmAbs/min | | | | |
|---|---|---|---|---|---|
| Sample | n = 1 | n = 2 | n = 3 | n = 4 | n = 5 |
| PLAC CONT-L | 7.4 | 7.4 | 7.3 | 7.1 | 7.4 |
| PLAC CONT-H | 19.1 | 19.2 | 18.7 | 19.4 | 19.0 |
| Pooled serum J042 | 23.8 | 24.8 | 24.7 | 24.5 | 24.6 |
| Consera | 19.5 | 19.8 | 20.0 | 20.2 | 19.8 |

TABLE 38

• Reagents of invention

| Sample | SD | AVE | CV % | nmol/min/mL |
|---|---|---|---|---|
| PLAC CONT-L | 0.1 | 7.3 | 1.8 | 10.4 |
| PLAC CONT-H | 0.3 | 19.1 | 1.4 | 27.0 |

TABLE 38-continued

| | • Reagents of invention | | | |
|---|---|---|---|---|
| Sample | SD | AVE | CV % | nmol/min/mL |
| Pooled serum J042 | 0.4 | 24.5 | 1.6 | 34.7 |
| Consera | 0.3 | 19.9 | 1.3 | 28.1 |

TABLE 39

| | • PLAC Test | | | | |
|---|---|---|---|---|---|
| | ΔmAbs/min | | | | |
| Sample | n = 1 | n = 2 | n = 3 | n = 4 | n = 5 |
| PLAC CONT-L | 152.4 | 151.9 | 151.8 | 153.1 | 152.8 |
| PLAC CONT-H | 325.5 | 323.1 | 321.8 | 323.5 | 321.9 |
| Pooled serum J042 | 189.7 | 186.5 | 188.1 | 189.8 | 191.9 |
| Consera | 174.8 | 176.2 | 175.4 | 177.0 | 177.0 |

TABLE 40

| | • PLAC Test | | | |
|---|---|---|---|---|
| Sample | SD | AVE | CV % | nmol/min/mL |
| PLAC CONT-L | 0.6 | 152.4 | 0.4 | 110.5 |
| PLAC CONT-H | 1.5 | 323.2 | 0.5 | 306.5 |
| Pooled serum J042 | 2.0 | 189.2 | 1.1 | 146.3 |
| Consera | 1.0 | 176.1 | 0.6 | 133.2 |

TABLE 41

| | • Lp-PLA$_2$ FS | | | | |
|---|---|---|---|---|---|
| | ΔmAbs/min | | | | |
| Sample | n = 1 | n = 2 | n = 3 | n = 4 | n = 5 |
| PLAC CONT-L | 10.6 | 10.2 | 11.2 | 10.5 | 11.4 |
| PLAC CONT-H | 26.7 | 26.5 | 27.2 | 26.8 | 26.6 |
| Pooled serum J042 | 32.3 | 32.3 | 32.5 | 32.5 | 32.5 |
| Consera | 26.5 | 26.5 | 26.4 | 26.7 | 26.6 |

TABLE 42

| | • Lp-PLA$_2$ FS | | | |
|---|---|---|---|---|
| Sample | SD | AVE | CV % | U/L |
| PLAC CONT-L | 0.5 | 10.8 | 4.7 | 130.2 |
| PLAC CONT-H | 0.3 | 26.8 | 1.0 | 323.3 |
| Pooled serum J042 | 0.1 | 32.4 | 0.3 | 391.7 |
| Consera | 0.1 | 26.5 | 0.4 | 320.6 |

The measurement results show that with the reagents of the invention, the CV % of the measurement values was within ±2.0. With the PLAC Test, the CV % of the measurement values was around ±1.0. With Lp-PLA$_2$ FS, the CV % was 4.7 in the case of PLAC CONT-L, which was higher than the other samples, but the CV % of the other samples was within ±1.0.

This example shows that PLAC Test control serum, a purchased pooled serum, and a commercial controlled serum (Consera) could be measured with the reagents of the invention with a CV (%) equivalent to that obtained with the PLAC Test and Lp-PLA$_2$ FS.

Example 19

<Comparing Effects of Coexisting Substances with Reagents of Invention, PLAC Test and Lp-PLA$_2$ FS>

Samples were prepared with added Interference Check A Plus (Sysmex Corporation), Intralipos Infusion 10% (Otsuka Pharmaceutical Co., Ltd.) or ascorbic acid, and the effects of coexisting substances were investigated. The reagent compositions were the same as in Example 17.

(Samples)

Bilirubin-C (Bil-C) (209 mg/dL), bilirubin-F (Bil-F) (201 mg/dL), hemolytic hemoglobin (Hb) (5200 mg/dL) and chyle (14800 FTU) (all contained in Interference Check A Plus); Intralipos Infusion 10%; 0.5 g/dL ascorbic acid; and water (total 7) were mixed at a rate of 1:9 with pooled serum J042 (in this Example 40 μL of 7 substances+360 μL of pooled serum J042).

(Activity Measurement)

The activity measurement equipment, measurement parameters and calculations of activity values were the same as in Example 17.

The absorbance change values per minute (ΔmAbs/min) and activity values (nmol/min/mL and U/L) with each kind of reagent are shown in Tables 43 to 45. Given 100% as the measurement value of the sample with the added water, the measurement values for the other samples are shown as percentages.

TABLE 43

| • Reagents of invention | | | |
|---|---|---|---|
| Sample | ΔmAbs/min | nmol/min/mL | % |
| J042 + water | 21.8 | 30.9 | 100 |
| J042 + Bil-C (20 mg/dL) | 21.8 | 30.9 | 100 |
| J042 + Bil-F (20 mg/dL) | 22.1 | 31.3 | 101 |
| J042 + hemolytic Hb (500 mg/dL) | 22.3 | 31.6 | 102 |
| J042 + chyle (1400 FTU) | 22.9 | 32.4 | 105 |
| J042 + Intralipos (1%) | 22.5 | 31.9 | 103 |
| J042 + ascorbic acid (50 mg/dL) | 20.9 | 29.6 | 96 |

TABLE 44

| • PLAC Test | | | |
|---|---|---|---|
| Sample | ΔmAbs/min | nmol/min/mL | % |
| J042 + water | 182.1 | 139.2 | 100 |
| J042 + Bil-C (20 mg/dL) | 181.1 | 138.2 | 99 |
| J042 + Bil-F (20 mg/dL) | 188.4 | 145.5 | 105 |
| J042 + hemolytic Hb (500 mg/dL) | ND | ND | ND |
| J042 + chyle (1400 FTU) | 176.9 | 134.0 | 96 |
| J042 + Intralipos (1%) | ND | ND | ND |
| J042 + ascorbic acid (50 mg/dL) | 181.0 | 138.1 | 99 |

TABLE 45

| | • Lp-PLA$_2$ FS | | |
|---|---|---|---|
| Sample | ΔmAbs/min | U/L | % |
| J042 + water | 28.8 | 343.5 | 100 |
| J042 + Bil-C (20 mg/dL) | 28.9 | 344.7 | 100 |
| J042 + Bil-F (20 mg/dL) | 29.4 | 351.0 | 102 |
| J042 + hemolytic Hb (500 mg/dL) | 27.8 | 330.8 | 96 |
| J042 + chyle (1400 FTU) | 30.0 | 358.6 | 104 |
| J042 + Intralipos (1%) | 29.5 | 352.3 | 103 |
| J042 + ascorbic acid (50 mg/dL) | 28.8 | 343.5 | 100 |

The measurement results in Tables 43 and 45 show that all of the samples containing the different substances could be measured within an error range of ±5% using the method of the invention and Lp-PLA$_2$ FS. As shown in Table 44, moreover, the hemolytic hemoglobin (500 mg/dL) and Intralipos Infusion (1%) samples could not be measured with the PLAC Test, and appeared as "Absorbance error (due to upper limit beyond)" on the Hitachi 7600-010S used in this example.

These examples show that the method of the invention and Lp-PLA$_2$ FS are not affected by hemolytic hemoglobin and Intralipos (chyle), while the PLAC Test was affected by hemolytic hemoglobin and Intralipos (chyle).

Example 20

<Comparing Measurement Values with Reagents of Invention, PLAC Test and Lp-PLA$_2$ FS>

The Lp-PLA$_2$ activity values measured in each sample with the reagents of the invention, PLAC Test and Lp-PLA$_2$ FS were compared. The reagent compositions were the same as in Example 17.

(Samples)

Pooled serums A to C, heparin pooled plasma, citrated pooled plasma, individual serums Nos. 1 to 21.

(Activity Measurement)

The activity measurement equipment, measurement parameters and calculations of activity values were the same as in Example 17.

Table 46 shows Lp-PLA$_2$ activity values (nmol/min/mL and U/L) for each sample as measured with the reagents of the invention, PLAC Test and Lp-PLA$_2$ FS. FIG. 13 shows a comparison of the activity values from the PLAC Test (x-axis (nmol/min/mL)) and the activity values obtained with the reagents of the invention (y-axis (nmol/min/mL)), while FIG. 14 shows a comparison of the activity values obtained with Lp-PLA$_2$ FS (x-axis (U/L)) with the activity values obtained with the reagents of the invention (y-axis (nmol/min/mL)), and FIG. 15 shows a comparison of the activity values from the PLAC Test (x-axis (nmol/min/mL)) and the activity values obtained with Lp-PLA$_2$ FS (y-axis (U/L)). Chyle is indicated by +.

TABLE 46

| Sample | Chyle | Reagents of invention (nmol/min/mL) | PLAC Test (nmol/min/mL) | Lp-PLA$_2$ FS(U/L) |
|---|---|---|---|---|
| Pooled serum A | | 1.1 | 4.5 | 10.9 |
| Pooled serum B | + | 33.4 | 147.4 | 384.2 |
| Pooled serum C | + | 32.2 | 155.9 | 374.5 |
| Heparin pooled plasma | + | 26.1 | 122.2 | 304.4 |
| Citrated pooled plasma | + | 25.8 | 142.0 | 309.3 |
| Individual serum No. 1 | ++ | 32.7 | 154.9 | 360.0 |
| Individual serum No. 2 | + | 32.2 | 168.0 | 369.7 |
| Individual serum No. 3 | + | 42.1 | 179.7 | 468.7 |
| Individual serum No. 4 | + | 46.0 | 198.0 | 517.1 |
| Individual serum No. 5 | + | 36.3 | 161.4 | 396.3 |
| Individual serum No. 6 | + | 33.0 | 169.1 | 373.3 |
| Individual serum No. 7 | + | 18.3 | 90.9 | 201.8 |
| Individual serum No. 8 | + | 37.4 | 155.6 | 443.4 |
| Individual serum No. 9 | + | 47.9 | 203.1 | 543.6 |
| Individual serum No. 10 | + | 43.5 | 208.6 | 491.7 |
| Individual serum No. 11 | + | 41.8 | 170.4 | 472.4 |
| Individual serum No. 12 | | 33.2 | 180.5 | 378.1 |
| Individual serum No. 13 | + | 52.8 | 193.7 | 594.4 |
| Individual serum No. 14 | + | 32.9 | 142.8 | 370.9 |
| Individual serum No. 15 | + | 33.9 | 167.7 | 391.4 |
| Individual serum No. 16 | ++ | 75.9 | 226.7 | 849.3 |
| Individual serum No. 17 | +++ | 39.4 | ND | 412.0 |
| Individual serum No. 18 | + | 37.4 | 172.4 | 416.8 |
| Individual serum No. 19 | + | 38.3 | 163.6 | 444.6 |
| Individual serum No. 20 | | 32.0 | 165.6 | 362.4 |
| Individual serum No. 21 | + | 25.5 | 117.0 | 254.9 |

Based on these measurement results, the correlation between the sample measurement values obtained with the method of the invention and Lp-PLA$_2$ FS can be represented by correlation equation y=0.0885x+0.0643, correlation coefficient r=0.996. The method of the invention is superior to Lp-PLA$_2$ FS in that Lp-PLA$_2$ FS is a complicated three-reagent system while the method of the invention uses a simple two-reagent system.

Moreover, the correlation between the sample measurement values obtained with the method of the invention and the PLAC Test can be represented by correlation equation y=0.2698x−7.0906, correlation coefficient r=0.991. In the case of the individual serum No. 17, which had particularly strong chyle, measurement was not possible with the PLAC Test, and an "Absorbance overerror" message appeared on the Hitachi 7600-010S used in this example. Considered together with the results for Example 19, this shows that the PLAC test is more vulnerable to the effects of hemolytic hemoglobin and chyle than the method of the invention. Consequently, as shown in these examples, the method of the invention is superior to the PLAC test because it is resistant to the effects of hemolytic hemoglobin and Intralipos Infusion (chyle).

The correlation between the measurement values obtained with Lp-PLA$_2$ FS and the PLAC Test can be represented by correlation equation y=3.0609x−81.691, correlation coefficient r=0.896.

Because the activity values are defined differently, the activity values measured with Lp-PLA$_2$ FS, PLAC Test and the reagents of the invention are different, and the slope of the correlation equation is not 1, but it is thought that the slope of the correlation equation would approach 1 if the activity value definitions and the calibrator values were identical.

Example 21

<Dilution Linearity of Reagents of Invention, PLAC Test and Lp-PLA$_2$ FS>

The dilution linearity of the reagents of the invention, PLAC Test and Lp-PLA$_2$ FS were compared. The reagent compositions were the same as in Example 17.

(Samples)

The following dilution series (total 6 dilutions) was prepared from pooled serum J042 with 0.05 mg/mL of rLp-PLA$_2$ added thereto (hereunder called Serum X) and physiological saline (Otsuka Pharmaceutical Co., Ltd.):

Serum X alone (1),
Serum X:Saline=3:1 (0.75),
Serum X:Saline=1:1 (0.5),
Serum X:Saline=1:3 (0.25),
Serum X:Saline=1:9 (0.1), and
Saline alone (0).

(Activity Measurement)

The activity measurement equipment, measurement parameters and calculations of activity values were the same as in Example 17.

In FIGS. 16 to 18, the dilution series is plotted on the x-axis and absorbance change per minute on the y-axis for each reagent.

The measurement results in FIG. 16 show that the dilution linearity with the reagents of the invention is y=48.851x−0.7186 (r=0.999). In FIG. 18, the dilution linearity with Lp-PLA$_2$ FS is y=62.481x−0.0086 (r=0.999). As shown in FIG. 17, the PLAC Test did not exhibit dilution linearity.

Example 22

<Test of Storage Stability of Reagents of Invention at 4° C.>

The reagents of the invention were stored for 1, 2, 3, 4, 5, 6, 8, 15, 29, 60 and 120 days at 4° C. following reagent preparation, and used to measure the Lp-PLA$_2$ sensitivity (ΔmAbs/min) of the pooled serum J042. The reagent compositions were as follows.

(Reagents of Invention)
<R1 Reagent>

| | |
|---|---|
| 50 mM | Tris-HCl (pH 7.8) |
| 0.2 mM | CaCl$_2$ |
| 4 U/mL | ASOM |
| 0.05% | ProClin 300 |
| 1.6 μM | Potassium ferrocyanide |
| 0.05% | EMULGEN 1150S-60 |
| 3.3 U/mL | Recombinant lyso-PAF-PLD |
| 0.1 mM | EDTA |
| 75 mM | NaCl |
| 3% | Trehalose |
| 10 μM | FAD (flavin adenine dinucleotide) |
| 0.02% | TODB |
| 4 U/mL | Peroxidase |
| 4 U/mL | Recombinant choline oxidase III |

<R2 Reagent>

| | |
|---|---|
| 50 mM | PIPES (pH 7.0) |
| 0.2 mM | CaCl$_2$ |
| 0.05% | ProClin 300 |
| 0.05% | EMULGEN 1150S-60 |
| 0.1 mM | EDTA |
| 0.25% | KCl |
| 0.13% | Sucrose |
| 0.08% | 4-AA |
| 2 mM | Racemic PAF (C16) |

(Samples)

Pooled serum J042.

(Activity Measurement)

A Hitachi 7170 automatic analyzer was used to measure activity. The measurement parameters are shown below. The activity values were measured under the same conditions as those used with the reagents of the invention in Example 17.

(Hitachi 7170 Automatic Analyzer Measurement Parameters)

| Analysis method | Rate A |
|---|---|
| Measurement wavelength (sub/dominant) | 660 nm/546 nm |
| Reaction time | 10 minutes |
| Measuring points | 30 to 33 |
| Sample volume | 4 μL |
| R1 reagent volume | 160 μL |
| R2 reagent volume | 40 μL |

In the measurement results, given 100% as the sensitivity and activity value measured with the reagent that was stored for 1 day at 4° C. after preparation, the Lp-PLA$_2$ sensitivity (ΔmAbs/min) and activity values for the pooled serum J042 remained within ±10% for at least 120 days, showing clearly that the Lp-PLA$_2$ activity measurement method and measurement kit of the present invention can measure Lp-PLA$_2$ stably, with high sensitivity and accurately even when the reagents have been stored for a long period of time (at least 120 days at 4° C.).

Example 23

<Storage Stability Test of Reagents of Invention: 37° C. Heat Acceleration Test>

Reagents of the invention that had been stored for 1 week at 4° C. after preparation were then stored for 1 week at 37° C. and 2 weeks at 37° C., and sensitivity to Lp-PLA$_2$ in the following samples was measured. The reagent compositions were as follows, and activity measurement was performed as in Example 22.

(Reagents of Invention)
<R1 Reagent>

| | |
|---|---|
| 50 mM | Tris-HCl (pH 7.8) |
| 0.2 mM | CaCl$_2$ |
| 4 U/mL | ASOM |
| 0.05% | ProClin 300 |
| 1.6 μM | Potassium ferrocyanide |
| 0.05% | EMULGEN 1150S-60 |
| 3.3 U/mL | Recombinant lyso-PAF-PLD |
| 0.1 mM | EDTA |
| 75 mM | NaCl |
| 3% | Trehalose |
| 10 μM | FAD (flavin adenine dinucleotide) |
| 0.02% | TODB |
| 4 U/mL | Peroxidase |
| 4 U/mL | Recombinant choline oxidase III |

<R2 Reagent>

| | |
|---|---|
| 50 mM | PIPES (pH 7.0) |
| 0.2 mM | $CaCl_2$ |
| 0.05% | ProClin 300 |
| 0.05% | EMULGEN 1150S-60 |
| 0.1 mM | EDTA |
| 0.25% | KCl |
| 0.13% | Sucrose |
| 0.08% | 4-AA |
| 2 mM | Racemic PAF (C16) or 1-palmitoyl-2-acetyl-sn-glycero-3-PC |

(Samples)

Pooled serum J042, pooled serums B to D, serum pool J042 solution containing 0.017 mg/mL $rLp-PLA_2$ In storage testing of the reagents of the invention using racemic PAF (C16) or 1-palmitoyl-2-acetyl-sn-glycero-3-PC as the substrate, the sensitivity and activity values of the reagents of the invention after 2 weeks of storage at 37° C. were within ±10% given 100% as the sensitivity and activity values measured with reagents that had been stored for 1 day at 4° C. after preparation. $Lp-PLA_2$ activity could be measured stably, sensitively and accurately with reagents of the invention that had been stored for at least 2 weeks at 37° C. Since storage stability after 2 weeks at 37° C. is predicted to be equivalent to storage stability after 18 months at 4° C., the reagents of the invention should be stable for at least 18 months at 4° C.

Example 24

<$Lp-PLA_2$ Activity Measurement of Stored Samples 1>

Individual serums A to D that were obtained by centrifugation immediately after blood collection were subdivided, and stored at three temperatures (4° C., −25° C., −80° C.) beginning one hour after blood collection. The $Lp-PLA_2$ activity of the individual serums A to D was then measured (n=3) after 1 or 2 hours or 1, 2, 3, 4, 7, 15 or 28 days of storage at 4° C. or after 1 hour or 1, 2, 3, or 4 days of storage at −25° C. and −80° C. The reagent compositions were the same as in Example 22. A Hitachi 7170 automatic analyzer was used for measurement, and the measurement parameters were the same as in Example 22. The serum pool J042-11, which was found to have an $Lp-PLA_2$ concentration of 23.1 (nmol/min/mL (U/L)) in Reference Example 11, was used as a calibration reagent.

$Lp-PLA_2$ concentrations were measured by the "Method 2 for calculating $Lp-PLA_2$ activity value" described above, and a single-point calibration using a calibration reagent and distilled water measured at the same time as 0 (nmol/min/mL (U/L)) was selected as the calibration method.

In the measurement results, the $Lp-PLA_2$ activity measurement values (nmol/min/mL (U/L)) of the individual serums A to D after sample storage for 28 days at 4° C. beginning 1 hour after blood collection were all within ±11% given 100% as the measurement values of the individual serums A to D that were stored for 1 hour at 4° C. beginning 1 hour after blood collection. When samples were stored at −25° C. or −80° C. for 1, 2, 3 or 4 days beginning 1 hour after blood collection, the $Lp-PLA_2$ activity measurement values (nmol/min/mL (U/L)) were within ±6% given 100% as the measurement values of samples after 1 hour of storage at 4° C. beginning 1 hour after blood collection. The $Lp-PLA_2$ activity measurement values in samples that could be measured by the method of the invention were stable at a range of −80° C. to 4° C. (which includes the ordinary specimen storage temperature range), showing clearly that the method of the present invention is highly versatile and useful.

According to the literature (Clinical Biochemistry 44 (2011), 1247-1252), $Lp-PLA_2$ activity measurement values in ELISA were 15% higher in samples stored for 2 days at 4° C. and 30% higher in samples stored for 2 days at −25° C. in comparison to samples before storage, indicating that sample storage has a large effect of $Lp-PLA_2$ activity measurement values. As discussed above, however, the effect of sample storage on activity measurement values was less when $Lp-PLA_2$ activity was measured by the method of the invention, which is evidence for the usefulness of the method of the invention.

Example 25

<$Lp-PLA_2$ Activity Measurement of Stored Samples 2>

The individual serum E was frozen and thawed 0 to 5 times, and $Lp-PLA_2$ activity was measured. The reagents, measurement conditions and the like were as in Example 22. The calibration reagent and calibration method were as in Example 24.

The measurement results show that the measurements of $Lp-PLA_2$ activity in samples that had been repeatedly frozen and thawed 5 times were all within ±4% given 100% as the $Lp-PLA_2$ activity measurement in the sample before freezing and thawing. The results of Examples 24 and 25 show clearly that with the method of the invention, $Lp-PLA_2$ activity can be measured stably, with high sensitivity and accurately in samples that have been stored at least at temperatures in the range of −80° C. to 4° C.

Example 26

<LOB, LOD and LOQ Measurement>

The limit of blank (LOB), limit of detection (LOD) and limit of quantitation (LOQ) of the reagents of the invention were measured in accordance with Standard: CLSI EP17 (Evaluation of Detection Capability for Clinical Laboratory Measurement Procedures: Approved Guideline (IEEE)). The reagent compositions were the same as in Example 22. A Hitachi 7170 automatic analyzer was used for measurement, and the measurement parameters were as in Example 22. The calibration reagent and calibration method were as in Example 24.

(Samples)

BJ pool diluted with physiological saline (0.9 w/v % NaCl) to $Lp-PLA_2$ concentrations of 0.0, 1.4, 2.9, 4.3, 5.8, 7.2, 8.7, 10.1, 11.6, 13.0 and 14.5 U/L.

(Measurement)

The samples were measured every day for 5 days (n=5), and the coefficient of variation (CV %), average CV and 2SD (standard deviation×2) were calculated. The results are shown in FIG. 19. In FIG. 19, 2SD of CV (%) is shown with an error bar, and the $Lp-PLA_2$ concentrations and coefficients of variation are power-approximated and shown as a solid line ($y=37.644x^{-1.155}$).

(LOB)

The LOB was 0.346 (nmol/min/mL (U/L)) as calculated by the following formula from the average coefficient of variation at an $Lp-PLA_2$ concentration of 0 (nmol/min/mL (U/L)), or in other words of saline, and the standard deviation of the coefficient of variation.

$$LOB = \text{Average} + 1.645 \times SD$$
$$= 0.346 + 1.645 \times 0.2862$$
$$= 0.346$$

(LOD)

The LOD was 0.810 (nmol/min/mL (U/L)) as calculated by the following formula from the LOB and the standard deviation (0.2804) of the measurement values at an Lp-PLA$_2$ concentration of 1.4 (nmol/min/mL (U/L)).

$$LOD = LOB + 1.653 \times SD$$
$$= 0.346 + 1.653 \times 0.2804$$
$$= 0.810$$

(LOQ)

As for the LOQ, the LOQ was defined as the measured value at which the CV (%) was 5% or less based on a power approximation of the Lp-PLA$_2$ concentration and coefficient of variation (y=37.644x$^{-1.155}$) as shown in FIG. 19, and was thus calculated as 5.742 (nmol/min/mL (U/L)).

$$LOQ = (5/37.644)^{(1/-1.155)} = 5.742$$

The results of this example show that the minimum amount of Lp-PLA$_2$ that can be detected with the method of the invention is about 0.810 (U/L), while the smallest value at which the quantitative results are sufficiently reliable is about 5.742 (U/L), and since the LOB and LOQ are expected to be roughly equivalent even if the reagent compositions change, this confirms that the method of the invention is applicable to practical uses.

Example 27

<PLD Activity of Lyso-PAF-PLD Mutants with Introduced Site-Specific Mutations>

Site-specific mutations were introduced by substituting M in the 45th position of the lyso-PAF-PLD of SEQ ID NO: 9 (corresponding to M in the 71st position of SEQ ID NO: 1) with G, A, L or D, and PLD activity against lyso-PAF ($k_{cat}/K_m$ (s$^{-1}$ mM$^{-1}$)) was compared before and after mutation. As a result, the pre-mutation PLD activity was 1385 (s$^{-1}$ mM$^{-1}$), but the mutant having G substituted for the M in the 45th position of SEQ ID NO: 9 (called M45G) and the similarly-named mutants M45A, M45L and M45D had PLD activities of 3059, 11411, 3284 and 4557 (s$^{-1}$mM$^{-1}$), respectively.

Site-specific mutations were also introduced by substituting F in the 257th position of lyso-PAF-PLD of SEQ ID NO: 9 (corresponding to F in the 283rd position of SEQ ID NO: 1) with G, E, R, K or W, and the PLD activity against lyso-PAF ($k_{cat}/K_m$(s$^{-1}$mM$^{-1}$)) was compared before and after mutation. As a result, the PLD activity was 1385 (s$^{-1}$mM$^{-1}$) before the mutation, but the mutant having G substituted for F in the 257th position of SEQ ID NO: 1 (called F257G) and the similarly-named mutants F257E, F257R, F257K and F257W had PLD activities 1200, 1000, 1080, 1020 and 1320, respectively.

The PLD activity of the lyso-PAF-PLD mutants obtained by site-specific mutations was measured as follows. 1.211 g of Tris, 14.7 mg of calcium chloride dihydrate (Wako Pure Chemical Industries, Ltd.), 20 mL of lyso-PAF solution and 2 mL of 1% TODB solution were dissolved in 60 mL of purified water, the pH was adjusted to 7.5 (25° C.) with 1 N HCl, 4 mL of 100 U/mL choline oxidase, 4 mL of 100 U/mL peroxidase solution and 2 mL of 1% 4-AA solution were added and dissolved, and the total was brought to 100 mL with purified water to obtain a PLD activity measurement reagent for lyso-PAF (reaction reagent mixture). The lyso-PAF solution was adjusted so that the lyso-PAF concentration in the reaction reagent mixture was 0 to 5 mM. 3 mL of the reaction reagent mixture was pre-heated for 5 minutes at 37° C., and mixed with 50 µL of a solution of the lyso-PAF-PLD mutant with the introduced site-specific mutation diluted appropriately with 10 mM Tris-HCl (pH 7.5) to initiate a reaction, and the change in absorbance at 546 nm was measured for 1 minute between 8 and 9 minutes after initiation of the reaction. The activity value (µmole/min) was calculated given 36 (cm$^2$/µmole) as the millimolar extinction coefficient of the quinoneimine dye at 546 nm. The protein content (mg/mL) was calculated by the Bradford method using bovine serum albumin as the standard. $K_m$ and $k_{cat}$ were calculated by the Michaelis-Menten formula in accordance with the methods described in the aforementioned Theory and Practice on Enzymes and other Proteins [*Tanpakushitsu/Kouso no kiso jikkenhou*] and in Voet's Basic Biochemistry (Fourth Ed.) and the like. For purposes of calculation, the molecular weight of the enzyme was given as 33583.

The PLD activity ($k_{cat}/K_m$ (s$^{-1}$mM$^{-1}$)) of each mutant is shown in Table 47.

TABLE 47

| WT/Mutant | $K_m$ (mM) | $k_{cat}$ (s$^{-1}$) | $k_{cat}/K_m$(s$^{-1}$mM$^{-1}$) |
|---|---|---|---|
| WT | 0.058 | 81 | 1385 |
| M45G | 0.027 | 82 | 3059 |
| M45A | 0.012 | 136 | 11411 |
| M45L | 0.023 | 147 | 3284 |
| M45D | 0.034 | 157 | 4557 |
| F257G | 0.13 | 156 | 1200 |
| F257E | 0.10 | 100 | 1000 |
| F257R | 0.15 | 162 | 1080 |
| F257K | 0.090 | 92 | 1020 |
| F257W | 0.10 | 132 | 1320 |

Thus, site-specific mutants of lyso-PAF-PLD had similar PLD activity to that of the wild type.

The reagents and methods of the invention are widely applicable and convenient because they allow Lp-PLA$_2$ activity to be measured using a general-purpose automatic analyzer. The measurement method has also been shown to be safe because Lp-PLA$_2$ activity can be measured without using any radioactive isotopes or the like. Moreover, the method has also been shown to be stable against carbon dioxide gas in the air because measurement can be performed under neutral conditions. Moreover, it has been shown that the method may accurately reflect in vivo activity because it uses PAF, which is an endogenous substrate of Lp-PLA$_2$. The method is also economical because the reagents used in the examples and the like are readily available from commercial sources and can be easily prepared.

INDUSTRIAL APPLICABILITY

The measurement method and kit of the invention can measure Lp-PLA$_2$ activity in a sample easily, stably and with a high degree of sensitivity. Therefore, the present invention is particularly useful for diagnosing and managing diseases or conditions such as cardiovascular disease that are associated with Lp-PLA$_2$, and can be used in the medical field and the reagent industry.

The present application claims priority based on Japanese Patent Application No. 2016-123707 filed on Jun. 22, 2016, and the entire contents thereof are incorporated herein by reference.

What is claimed is:

1. An assay method comprising:
allowing an enzyme to hydrolyze lyso-platelet-activating factors (lyso-PAFs) in the presence of platelet-activating factors (PAFs) to thereby produce choline by hydrolysis of the lyso-PAFs without producing choline by hydrolysis of the PAFs, the PAFs being represented by General Formula I below:

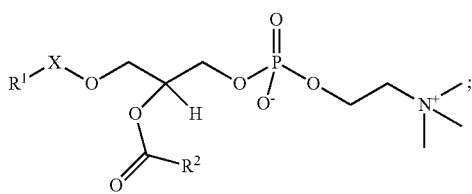

and
measuring the amount of choline produced,
wherein:
$R^1$ is a linear or branched, saturated or partially unsaturated higher hydrocarbon group;
$R^2$ is a linear lower alkyl group; and
X is —C(O)—, —CH$_2$— or —CH═CH—;
the lyso-PAFs being represented by General Formula II below:

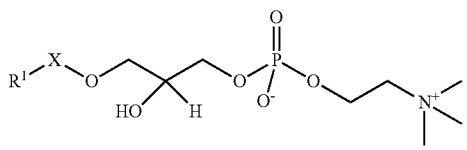

wherein $R^1$ and X are defined as in General Formula I, and the enzyme being a protein according to any of (a) to (c) below:
(a) a protein comprising SEQ ID NO: 1 or 9;
(b) a protein comprising SEQ ID NO: 1 or 9 and having 1 to 9 amino acids deleted, substituted or added therein, and having phospholipase D-like (PLD) activity against lyso-PAF but no PLD activity against PAF; or
(c) a protein having at least 90% sequence identity to SEQ ID NO: 1 or 9, and having PLD activity against lyso-PAF but no PLD activity against PAF.

2. The method according to claim 1, wherein the measuring comprises directly measuring the amount of choline produced.

3. The method according to claim 1, wherein the measuring comprises: reacting the choline with choline oxidase to produce hydrogen peroxide; and measuring the amount of hydrogen peroxide produced.

4. A method for measuring lipoprotein-associated phospholipase A2 (Lp-PLA$_2$) activity in a sample containing Lp-PLA$_2$, the method comprising the following steps (A) to (C):
(A) converting platelet-activating factors (PAFs) represented by General Formula I below:

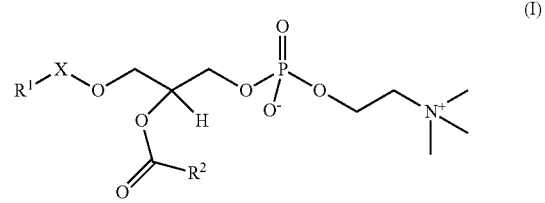

wherein:
$R^1$ is a linear or branched, saturated or partially unsaturated higher hydrocarbon group;
$R^2$ is a linear lower alkyl group; and
X is —C(O)—, —CH$_2$— or —CH═CH—,
into lyso-PAFs represented by General Formula II below:

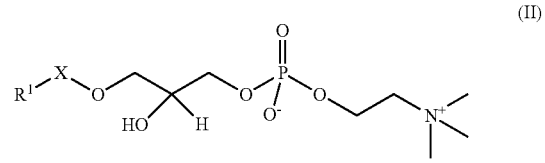

wherein $R^1$ and X are defined as in General Formula I, by reacting the PAFs with the Lp-PLA$_2$ in the sample;
(B) hydrolyzing the lyso-PAFs produced in step (A) with an enzyme that is a protein according to any of (a) to (c) below to obtain hydrolysate:
(a) a protein comprising SEQ ID NO: 1 or 9,
(b) a protein comprising SEQ ID NO: 1 or 9 and having 1 to 9 amino acids deleted, substituted or added therein, and having phospholipase D-like (PLD) activity against lyso-PAF but no PLD activity against PAF, or
(c) a protein having at least 90% sequence identity to SEQ ID NO: 1 or 9, and having PLD activity against lyso-PAF but no PLD activity against PAF; and
(C) measuring Lp-PLA$_2$ activity in the sample by utilizing a quantitative change attributable to the hydrolysate obtained in step (B) as an indicator.

5. The method according to claim 4, wherein the quantitative change in step (C) is a change in the amount of hydrolysate choline.

6. The method according to claim 5, wherein the step (C) also comprises a following step (C-1) as a method of measuring the change in the amount of choline:
(C-1) reacting choline with choline oxidase to produce hydrogen peroxide.

7. The method according to claim 6, wherein the step (C) also comprises a following step (C-2):
(C-2) measuring the amount of hydrogen peroxide produced in the step (C-1) by a colorimetric method using a chromogenic reagent.

8. The method according to claim 4, further comprising a following step (D) prior to the step (A):

(D) removing the choline in the sample.

9. The method according to claim 8, wherein the step (D) is removing the choline in the sample by utilizing choline oxidase.

10. The method according to claim 4, wherein $R^2$ is a methyl group.

11. The method according to claim 4, wherein $R^1$ is independently selected from $C_{15}$ and $C_{17}$ linear alkyl groups.

12. The method according to claim 4, wherein X is —$CH_2$—.

13. The method according to claim 4, wherein X is —C(O)—.

* * * * *

SEQUENCE LISTING

<160> NUMBER OF SEQ ID NOS: 9

<210> SEQ ID NO 1
<211> LENGTH: 334
<212> TYPE: PRT
<213> ORGANISM: Thermocrispum sp.
<220> FEATURE:
<223> OTHER INFORMATION: Thermocrispum sp. NITE BP-01628

<400> SEQUENCE: 1

```
Val His Pro Met Arg Ala Val Val Leu Val Val Thr Val Ala Leu
1               5                   10                  15

Val Leu Ala Phe Pro Gly Pro Ala Ala Gly Glu Thr Thr Arg Thr Thr
                20                  25                  30

Asp Asn Pro Trp Leu Asp Ala Arg Val Leu Asn Met Ala His Ala Gly
            35                  40                  45

Gly Glu Asn Glu Ala Pro Ala Asn Thr Leu Tyr Ala Phe Lys Arg Ala
        50                  55                  60

Val Lys Leu Gly Ala Asn Met Leu Glu Leu Asp Val Gln Ser Thr Lys
65                  70                  75                  80

Asp Asp Gln Leu Val Val Ile His Asn Ala Thr Val Asp Gln Thr Thr
                85                  90                  95

Asp Gly Thr Gly Lys Val Arg Asp Leu Thr Phe Glu Gln Val His Glu
            100                 105                 110

Leu Asp Ala Ala Tyr Asn Phe Ile Pro Gly Arg His Ala Val Pro Gly
        115                 120                 125

Glu Pro Pro Glu Ser Tyr Pro Leu Arg Gly Val Arg Thr Gly Glu Lys
    130                 135                 140

Lys Pro Pro Pro Gly Tyr Gln Pro Ser Asp Phe Ala Ile Pro Lys Leu
145                 150                 155                 160

Ala Asp Val Leu Glu Ala Phe Pro Arg Thr Pro Ile Asn Ile Glu Ile
                165                 170                 175

Lys Gly Thr Ser Asp Ala Asp Ile Pro Ser Phe Leu His Asn Ala Lys
            180                 185                 190

Leu Leu Ala Arg Leu Leu Lys Lys Thr Gly Arg Thr Asp Phe Ile Val
        195                 200                 205

Thr Ser Phe Asn Asp Leu Ala Val Ala Lys Phe His Leu Leu Ala Pro
    210                 215                 220

Asp Ile Pro Ile Ala Pro Gly Met Ala Gly Leu Ala Ala Tyr Phe Leu
225                 230                 235                 240

Leu Gly Val Lys Pro Met His Gly Thr Val Ala Leu Gln Ile Pro Val
                245                 250                 255

Arg Tyr Gln Gly Leu Glu Ile Ala Thr Pro Glu Phe Ile Arg Arg Ala
            260                 265                 270

His Ala Asp Gly Tyr Ala Val His Val Trp Phe Ser Gly Thr Ala Pro
        275                 280                 285

Asp Asp Glu Ala Thr Tyr Asn Arg Ile Ile Asp Ser Cys Ala Asp Gly
    290                 295                 300

Leu Met Pro Ala Tyr Pro Ala Leu Leu Glu Arg Ile Leu Asp Glu Arg
305                 310                 315                 320

Gly Ile Glu Arg Pro Gly Arg Pro Gly Val Asp Pro Cys Gly
                325                 330
```

<210> SEQ ID NO 2
<211> LENGTH: 1005
<212> TYPE: DNA

```
<213> ORGANISM: Thermocrispum sp.
<220> FEATURE:
<223> OTHER INFORMATION: Thermocrispum sp. NITE BP-01628
<220> FEATURE:
<221> NAME/KEY: CDS
<222> LOCATION: (1)..(1002)

<400> SEQUENCE: 2 gtg cac ccc atg cgc aga gcc gtt gtg ctg gtc gtc aca gtc gcg ttg      48
Val His Pro Met Arg Arg Ala Val Val Leu Val Val Thr Val Ala Leu
1               5                  10                  15 gta ctg gca ttt cct ggg ccg gcc gcg ggg gaa acc acc aga acg aca      96
Val Leu Ala Phe Pro Gly Pro Ala Ala Gly Glu Thr Thr Arg Thr Thr
            20                  25                  30 gac aat ccg tgg ctg gac gcg agg gtg ctc aac atg gcc cac gcc ggc     144
Asp Asn Pro Trp Leu Asp Ala Arg Val Leu Asn Met Ala His Ala Gly
        35                  40                  45 gga gaa aat gaa gcg cca gcg aac acg cta tac gcc ttc aag cgc gcg     192
Gly Glu Asn Glu Ala Pro Ala Asn Thr Leu Tyr Ala Phe Lys Arg Ala
50                  55                  60 gta aag ctc ggt gcg aac atg ctc gag ctg gat gtc caa tcc acc aag     240
Val Lys Leu Gly Ala Asn Met Leu Glu Leu Asp Val Gln Ser Thr Lys
65                  70                  75                  80 gac gac cag ctg gtg gtc atc cac aac gcc acc gtc gac cag acc acc     288
Asp Asp Gln Leu Val Val Ile His Asn Ala Thr Val Asp Gln Thr Thr
                85                  90                  95 gac ggc acc ggc aag gtg cgc gac ctg acg ttc gag caa gtg cac gag     336
Asp Gly Thr Gly Lys Val Arg Asp Leu Thr Phe Glu Gln Val His Glu
            100                 105                 110 ctc gac gcg gcg tac aac ttc atc ccc ggc agg cat gcg gtg ccc ggt     384
Leu Asp Ala Ala Tyr Asn Phe Ile Pro Gly Arg His Ala Val Pro Gly
        115                 120                 125 gag ccg ccg gag tcg tat cca ctg cgc ggt gtg cgg acc ggg gaa aag     432
Glu Pro Pro Glu Ser Tyr Pro Leu Arg Gly Val Arg Thr Gly Glu Lys
130                 135                 140 aag ccg ccg ccg ggc tac cag ccg tcg gat ttc gcg atc ccg aaa ctg     480
Lys Pro Pro Pro Gly Tyr Gln Pro Ser Asp Phe Ala Ile Pro Lys Leu
145                 150                 155                 160 gcc gat gtg ctc gag gcc ttc ccg cga acg ccg atc aac atc gaa atc     528
Ala Asp Val Leu Glu Ala Phe Pro Arg Thr Pro Ile Asn Ile Glu Ile
                165                 170                 175 aaa ggc acc agc gac gcg gac att cct tcg ttc ctg cac aac gcg aag     576
Lys Gly Thr Ser Asp Ala Asp Ile Pro Ser Phe Leu His Asn Ala Lys
            180                 185                 190 ctg ttg gcc cgc ctg ttg aaa aag acc ggc cgc acg gac ttc atc gtg     624
Leu Leu Ala Arg Leu Leu Lys Lys Thr Gly Arg Thr Asp Phe Ile Val
        195                 200                 205 acg tcg ttc aac gac ctc gcg gtg gcc aag ttc cat ctg ctg gcg ccc     672
Thr Ser Phe Asn Asp Leu Ala Val Ala Lys Phe His Leu Leu Ala Pro
    210                 215                 220 gac atc ccc atc gcg cct gga atg gcc ggg ctc gcc gcg tac ttc ctg     720
Asp Ile Pro Ile Ala Pro Gly Met Ala Gly Leu Ala Ala Tyr Phe Leu
225                 230                 235                 240 ctc ggc gtc aaa ccg atg cac ggc act gtc gcg ctg caa att ccg gtg     768
Leu Gly Val Lys Pro Met His Gly Thr Val Ala Leu Gln Ile Pro Val
                245                 250                 255 cgg tat cag ggc ttg gaa atc gcc acg ccg gag ttc atc cgc cgg gcg     816
Arg Tyr Gln Gly Leu Glu Ile Ala Thr Pro Glu Phe Ile Arg Arg Ala
            260                 265                 270 cac gcc gac ggc tac gcg gtg cac gtg tgg ttc agc gga acg gcg ccg     864
His Ala Asp Gly Tyr Ala Val His Val Trp Phe Ser Gly Thr Ala Pro
```

-continued

```
              275                 280                 285
gac gac gaa gcg acg tac aac cgg atc atc gac tcg tgc gcc gac ggc    912
Asp Asp Glu Ala Thr Tyr Asn Arg Ile Ile Asp Ser Cys Ala Asp Gly
        290                 295                 300 ctg atg ccc gcc tac ccg gcg ctg ctg gag cgg atc ctc gac gag cgt    960
Leu Met Pro Ala Tyr Pro Ala Leu Leu Glu Arg Ile Leu Asp Glu Arg
305                 310                 315                 320 ggc atc gag cgt ccg ggc agg ccg ggc gtc gat ccg tgc gga tga       1005
Gly Ile Glu Arg Pro Gly Arg Pro Gly Val Asp Pro Cys Gly
                    325                 330
```

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      sense primer for PCR

<400> SEQUENCE: 3
ttcatatgac caccagaacg acagacaatc                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      antisense primer for PCR

<400> SEQUENCE: 4
ttgaattctc atccgcacgg atcgacgccc                                    30

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      sense primer for PCR

<400> SEQUENCE: 5
tttcatatgc aggtcctgat ggcggc                                        26

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      antisense primer for PCR

<400> SEQUENCE: 6
tggatcctca gttgtatttt tcgatacccg                                    30

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      sense primer for PCR

<400> SEQUENCE: 7
ttgctagcat ggcggcggac agcaacg                                       27

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic antisense primer for PCR

<400> SEQUENCE: 8
gaattcttac tctttattaa gaaattttac tgcc    34

<210> SEQ ID NO 9
<211> LENGTH: 308
<212> TYPE: PRT
<213> ORGANISM: Artificial Sequence
<220> FEATURE:
<223> OTHER INFORMATION: Description of Artificial Sequence: Synthetic Thermocrispum sp. NITE BP-01628 derived sequence with initiating Met

<400> SEQUENCE: 9

```
Met Thr Thr Arg Thr Thr Asp Asn Pro Trp Leu Asp Ala Arg Val Leu
1               5                   10                  15

Asn Met Ala His Ala Gly Gly Glu Asn Glu Ala Pro Ala Asn Thr Leu
            20                  25                  30

Tyr Ala Phe Lys Arg Ala Val Lys Leu Gly Ala Asn Met Leu Glu Leu
        35                  40                  45

Asp Val Gln Ser Thr Lys Asp Asp Gln Leu Val Val Ile His Asn Ala
    50                  55                  60

Thr Val Asp Gln Thr Thr Asp Gly Thr Gly Lys Val Arg Asp Leu Thr
65                  70                  75                  80

Phe Glu Gln Val His Glu Leu Asp Ala Ala Tyr Asn Phe Ile Pro Gly
                85                  90                  95

Arg His Ala Val Pro Gly Glu Pro Glu Ser Tyr Pro Leu Arg Gly
            100                 105                 110

Val Arg Thr Gly Glu Lys Lys Pro Pro Gly Tyr Gln Pro Ser Asp
        115                 120                 125

Phe Ala Ile Pro Lys Leu Ala Asp Val Leu Glu Ala Phe Pro Arg Thr
    130                 135                 140

Pro Ile Asn Ile Glu Ile Lys Gly Thr Ser Asp Ala Asp Ile Pro Ser
145                 150                 155                 160

Phe Leu His Asn Ala Lys Leu Leu Ala Arg Leu Leu Lys Lys Thr Gly
                165                 170                 175

Arg Thr Asp Phe Ile Val Thr Ser Phe Asn Asp Leu Ala Val Ala Lys
            180                 185                 190

Phe His Leu Leu Ala Pro Asp Ile Pro Ile Ala Pro Gly Met Ala Gly
        195                 200                 205

Leu Ala Ala Tyr Phe Leu Leu Gly Val Lys Pro Met His Gly Thr Val
    210                 215                 220

Ala Leu Gln Ile Pro Val Arg Tyr Gln Gly Leu Glu Ile Ala Thr Pro
225                 230                 235                 240

Glu Phe Ile Arg Arg Ala His Ala Asp Gly Tyr Ala Val His Val Trp
                245                 250                 255

Phe Ser Gly Thr Ala Pro Asp Asp Glu Ala Thr Tyr Asn Arg Ile Ile
            260                 265                 270

Asp Ser Cys Ala Asp Gly Leu Met Pro Ala Tyr Pro Ala Leu Leu Glu
        275                 280                 285
```

```
Arg Ile Leu Asp Glu Arg Gly Ile Glu Arg Pro Gly Arg Pro Gly Val
    290                 295                 300

Asp Pro Cys Gly
305
```